(12) United States Patent
Mirkov et al.

(10) Patent No.: US 10,640,784 B2
(45) Date of Patent: May 5, 2020

(54) PATHOGEN RESISTANT CITRUS COMPOSITIONS, ORGANISMS, SYSTEMS, AND METHODS

(71) Applicant: THE TEXAS A&M UNIVERSITY SYSTEM, College Station, TX (US)

(72) Inventors: T. Erik Mirkov, Harlingen, TX (US); Kranthi Kiran Mandadi, Weslaco, TX (US)

(73) Assignee: The Texas A&M University System, College Station, TX (US)

( * ) Notice: Subject to any disclaimer, the term of this patent is extended or adjusted under 35 U.S.C. 154(b) by 163 days.

(21) Appl. No.: 15/212,041

(22) Filed: Jul. 15, 2016

(65) Prior Publication Data
US 2017/0159069 A1    Jun. 8, 2017

Related U.S. Application Data

(60) Provisional application No. 62/192,732, filed on Jul. 15, 2015.

(51) Int. Cl.
*C12N 15/82* (2006.01)
*C07K 14/415* (2006.01)

(52) U.S. Cl.
CPC ........ *C12N 15/8279* (2013.01); *C07K 14/415* (2013.01); *C12N 15/8281* (2013.01)

(58) Field of Classification Search
None
See application file for complete search history.

(56) References Cited

U.S. PATENT DOCUMENTS

| 7,432,419 | B2 | 10/2008 | Gupta |
| 7,897,847 | B2 * | 3/2011 | Simmons ............. C07K 14/415 424/93.2 |
| 2014/0109472 | A1 | 4/2014 | Mirkov et al. |
| 2015/0067918 | A1 | 3/2015 | Kress |

FOREIGN PATENT DOCUMENTS

| WO | 2013112997 A1 | 8/2013 |
| WO | 2015-031130 A1 | 3/2015 |

OTHER PUBLICATIONS

Grosser, Jude W., et al. 2009, "Grapefruit." Compendium of Transgenic Crop Plants 5:2:63-76. Published Online on Apr. 15, 2009).*
Wang et al. Phytopathology (2013), vol. 103 (7), pp. 652-665.*
Dutt, M., et al., "Progress towards Incorporation of Antimicrobial Peptides for Disease Resistance in Citrus," Session 2, Biotechnology and Genomics, Proceedings of the International Society of Citriculture, 2008, pp. 259-264.*
Broekaert et al (1997). Critical Reviews in Plant Sciences, 16(3), pp. 109-118.*
Alvarez et al. "Citrus Greening Disease (Huanglongbing) in Florida: Economic Impact, Management and the Potential for Biological Control," Agric Res, (Jun. 2016), vol. 5, No. 2, pp. 109-118.*
Environmental Protection Agency, "Defensin Proteins (SoD2 and SoD7) Derived From Spinach (*Spinacia oleracea* L.) in Citrus Plants; Temporary Exemption From the Requirement of a Tolerance", Federal Register, May 6, 2015, vol. 80, No. 87, pp. 25943-25946.
Stover, Ed et al., "Screening Antimicrobial Peptides In Vitro for Use in Developing Transgenic Citrus Resistant to Huanglongbing and Citrus Canker", Journal of the American Society for Horticultural Science, 2013, vol. 138, No. 2, pp. 142-148.
International Search Report and Written Opinion of the International Searching Authority, International Application No. PCT/US2016/042618, dated Nov. 29, 2016, 15 pages.
Larkin, M.A., et al., "Clustal W and Clustal X version 2.0," Bioinformatics Applications Note, vol. 23, No. 21, (2007), pp. 2947-2948.
Pearson, W.R., "Rapid Sequence Comparison: Rapid and Sensitive Sequence Comparison with FASTP and FASTA," Methods in Enzymology, vol. 183, (1990), pp. 63-98.
Pearson, W.R., et al., "Improved tools for biological sequence comparison," Proc. Natl. Acad. Sci., vol. 85, (Apr. 1988), pp. 2444-2448.
Dohm, J.C., et al., "The genome of the recently domesticated crop plant sugar beet (*Beta vulgaris*)," Open Letter, Nature, vol. 505, (Jan. 23, 2014), vol. 505, pp. 546-549.
Francis, M.I., et al., "Detached leaf inoculation of germplasm for rapid screening of resistance to citrus canker and citrus bacterial spot," Eur J Plant Pathol (2010), vol. 127, pp. 571-578.
Irey, M.S., et al., "Comparison of Visual Assessment and Polymerase Chain Reaction Assay Testing to Estimate the Incidence of the Huanglongbing Pathogen in Commercial Florida Citrus," Proc. Fla. State Hort. Soc., (2006), vol. 119, pp. 89-93.
Jung, S-K, et al., "Visual gene developer: a fully programmable bioinformatics software for synthetic gene optimization," BMC Bioinformatics, (2011), vol. 12, No. 340, 13 pages.
Segura, A., et al., "Novel defensin subfamily from spinach (*Spinacia oleracea*)," FEBS Letters, (1998), vol. 435, pp. 159-162.
Yang, Z.N., et al., "Agrobacterium-mediated transformation of the commercially important grapefruit cultivar Rio Red (*Citrus paradisi* Macf.)," Plant Cell Reports, (2000), vol. 19, pp. 1203-1211.
Yao, H., et al., "Evaluation of five ab initio gene prediction programs for the discovery of maize genes," Plant Molecular Biology, (2005), vol. 57, pp. 445-460.

(Continued)

*Primary Examiner* — Medina A Ibrahim
(74) *Attorney, Agent, or Firm* — Hogan Lovells US LLP

(57) ABSTRACT

The present disclosure relates, according to some embodiments, to pathogen resistant citrus compositions, organisms, systems, and methods. For example, a composition may comprise a peptide (e.g., a defensin peptide) and/or a nucleic acid (e.g., a defensin nucleic acid). A pathogen resistant citrus plant may comprise, in some embodiments, a defensin peptide and/or an expressible nucleic acid encoding a defensin peptide.

23 Claims, 30 Drawing Sheets
Specification includes a Sequence Listing.

(56) References Cited

OTHER PUBLICATIONS

Bowman et al., "Overview of Efforts to Develop HLB-Resistant Transgenic Citrus," Jan. 1, 1999, URL:http://www.mok.ufl.edu/hlb/database/pdf/00001999.pdf.
Communication pursuant to Rule 164(1) EPC and Supplementary Partial European Search Report dated Dec. 18, 2018 in EP 16 82 5283.

* cited by examiner

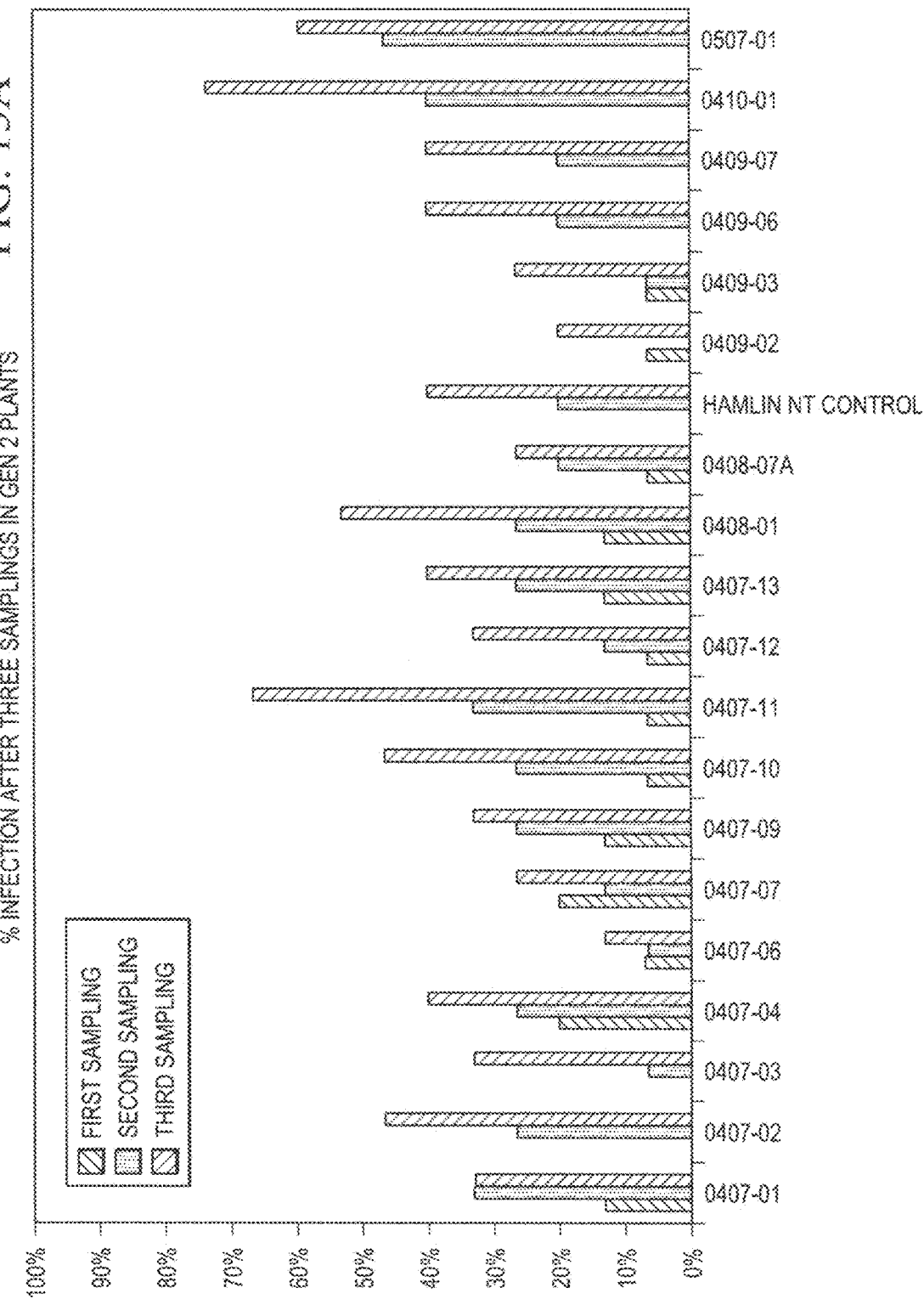

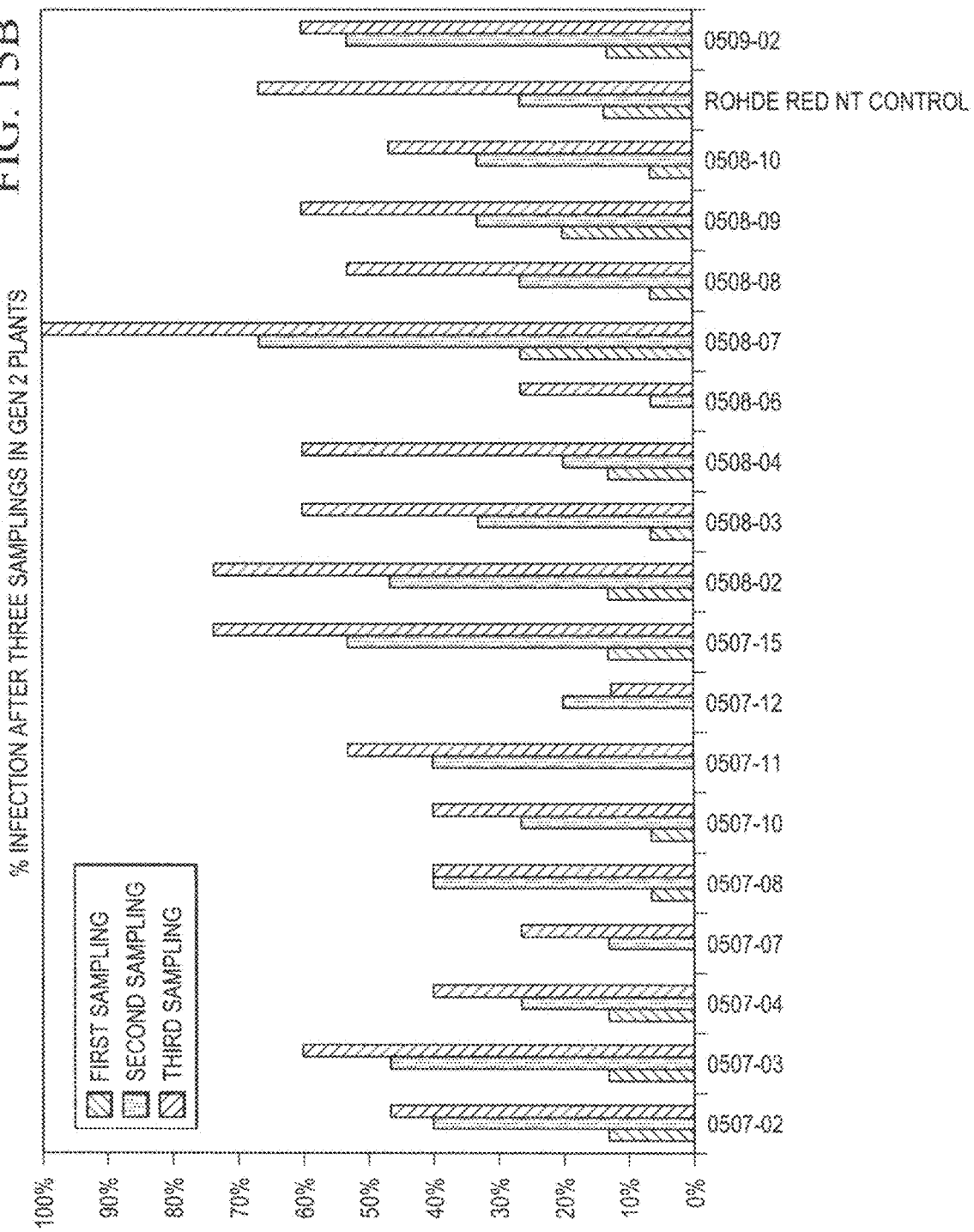

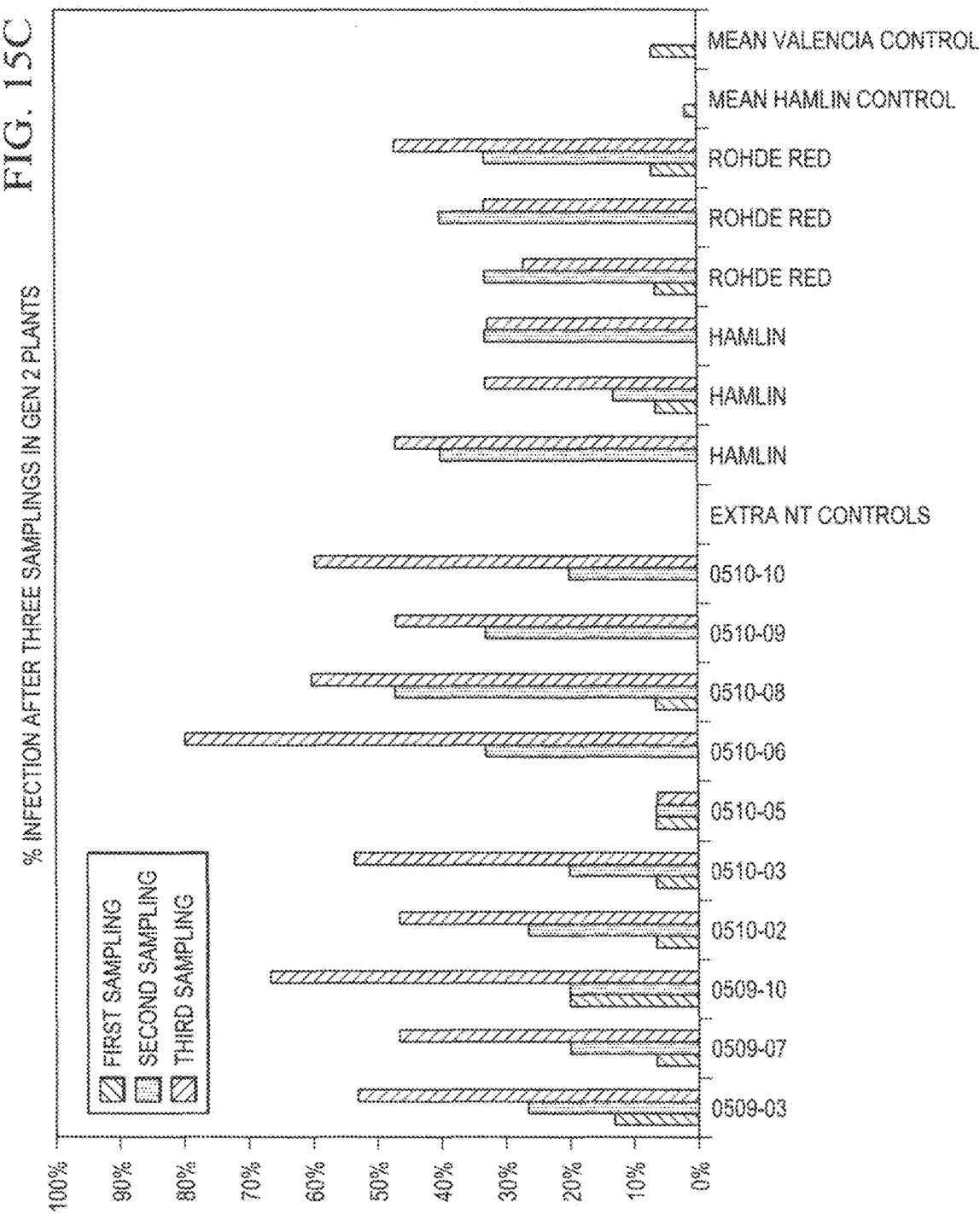

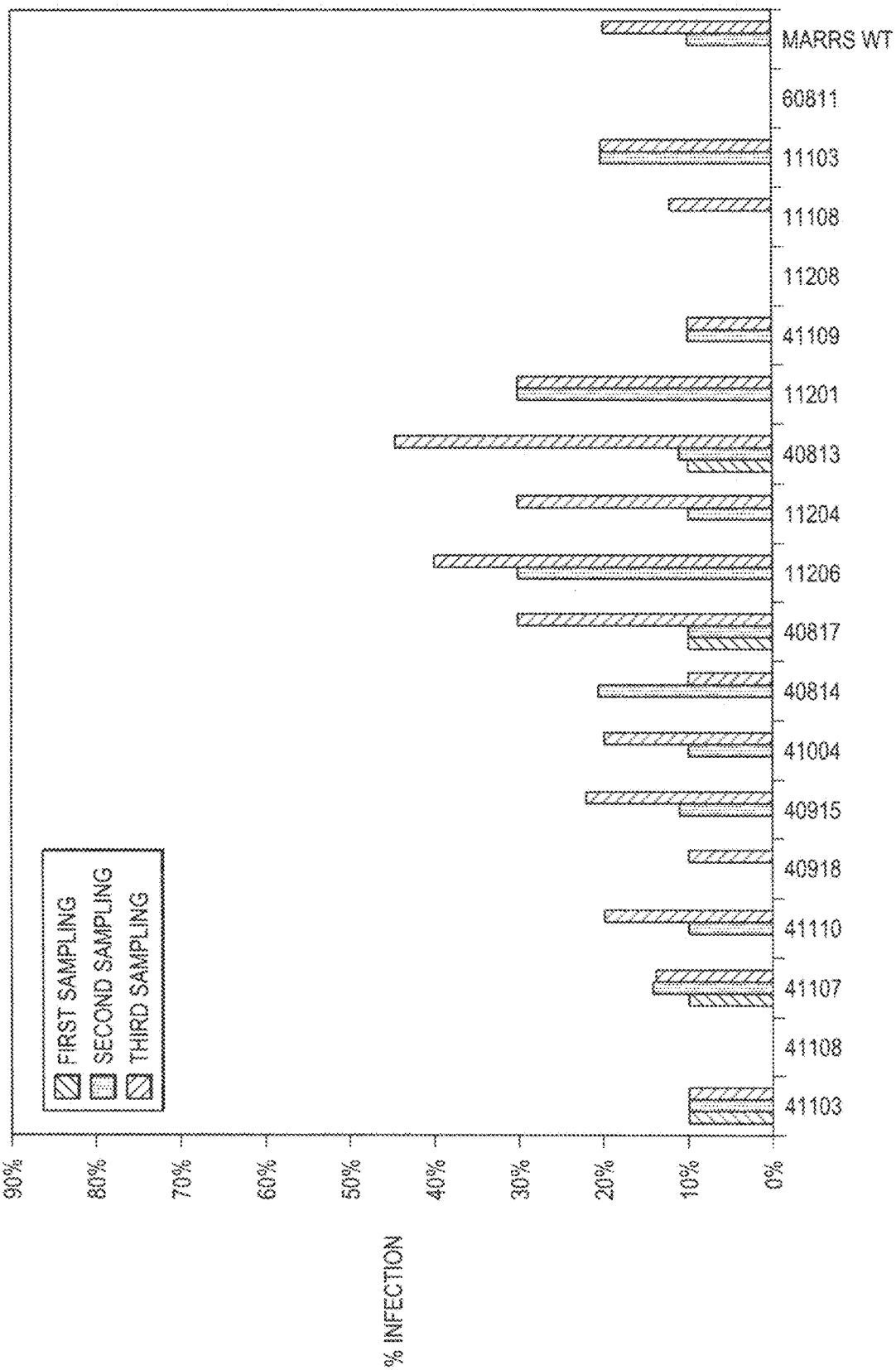

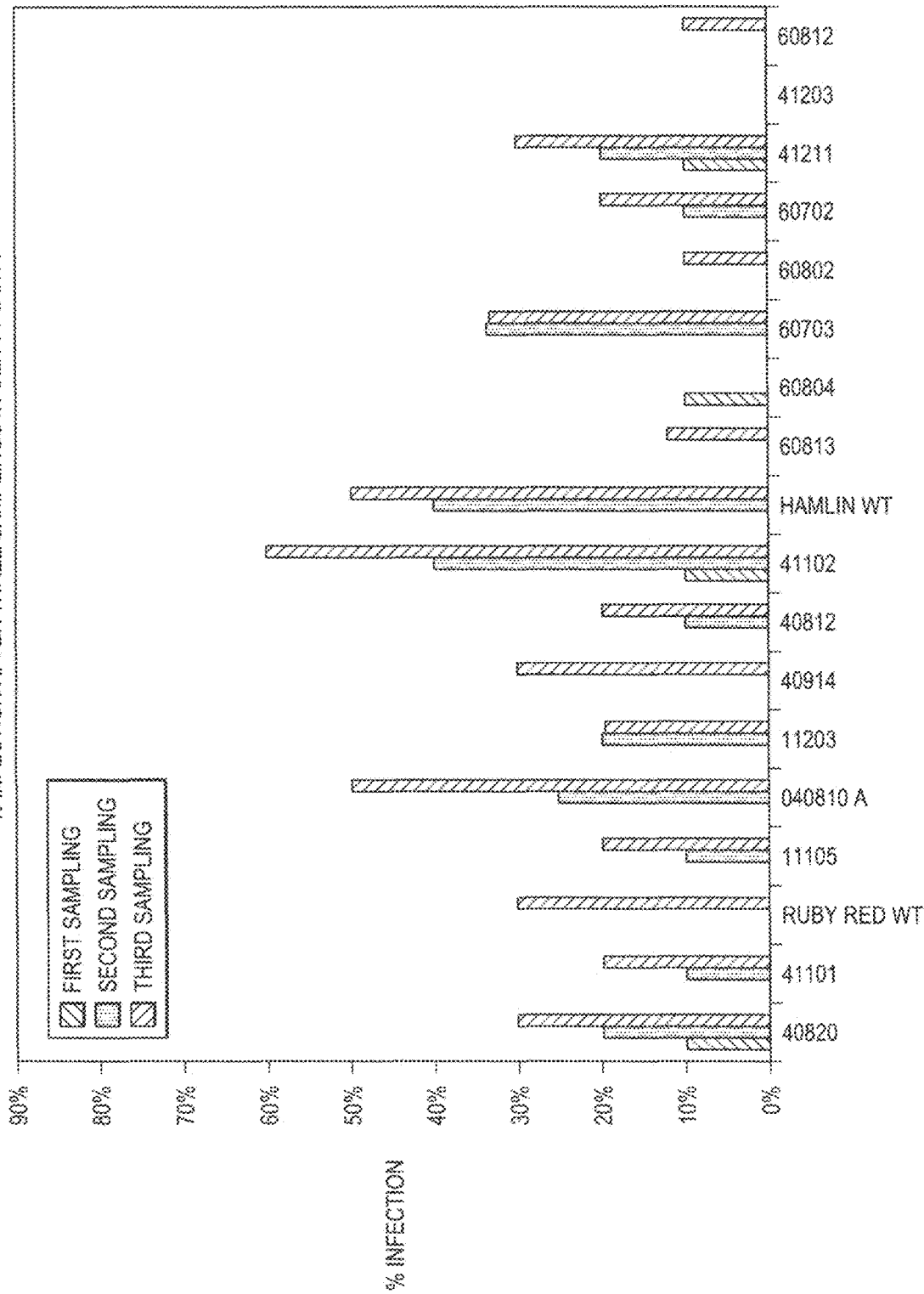

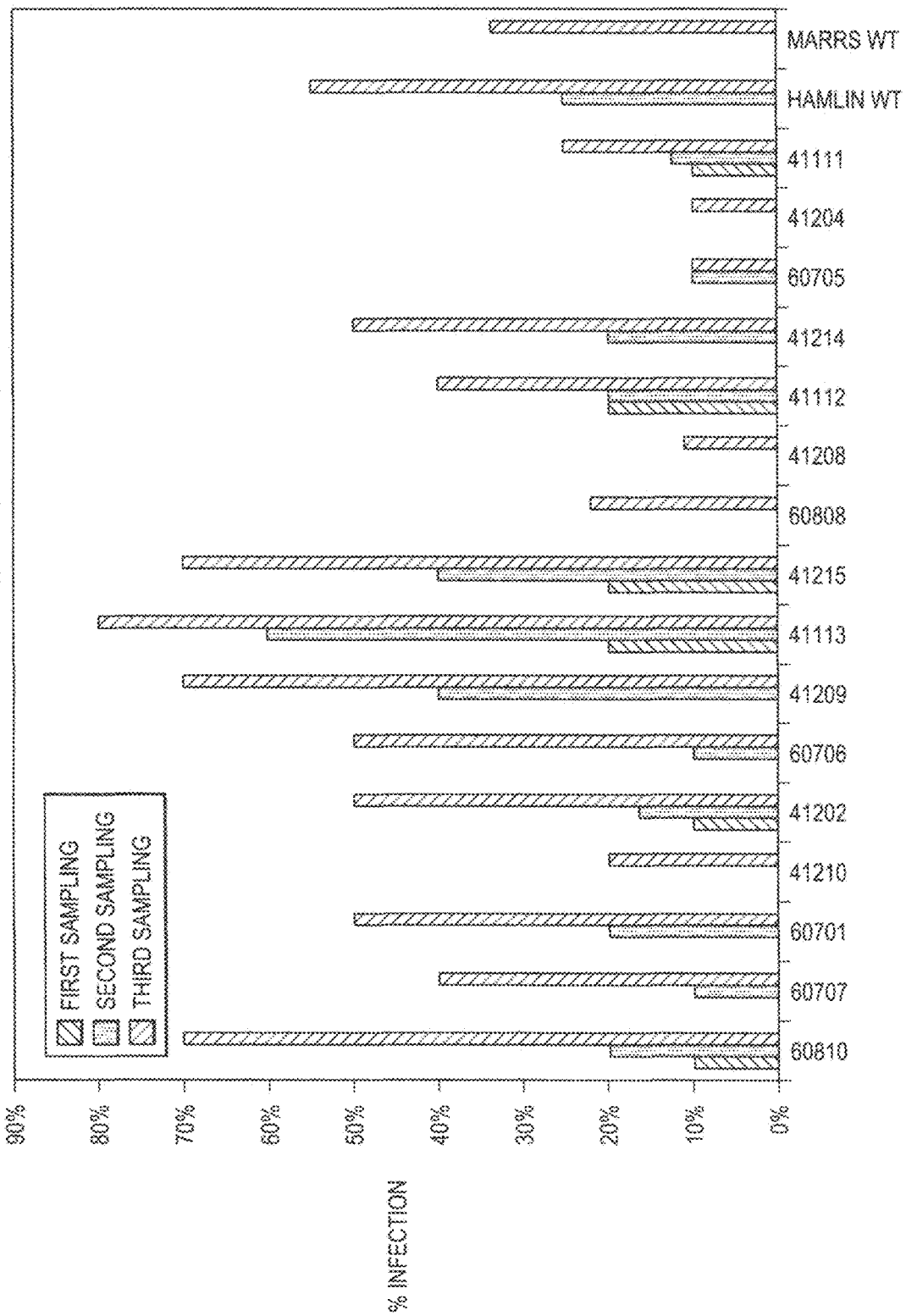

| | | | | | | |
|---|---|---|---|---|---|---|
| Genomic_D1 | 31 | SNC TSCRY–EG PAG–D KGIRR– | | | CLC CTHT– |
| Genomic_D2 | 54 | ANC TSCRY–EG PAG–D KGIRR– | | | CIC CTHA– |
| Genomic_D3 | 44 | SNC SICNT–EG PNG–E SGLRR– | | | CIC NTPCT |
| Genomic_D4 | 26 | RNC TNCNS–VK SGG–S QGFRR– | | | CMC TKPCA |
| Genomic_D5 | 44 | RNC NTCNS–ER SGG–E KGFRR– | | | CMC TGPCV |
| Genomic_D6 | 60 | SNC ANVCKN–EG PGG–R RGFRR– | | | CLC YKHCG |
| Genomic_D7 | 44 | RNC SSCMG–EG PGG–S HGFRR– | | | CVC SKPCA |
| Segura_D1 | 18 | RNC S | | | |
| Segura_D2 | 23 | SNC TSCRY–EG PAG–D KGIRR– | | | CMC SKPC– |
| Segura_D3 | 23 | ANC | | | |
| Segura_D4 | 23 | A | | | |
| Segura_D5 | 23 | AN | | | |
| Segura_D6 | 23 | XN | | | |
| Segura_D7 | 23 | SNC TSCRY–EG PAG–D | | | |
| Rs-AFP2_GroupI | 19 | NAC KNQ CIRLEKARHG–S CNYVFPAH | | | CIC YFPC– |
| At-AFP1_GroupI | 19 | NAC KNQ CINLEKARHG–S CNYVFPAH | | | CIC YFPC– |
| Hs-AFP1_GroupI | 21 | SKC SQQ CKDREH AYGA–C HYQFPSV | | | CKC KRQC– |
| Ah-AMP1_GroupII | 18 | AHC KQC QDWEKASHG–A CHKRENHW | | | CLC YFNC– |
| Dm-AMP1_GroupII | 18 | GHC NQC KSWEGAAHG–A CHVRNGKHM | | | CLC YFNC– |
| St-PTH1_GroupIII | 18 | SNC ASVCET–ER SGG–N HGFRR– | | | CTC TKPC– |
| Sialpha2_GroupIII | 18 | QNC AQVCLQ–EG GGG–N DGVMR–– | | | QCK IRQC– |
| consensus | 61 | . . . . . . |

FIG. 24B

|  | Def1 | Def2 | Def3 | Def4 | Def5 | Def6 | Def7 | SoD2 | SoD7 |
|---|---|---|---|---|---|---|---|---|---|
| Def1 |  | Def1+Def2 | Def1+Def3 | Def1+Def4 | Def1+Def5 | Def1+Def6 | Def1+Def7 | Def1+SoD2 | Def1+SoD7 |
| Def2 |  |  | Def2+Def3 | Def2+Def4 | Def2+Def5 | Def2+Def6 | Def2+Def7 | Def2+SoD2 | Def2+SoD7 |
| Def3 |  |  |  | Def3+Def4 | Def3+Def5 | Def3+Def6 | Def3+Def7 | Def3+SoD2 | Def3+SoD7 |
| Def4 |  |  |  |  | Def4+Def5 | Def4+Def6 | Def4+Def7 | Def4+SoD2 | Def4+SoD7 |
| Def5 |  |  |  |  |  | Def5+Def6 | Def5+Def7 | Def5+SoD2 | Def5+SoD7 |
| Def6 |  |  |  |  |  |  | Def6+Def7 | Def6+SoD2 | Def6+SoD7 |
| Def7 |  |  |  |  |  |  |  | Def7+SoD2 | Def7+SoD7 |
| SoD2 |  |  |  |  |  |  |  |  | SoD2+SoD7 |
| SoD7 |  |  |  |  |  |  |  |  |  |

FIG. 28

PATHOGEN RESISTANT CITRUS COMPOSITIONS, ORGANISMS, SYSTEMS, AND METHODS

CROSS-REFERENCE TO RELATED APPLICATIONS

This application claims priority to U.S. Application No. 62/192,732 filed Jul. 15, 2015, the entire contents of which are hereby incorporated in this disclosure by reference.

REFERENCE TO SEQUENCE LISTING SUBMITTED VIA EFS-WEB

This application includes an electronically submitted substitute sequence listing in .txt format. The .txt file contains a sequence listing entitled "2017-02-06_10003183-50235311_ST25.txt" created on Feb. 6, 2017 and is 134,559 bytes in size. The sequence listing contained in this .txt file is part of the specification and is hereby incorporated by reference herein in its entirety.

FIELD OF THE DISCLOSURE

The present disclosure relates, in some embodiments, to pathogen resistant citrus compositions, organisms, systems, and methods.

BACKGROUND OF THE DISCLOSURE

At present, there are no *Citrus* cultivars resistant to bacterial canker (*Xanthomonas axonopodis* pv. citri) (Xac), and/or citrus Huanglongbing (ex greening) caused by *Candidatus Liberibacter asiaticus* (Las). Indeed, no genetic resistance to these microbial pathogens has ever been found within the *Citrus* genus. Conventional cross-breeding efforts to produce resistant cultivars have been hindered by the complex reproductive biology and long life cycle of *Citrus* spp.

SUMMARY

Accordingly, a need has arisen for plants (e.g., citrus) with improved resistance to disease. A further need has arisen for improved methods, compositions, and systems for preparing genetically modified plants (e.g., citrus).

The present disclosure relates, according to some embodiments, to pathogen resistant citrus compositions, organisms, systems, and methods. For example, a composition may comprise a nucleic acid (e.g., a defensin nucleic acid). In some embodiments, a nucleic acid may comprise a nucleic acid sequence (a) having from about 75% to about 100% identity (e.g., about 98% identity) to a defensin sequence (e.g., SEQ ID NOS: 3, 4, 5, 6, 9, 10, 11, 12, 29, 46, 47, 48, 49, 50, 51, 52, 53, 54, 55, 56, 57, and/or 58) and/or (b) encoding an amino acid sequence having from about 95% to about 100% identity (e.g., 98% identity) to SEQ ID NOS: 1, 2, 7, 8, 28, 32, 33, 34, 35, 36, 37, and/or 38. A nucleic acid may comprise, in some embodiments, a nucleic acid sequence having about 98% identity to a sequence selected from the group consisting of SEQ ID NO: 3 and SEQ ID NO: 5 and encoding a peptide having an amino acid sequence having at least about 99% identity to SEQ ID NO: 1. A nucleic acid may comprise, in some embodiments, a nucleic acid sequence having about 98% identity to a sequence selected from the group consisting of SEQ ID NO: 4 and SEQ ID NO: 6 and encoding a peptide having an amino acid sequence having at least about 99% identity to SEQ ID NO: 2. According to some embodiments, a nucleic acid may comprise a nucleic acid sequence having about 98% identity to a sequence selected from the group consisting of SEQ ID NO: 9 and SEQ ID NO: 11 and encoding a peptide having an amino acid sequence having at least about 99% identity to SEQ ID NO: 7. A nucleic acid may comprise a nucleic acid sequence having about 98% identity to a sequence selected from the group consisting of SEQ ID NO: 10 and SEQ ID NO: 12 and encoding a peptide having an amino acid sequence having at least about 99% identity to SEQ ID NO: 8, in some embodiments. A nucleic acid may comprise, in some embodiments, a nucleic acid sequence having about 98% identity to a sequence selected from the group consisting of SEQ ID NO: 46 and SEQ ID NO: 52 and encoding a peptide having an amino acid sequence having at least about 99% identity to SEQ ID NO: 32. According to some embodiments, a nucleic acid may comprise a nucleic acid sequence having about 98% identity to a sequence selected from the group consisting of SEQ ID NO: 47 and SEQ ID NO: 53 and encoding a peptide having an amino acid sequence having at least about 99% identity to SEQ ID NO: 33. A nucleic acid may comprise, in some embodiments, a nucleic acid sequence having about 98% identity to a sequence selected from the group consisting of SEQ ID NO: 48 and SEQ ID NO: 54 and encoding a peptide having an amino acid sequence having at least about 99% identity to SEQ ID NO: 34. According to some embodiments, a nucleic acid may comprise a nucleic acid sequence having about 98% identity to a sequence selected from the group consisting of SEQ ID NO: 55 and encoding a peptide having an amino acid sequence having at least about 99% identity to SEQ ID NO: 35. A nucleic acid may comprise, in some embodiments, a nucleic acid sequence having about 98% identity to a sequence selected from the group consisting of SEQ ID NO: 49 and SEQ ID NO: 56 and encoding a peptide having an amino acid sequence having at least about 99% identity to SEQ ID NO: 36. According to some embodiments, a nucleic acid may comprise a nucleic acid sequence having about 98% identity to a sequence selected from the group consisting of SEQ ID NO: 50 and SEQ ID NO: 57 and encoding a peptide having an amino acid sequence having at least about 99% identity to SEQ ID NO: 37. A nucleic acid may comprise, in some embodiments, a nucleic acid sequence having about 98% identity to a sequence selected from the group consisting of SEQ ID NO: 51 and SEQ ID NO: 58 and encoding a peptide having an amino acid sequence having at least about 99% identity to SEQ ID NO: 38.

The present disclosure is related to nucleotide and amino acid sequences that are either (i) not found anywhere in nature or (ii) not found in nature in the organism into which they have been introduced. According to some embodiments, any nucleic acid sequence having less than 100% identity to a reference sequence shall differ from any naturally-occurring nucleic acid sequence of the same size by at least one nucleotide (e.g., by substitution, deletion, or insertion). Any amino acid sequence having less than 100% identity to a reference sequence shall differ from any naturally-occurring nucleic acid sequence of the same size by at least one amino acid (e.g., by substitution, deletion, or insertion).

The present disclosure relates, in some embodiments, to defensin expression vectors operable in citrus (e.g., citrus varieties, citrus rootstocks). For example, an expression vector may comprise, in a 5' to 3' direction, (a) an expression control sequence; (b) an expressible nucleic acid (e.g., a nucleic acid encoding an exogenous polypeptide) operably linked to the expression control sequence; and (c) a 3' termination sequence operably linked to the expressible nucleic acid. In some embodiments, an exogenous nucleic acid may comprise a nucleic acid sequence having at least about 75% identity (e.g., at least about 98% identity) to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 29, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. An expression vector may be located in a bacterial cell or a plant cell according to some embodiments. An expression vector may comprise, in some embodiments, the nucleotide sequence AACAATGG at positions −4 to 4 relative to a coding sequence (e.g., encoded by an exogenous nucleic acid sequence). According to some embodiments, an expression vector may comprise a linker (e.g., 3' of the expression control sequence and/or 5' of the nucleic acid (e.g., a nucleic acid encoding an exogenous polypeptide) having a length of from about 1 to about 200 nucleotides.

The present disclosure relates, in some embodiments, to a bacterial cell comprising an expression vector. For example, a bacterial cell may comprise an expression vector comprising, in a 5' to 3' direction, (a) an expression control sequence; (b) an expressible nucleic acid (e.g., a nucleic acid encoding an exogenous polypeptide) operably linked to the expression control sequence; and (c) a 3' termination sequence operably linked to the expressible nucleic acid. A bacterial cell may comprise, for example, an expression vector comprising, in a 5' to 3' direction, (a) an expression control sequence; (b) an exogenous nucleic acid operably linked to the expression control sequence; and/or (c) a 3' termination sequence operably linked to the exogenous nucleic acid, wherein the exogenous nucleic acid comprises a nucleic acid sequence having at least about 98% identity to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58.

The present disclosure relates, in some embodiments, to a plant cell (e.g., a citrus plant cell) comprising an expression vector. For example, a plant cell (e.g., a citrus plant cell) may comprise an expression vector comprising, in a 5' to 3' direction, (a) an expression control sequence; (b) an expressible nucleic acid (e.g., a nucleic acid encoding an exogenous polypeptide) operably linked to the expression control sequence; and (c) a 3' termination sequence operably linked to the expressible nucleic acid. A plant cell (e.g., a citrus plant cell) may comprise, for example, an expression vector comprising, in a 5' to 3' direction, (a) an expression control sequence; (b) an exogenous nucleic acid operably linked to the expression control sequence; and/or (c) a 3' termination sequence operably linked to the exogenous nucleic acid, wherein the exogenous nucleic acid comprises a nucleic acid sequence having at least about 98% identity to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 29, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. A plant cell (e.g., a citrus plant cell) may be located in a plant (e.g., a citrus plant) according to some embodiments. Examples of citrus plants include, without limitation, orange, grapefruit, lemon, and lime. A plant cell may comprise a defensin peptide. A defensin peptide may have, in some embodiments, an amino acid sequence having at least about 99% identity to SEQ ID NO: 1, SEQ ID NO: 2, SEQ ID NO: 7, SEQ ID NO: 8, SEQ ID NO: 28, SEQ ID NO: 32, SEQ ID NO: 33, SEQ ID NO: 34, SEQ ID NO: 35, SEQ ID NO: 36, SEQ ID NO: 37, or SEQ ID NO: 38 (e.g., encoded by and/or expressed from an expression vector nucleic acid) according to some embodiments.

In some embodiments, the present disclosure relates to a citrus plant (e.g., orange and/or grapefruit and/or lemon and/or lime) comprising an expression vector. A citrus plant may comprise an expression vector in a single cell, a plurality of cells (e.g., mosaic), or in all cells. A mosaic plant may arise from a graft in some embodiments. For example, a citrus plant may comprise a graft of a transgenic plant having an expression vector in all cells (e.g., scion) and a plant having a different expression vector or no expression vector in its cells (e.g., rootstock). A citrus plant may comprise, in some embodiments, in a single cell, a plurality of cells (e.g., mosaic), or in all cells a first expression vector (e.g., encoding a first defensin peptide) and in a single cell, a plurality of cells (e.g., mosaic), or in all cells a second expression vector (e.g., encoding a second defensin peptide). For example, a citrus plant cell may comprise (a) a first expression vector, the first expression vector comprising, in a 5' to 3' direction, (i) a first expression control sequence; (ii) a first exogenous nucleic acid operably linked to the first expression control sequence; and (iii) a first 3' termination sequence operably linked to the first exogenous nucleic acid, wherein the first exogenous nucleic acid comprises a nucleic acid sequence having at least about 98% identity to a nucleic acid sequence selected from the group consisting of SEQ ID NO: 3, SEQ ID NO: 5, SEQ ID NO: 9, SEQ ID NO: 11, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58; and (b) a second expression vector, the second expression vector comprising, in a 5' to 3' direction, (iv) a second expression control sequence; (v) a second exogenous nucleic acid operably linked to the second expression control sequence; and (vi) a second 3' termination sequence operably linked to the second exogenous nucleic acid, wherein the second exogenous nucleic acid comprises a nucleic acid sequence having at least about 98% identity to a nucleic acid sequence selected from the group consisting of SEQ ID NO: 4, SEQ ID NO: 6, SEQ ID NO: 10, and SEQ ID NO: 12, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. According to some embodiments, a citrus plant may comprise in a single cell, a plurality of cells (e.g., mosaic), or in all cells an expression vector comprising a first nucleic acid sequence encoding a first defensin peptide (e.g., a peptide having at least 99% identity to SEQ ID NO: 32, 33, 34, 35, 36, 37, or 38) and a second nucleic acid sequence encoding a second defensin peptide (e.g., a peptide having at least 99% identity to SEQ ID NO: 32, 33, 34, 35, 36, 37, or 38). In some embodiments, a citrus plant may comprise a defensin peptide in a single cell, a plurality of cells (e.g., mosaic), or in all cells. A citrus plant may comprise in a single cell, a plurality of cells (e.g., mosaic), or in all cells a first defensin peptide (e.g., a peptide having at least 99% identity to SEQ ID NO: 32, 33, 34, 35, 36, 37, or 38) and in a single cell, a plurality of cells (e.g., mosaic), or in all cells a second defensin peptide (e.g., a peptide having at least 99% identity to SEQ ID NO: 32, 33, 34, 35, 36, 37, or 38).

The present disclosure relates, in some embodiments, to methods of expressing in a citrus plant an exogenous nucleic acid comprising a nucleic acid sequence encoding an expressed peptide (e.g., a defensin peptide). For example, a method may comprise contacting an expression cassette comprising an exogenous nucleic acid or an expression vector comprising an exogenous nucleic acid with the cytosol of a cell of a citrus plant under conditions that permit expression of the exogenous nucleic acid and formation of the expressed peptide. In some embodiments, an exogenous nucleic acid may comprise a nucleic acid sequence having at least 98% identity to a nucleic acid sequence selected from SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 29, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. In some embodiments, an expression vector and/or an expression cassette may comprise, in a 5' to 3' direction, an expression control sequence, the exogenous nucleic acid operably linked to the expression control sequence, and a 3' termination sequence operably linked to the exogenous nucleic acid. An expressed peptide may comprise an amino acid sequence having at least 99% identity to an amino acid sequence selected from SEQ ID NO: 1, SEQ ID NO: 2, SEQ ID NO: 7, SEQ ID NO: 8, SEQ ID NO: 28, SEQ ID NO: 32, SEQ ID NO: 33, SEQ ID NO: 34, SEQ ID NO: 35, SEQ ID NO: 36, SEQ ID NO: 37, and/or SEQ ID NO: 38 according to some embodiments. Contacting an expression vector or cassette may further comprise, in some embodiments, co-cultivating the cell with an *Agrobacterium* cell comprising the expression vector or expression cassette to form a co-cultivated plant cell. According to some embodiments, a plant may be regenerated from a co-cultivated plant cell.

The present disclosure relates, in some embodiments, to methods for treating a citrus plant having and/or at risk of having a microbial infection (e.g., bacterial canker (*Xanthomonas axonopodis* pv. citri) (Xac), and/or citrus Huanglongbing (ex greening) caused by *Candidatus Liberibacter asiaticus* (Las)). For example, a method may comprise forming in the citrus plant at least one defensin peptide. Forming in the citrus plant at least one defensin peptide may comprise, in some embodiments, grafting the citrus plant with a cutting (e.g., a scion or a rootstock) from a second citrus plant, the second citrus plant comprising an expression vector and/or an expression cassette comprising, in a 5' to 3' direction, an expression control sequence, a defensin nucleic acid operably linked to the expression control sequence, and a 3' termination sequence operably linked to the defensin nucleic acid, wherein the defensin nucleic acid comprises a nucleic acid sequence encoding an amino acid sequence having at least 99% identity to an amino acid sequence selected from SEQ ID NO: 1, SEQ ID NO: 2, SEQ ID NO: 7, SEQ ID NO: 8, SEQ ID NO: 28, SEQ ID NO: 32, SEQ ID NO: 33, SEQ ID NO: 34, SEQ ID NO: 35, SEQ ID NO: 36, SEQ ID NO: 37, and/or SEQ ID NO: 38 under conditions that permit expression of the defensin nucleic acid.

The present disclosure relates, in some embodiments, to a citrus fruit (e.g., orange, grapefruit, lemon, lime) comprising at least one defensin peptide having the amino acid sequence of SEQ ID NO:87 or SEQ ID NO: 88.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein:

FIG. 15A illustrates the percentage of Generation 2 citrus plants infected upon the first, second, and third sampling of challenged material, according to specific example embodiments of the disclosure;

FIG. 15B is a continuation of the bar graph of FIG. 15A illustrating the percentage of Generation 2 citrus plants infected upon the first, second, and third sampling of challenged material, according to specific example embodiments of the disclosure;

FIG. 15C is a continuation of the bar graph of FIG. 15A illustrating the percentage of Generation 2 citrus plants infected upon the first, second, and third sampling of challenged material, according to specific example embodiments of the disclosure;

FIG. 16A illustrates the percentage of Generations 2 and 3 citrus plants infected upon the first, second and third samplings of challenged material, according to specific example embodiments of the disclosure;

FIG. 16B is a continuation of the bar graph of FIG. 16A illustrating the percentage of Generations 2 and 3 citrus plants infected upon the first, second and third samplings of challenged material, according to specific example embodiments of the disclosure;

FIG. 16C is a continuation of the bar graph of FIG. 16A illustrating the percentage of Generations 2 and 3 citrus plants infected upon the first, second and third samplings of challenged material, according to specific example embodiments of the disclosure.

FIG. 20 illustrates a multiple sequence alignment of Genomic D1 (SEQ ID NO: 32), Genomic D2 (SEQ ID NO: 33), Genomic D3 (SEQ ID NO: 34), Genomic D4 (SEQ ID NO: 35), Genomic D5 (SEQ ID NO: 36, Genomic D6 (SEQ ID NO: 37), and Genomic D7 (SEQ ID NO: 38) according to a specific example embodiment of the disclosure.

FIG. 22 illustrates the sequence alignments of Genomic D1 (SEQ ID NO: 32), Genomic D2 (SEQ ID NO: 33), Genomic D3 (SEQ ID NO: 34), Genomic D4 (SEQ ID NO: 35), Genomic D5 (SEQ ID NO: 36, Genomic D6 (SEQ ID NO: 37), and Genomic D7 (SEQ ID NO: 38), and Segura D1 (SEQ ID NO: 89), Segura D2 (SEQ ID NO: 90), Segura D3 (SEQ ID NO: 91), Segura D4 (SEQ ID NO: 92), Segura D5 (SEQ ID NO: 93), Segura D6 (SEQ ID NO: 94), and Segura D7 (SEQ ID NO: 95) according to a specific example embodiment of the disclosure.

FIG. 24A and FIG. 24B illustrates the sequence alignments of Genomic D1 (SEQ ID NO: 32), Genomic D2 (SEQ ID NO: 33), Genomic D3 (SEQ ID NO: 34), Genomic D4 (SEQ ID NO: 35), Genomic D5 (SEQ ID NO: 36, Genomic D6 (SEQ ID NO: 37), and Genomic D7 (SEQ ID NO: 38), as well as, representative group I defensin sequences Rs-AFP2 (SEQ ID NO: 96), At-AFP1 (SEQ ID NO: 97), and Hs-AFP1 (SEQ ID NO: 98) as illustrated in Segura et al.; representative group II defensin sequences Ah-Amp1 (SEQ ID NO:99) and Dm-Amp1 (SEQ ID NO: 100) as illustrated in Segura et al.; and representative group III defensin sequences St-PTH1 (SEQ ID NO: 101) and Siα2 (SEQ ID NO: 102 as illustrated in Segura et. al.) according to a specific example embodiment of the disclosure. FIG. 24A illustrates the more N-terminal portion of the alignment. FIG. 24B illustrates the more C-terminal portion of the alignment.

FIG. 28 illustrates the potential combinations for co-expression of spinach defensins, according to a specific example embodiment of the disclosure.

BRIEF DESCRIPTION OF THE SEQUENCE LISTING

Figure 1:
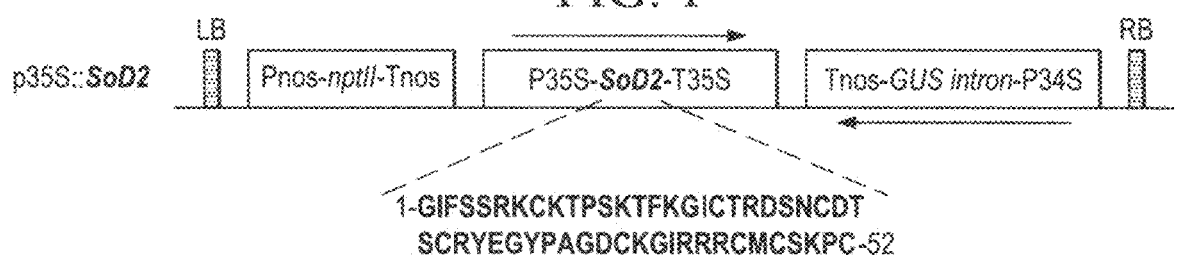
FIG. 1 illustrates an *Agrobacterium* transformation construct comprising a nucleic acid encoding SoD2 (SEQ ID NO: 1) according to specific example embodiments of the disclosure.

Some embodiments of the disclosure may be understood by referring, in part, to the present disclosure and the accompanying sequence listing, wherein:

SEQ ID NO: 1 illustrates an amino acid sequence of a spinach (*Spinacia oleracea*) defensin (SoD2) according to a specific example embodiment of the disclosure;

SEQ ID NO: 2 illustrates an amino acid sequence of a spinach (*Spinacia oleracea*) defensin (SoD7) according to a specific example embodiment of the disclosure;

SEQ ID NO: 3 illustrates a GenScript-optimized nucleic acid sequence for expression of a spinach (*Spinacia oleracea*) defensin (SoD2) according to a specific example embodiment of the disclosure;

SEQ ID NO: 4 illustrates a GenScript-optimized nucleic acid sequence for expression of a spinach (*Spinacia oleracea*) defensin (SoD7) according to a specific example embodiment of the disclosure;

SEQ ID NO: 5 illustrates a CODA-optimized nucleic acid sequence for expression of a spinach (*Spinacia oleracea*) defensin (SoD2) according to a specific example embodiment of the disclosure;

SEQ ID NO: 6 illustrates a CODA-optimized nucleic acid sequence for expression of a spinach (*Spinacia oleracea*) defensin (SoD7) according to a specific example embodiment of the disclosure;

SEQ ID NO: 7 illustrates an amino acid sequence of a chimeric peptide comprising a PR-1b signal peptide and a spinach (*Spinacia oleracea*) defensin (SoD2) according to a specific example embodiment of the disclosure;

SEQ ID NO: 8 illustrates an amino acid sequence of a chimeric peptide comprising a PR-1b signal peptide and a spinach (*Spinacia oleracea*) defensin (SoD7) according to a specific example embodiment of the disclosure;

SEQ ID NO: 9 illustrates a chimeric nucleic acid sequence comprising a nucleic acid sequence encoding a PR-1b signal peptide and a GenScript-optimized nucleic acid sequence for expression of a spinach (*Spinacia oleracea*) defensin (SoD2) according to a specific example embodiment of the disclosure;

SEQ ID NO: 10 illustrates a chimeric nucleic acid sequence comprising a nucleic acid sequence encoding a PR-1b signal peptide and a GenScript-optimized nucleic acid sequence for expression of a spinach (*Spinacia oleracea*) defensin (SoD7) according to a specific example embodiment of the disclosure;

SEQ ID NO: 11 illustrates a chimeric nucleic acid sequence comprising a nucleic acid sequence encoding a PR-1b signal peptide and a CODA-optimized nucleic acid sequence for expression of a spinach (*Spinacia oleracea*) defensin (SoD2) according to a specific example embodiment of the disclosure;

SEQ ID NO: 12 illustrates a chimeric nucleic acid sequence comprising a nucleic acid sequence encoding a PR-1b signal peptide and a CODA-optimized nucleic acid sequence for expression of a spinach (*Spinacia oleracea*) defensin (SoD7) according to a specific example embodiment of the disclosure;

SEQ ID NO: 13 illustrates an expression cassette comprising a nucleic acid sequence encoding a PR-1b signal peptide and a GenScript-optimized nucleic acid sequence for expression of a spinach (*Spinacia oleracea*) defensin (SoD2) according to a specific example embodiment of the disclosure;

SEQ ID NO: 14 illustrates an expression cassette comprising a nucleic acid sequence encoding a PR-1b signal peptide and a GenScript-optimized nucleic acid sequence for expression of a spinach (*Spinacia oleracea*) defensin (SoD7) according to a specific example embodiment of the disclosure;

SEQ ID NO: 15 illustrates an expression cassette comprising a nucleic acid sequence encoding a PR-1b signal peptide and a CODA-optimized nucleic acid sequence for expression of a spinach (*Spinacia oleracea*) defensin (SoD2) according to a specific example embodiment of the disclosure;

SEQ ID NO: 16 illustrates an expression cassette comprising a nucleic acid sequence encoding a PR-1b signal peptide and a CODA-optimized nucleic acid sequence for expression of a spinach (*Spinacia oleracea*) defensin (SoD7) according to a specific example embodiment of the disclosure;

SEQ ID NO: 17 illustrates an expression control sequence (CaMV 35S promoter) according to a specific example embodiment of the disclosure;

SEQ ID NO: 18 illustrates an untranslated region (TEV 5'UTR) according to a specific example embodiment of the disclosure;

SEQ ID NO: 19 illustrates an expression control sequence (CaMV 35S terminator) according to a specific example embodiment of the disclosure;

SEQ ID NO: 20 illustrates a nucleic acid sequence of a primer designated Zn5 according to a specific example embodiment of the disclosure;

SEQ ID NO: 21 illustrates a nucleic acid sequence of a primer designated Zn6 according to a specific example embodiment of the disclosure;

SEQ ID NO: 22 illustrates a nucleic acid sequence of a primer designated Fcp according to a specific example embodiment of the disclosure;

SEQ ID NO: 23 illustrates a nucleic acid sequence of a primer designated Rcp according to a specific example embodiment of the disclosure;

SEQ ID NO: 24 illustrates a nucleic acid sequence of a primer designated GUSF according to a specific example embodiment of the disclosure;

SEQ ID NO: 25 illustrates a nucleic acid sequence of a primer designated GUSR according to a specific example embodiment of the disclosure;

SEQ ID NO: 26 illustrates an amino acid sequence of a chimeric peptide comprising a modified PR-1b signal peptide and a GenScript-optimized nucleic acid sequence having a single deletion for expression of a spinach (*Spinacia oleracea*) defensin (SoD2) according to a specific example embodiment of the disclosure;

SEQ ID NO: 27 illustrates a chimeric nucleic acid sequence comprising a nucleic acid sequence encoding a modified PR-1b signal peptide and a GenScript-optimized nucleic acid sequence having a single deletion for expression of a spinach (*Spinacia oleracea*) defensin (SoD2) according to a specific example embodiment of the disclosure;

SEQ ID NO: 28 illustrates a core amino acid sequence of a defensin according to a specific example embodiment of the disclosure;

SEQ ID NO: 29 illustrates a nucleic acid sequence for expression of a core defensin according to a specific example embodiment of the disclosure;

SEQ ID NO: 30 illustrates a DNA 2.0-optimized nucleic acid sequence for expression of a spinach (*Spinacia oleracea*) defensin (SoD2) according to a specific example embodiment of the disclosure; and SEQ ID NO: 31 illustrates a DNA 2.0-optimized nucleic acid sequence for expression of a spinach (*Spinacia oleracea*) defensin (SoD7) according to a specific example embodiment of the disclosure.

SEQ ID NO: 32 illustrates an amino acid sequence of a spinach (*Spinacia oleracea*) defensin (Def1) according to a specific example embodiment of the disclosure;

SEQ ID NO: 33 illustrates an amino acid sequence of a spinach (*Spinacia oleracea*) defensin (Def2) according to a specific example embodiment of the disclosure;

SEQ ID NO: 34 illustrates an amino acid sequence of a spinach (*Spinacia oleracea*) defensin (Def3) according to a specific example embodiment of the disclosure;

SEQ ID NO: 35 illustrates an amino acid sequence of a spinach (*Spinacia oleracea*) defensin (Def4) according to a specific example embodiment of the disclosure;

SEQ ID NO: 36 illustrates an amino acid sequence of a spinach (*Spinacia oleracea*) defensin (Def5) according to a specific example embodiment of the disclosure;

SEQ ID NO: 37 illustrates an amino acid sequence of a spinach (*Spinacia oleracea*) defensin (Def6) according to a specific example embodiment of the disclosure;

SEQ ID NO: 38 illustrates an amino acid sequence of a spinach (*Spinacia oleracea*) defensin (Def 7) according to a specific example embodiment of the disclosure;

SEQ ID NO: 39 illustrates a nucleic acid sequence of a spinach (*Spinacia oleracea*) defensin (Def1) according to a specific example embodiment of the disclosure;

SEQ ID NO: 40 illustrates a nucleic acid sequence of a spinach (*Spinacia oleracea*) defensin (Def2) according to a specific example embodiment of the disclosure;

SEQ ID NO: 41 illustrates a nucleic acid sequence of a spinach (*Spinacia oleracea*) defensin (Def3) according to a specific example embodiment of the disclosure;

SEQ ID NO: 42 illustrates a nucleic acid sequence of a spinach (*Spinacia oleracea*) defensin (Def4) according to a specific example embodiment of the disclosure;

SEQ ID NO: 43 illustrates a nucleic acid sequence of a spinach (*Spinacia oleracea*) defensin (Def5) according to a specific example embodiment of the disclosure;

SEQ ID NO: 44 illustrates a nucleic acid sequence of a spinach (*Spinacia oleracea*) defensin (Def6) according to a specific example embodiment of the disclosure;

SEQ ID NO: 45 illustrates a nucleic acid sequence of a spinach (*Spinacia oleracea*) defensin (Def7) according to a specific example embodiment of the disclosure;

SEQ ID NO: 46 illustrates a GenScript-optimized nucleic acid sequence for expression of a spinach (*Spinacia oleracea*) defensin (Def1) according to a specific example embodiment of the disclosure;

SEQ ID NO: 47 illustrates a GenScript-optimized nucleic acid sequence for expression of a spinach (*Spinacia oleracea*) defensin (Def2) according to a specific example embodiment of the disclosure;

SEQ ID NO: 48 illustrates a GenScript-optimized nucleic acid sequence for expression of a spinach (*Spinacia oleracea*) defensin (Def3) according to a specific example embodiment of the disclosure;

SEQ ID NO: 49 illustrates a GenScript-optimized nucleic acid sequence for expression of a spinach (*Spinacia oleracea*) defensin (Def5) according to a specific example embodiment of the disclosure;

SEQ ID NO: 50 illustrates a GenScript-optimized nucleic acid sequence for expression of a spinach (*Spinacia oleracea*) defensin (Def6) according to a specific example embodiment of the disclosure;

SEQ ID NO: 51 illustrates a GenScript-optimized nucleic acid sequence for expression of a spinach (*Spinacia oleracea*) defensin (Def7) according to a specific example embodiment of the disclosure;

SEQ ID NO: 52 illustrates a VGD-optimized nucleic acid sequence for expression of a spinach (*Spinacia oleracea*) defensin (Def1) according to a specific example embodiment of the disclosure;

SEQ ID NO: 53 illustrates a VGD-optimized nucleic acid sequence for expression of a spinach (*Spinacia oleracea*) defensin (Deft) according to a specific example embodiment of the disclosure;

SEQ ID NO: 54 illustrates a VGD-optimized nucleic acid sequence for expression of a spinach (*Spinacia oleracea*) defensin (Def3) according to a specific example embodiment of the disclosure;

SEQ ID NO: 55 illustrates a VGD-optimized nucleic acid sequence for expression of a spinach (*Spinacia oleracea*) defensin (Def4) according to a specific example embodiment of the disclosure;

SEQ ID NO: 56 illustrates a VGD-optimized nucleic acid sequence for expression of a spinach (*Spinacia oleracea*) defensin (Def5) according to a specific example embodiment of the disclosure;

SEQ ID NO: 57 illustrates a VGD-optimized nucleic acid sequence for expression of a spinach (*Spinacia oleracea*) defensin (Def6) according to a specific example embodiment of the disclosure;

SEQ ID NO: 58 illustrates a VGD-optimized nucleic acid sequence for expression of a spinach (*Spinacia oleracea*) defensin (Def7) according to a specific example embodiment of the disclosure;

SEQ ID NO: 59 illustrates a chimeric nucleic acid sequence comprising a nucleic acid sequence encoding a spinach (*Spinacia oleracea*) defensin (Def2) signal peptide and a GenScript-optimized nucleic acid sequence for expression of a spinach (*Spinacia oleracea*) defensin (Def2) according to a specific example embodiment of the disclosure;

SEQ ID NO: 60 illustrates a chimeric nucleic acid sequence comprising a nucleic acid sequence encoding a spinach (*Spinacia oleracea*) defensin (Def2) signal peptide and a VGD-optimized nucleic acid sequence for expression of a spinach (*Spinacia oleracea*) defensin (Def2) according to a specific example embodiment of the disclosure;

SEQ ID NO: 61 illustrates an expression cassette comprising a nucleic acid sequence encoding a GenScript-optimized nucleic acid sequence for expression of a spinach (*Spinacia oleracea*) defensin (Def1) according to a specific example embodiment of the disclosure;

SEQ ID NO: 62 illustrates an expression cassette comprising a nucleic acid sequence encoding a GenScript-optimized nucleic acid sequence for expression of a spinach (*Spinacia oleracea*) defensin (Def2) according to a specific example embodiment of the disclosure;

SEQ ID NO: 63 illustrates an expression cassette comprising a nucleic acid sequence encoding a GenScript-optimized nucleic acid sequence for expression of a spinach (*Spinacia oleracea*) defensin (Def3) according to a specific example embodiment of the disclosure;

SEQ ID NO: 64 illustrates an expression cassette comprising a nucleic acid sequence encoding a GenScript-optimized nucleic acid sequence for expression of a spinach (*Spinacia oleracea*) defensin (Def5) according to a specific example embodiment of the disclosure;

SEQ ID NO: 65 illustrates an expression cassette comprising a nucleic acid sequence encoding a GenScript-optimized nucleic acid sequence for expression of a spinach (*Spinacia oleracea*) defensin (Def6) according to a specific example embodiment of the disclosure;

SEQ ID NO: 66 illustrates an expression cassette comprising a nucleic acid sequence encoding a GenScript-optimized nucleic acid sequence for expression of a spinach (*Spinacia oleracea*) defensin (Def7) according to a specific example embodiment of the disclosure;

SEQ ID NO: 67 illustrates an expression cassette comprising a nucleic acid sequence encoding a VGD-optimized nucleic acid sequence for expression of a spinach (*Spinacia oleracea*) defensin (Def1) according to a specific example embodiment of the disclosure;

SEQ ID NO: 68 illustrates an expression cassette comprising a nucleic acid sequence encoding a VGD-optimized nucleic acid sequence for expression of a spinach (*Spinacia oleracea*) defensin (Def2) according to a specific example embodiment of the disclosure;

SEQ ID NO: 69 illustrates an expression cassette comprising a nucleic acid sequence encoding a VGD-optimized nucleic acid sequence for expression of a spinach (*Spinacia oleracea*) defensin (Def3) according to a specific example embodiment of the disclosure;

SEQ ID NO: 70 illustrates an expression cassette comprising a nucleic acid sequence encoding a VGD-optimized nucleic acid sequence for expression of a spinach (*Spinacia oleracea*) defensin (Def4) according to a specific example embodiment of the disclosure;

SEQ ID NO: 71 illustrates an expression cassette comprising a nucleic acid sequence encoding a VGD-optimized nucleic acid sequence for expression of a spinach (*Spinacia oleracea*) defensin (Def5) according to a specific example embodiment of the disclosure;

SEQ ID NO: 72 illustrates an expression cassette comprising a nucleic acid sequence encoding a VGD-optimized nucleic acid sequence for expression of a spinach (*Spinacia oleracea*) defensin (Def6) according to a specific example embodiment of the disclosure;

SEQ ID NO: 73 illustrates an expression cassette comprising a nucleic acid sequence encoding a VGD-optimized nucleic acid sequence for expression of a spinach (*Spinacia oleracea*) defensin (Def7) according to a specific example embodiment of the disclosure;

SEQ ID NO: 74 illustrates an expression control sequence (CaMV 35S promoter) according to a specific example embodiment of the disclosure;

SEQ ID NO: 75 illustrates an untranslated region (TEV 5'UTR) according to a specific example embodiment of the disclosure;

SEQ ID NO: 76 illustrates an untranslated region (TEV 3'UTR) according to a specific example embodiment of the disclosure;

SEQ ID NO: 77 illustrates an terminator sequence (CaMV 35S terminator) according to a specific example embodiment of the disclosure;

SEQ ID NO: 78 illustrates a promoter sequence (PHT4; 6 *Arabidopsis thaliana* promoter) according to a specific example embodiment of the disclosure;

SEQ ID NO: 79 illustrates a promoter sequence (PHT4; 2 *Arabidopsis thaliana* promoter) according to a specific example embodiment of the disclosure; SEQ ID NO: 80 illustrates a promoter sequence (TPS-Cin *Arabidopsis thaliana* promoter) according to a specific example embodiment of the disclosure.

SEQ ID NO: 81 illustrates an assembled scaffold sequence of spinach (*Spinacia oleracea*) according to a specific example embodiment of the disclosure.

SEQ ID NO: 82 illustrates an assembled scaffold sequence of spinach (*Spinacia oleracea*) according to a specific example embodiment of the disclosure.

SEQ ID NO: 83 illustrates an assembled scaffold sequence of spinach (*Spinacia oleracea*) according to a specific example embodiment of the disclosure.

SEQ ID NO: 84 illustrates an assembled scaffold sequence of spinach (*Spinacia oleracea*) according to a specific example embodiment of the disclosure.

SEQ ID NO: 85 illustrates an assembled scaffold sequence of spinach (*Spinacia oleracea*) according to a specific example embodiment of the disclosure.

SEQ ID NO: 86 illustrates an assembled scaffold sequence of spinach (*Spinacia oleracea*) according to a specific example embodiment of the disclosure.

SEQ ID NO: 87 illustrates an amino acid sequence of a spinach (*Spinacia oleracea*) defensin peptide according to a specific example embodiment of the disclosure.

SEQ ID NO: 88 illustrates an amino acid sequence of a spinach (*Spinacia oleracea*) defensin peptide according to a specific example embodiment of the disclosure.

DETAILED DESCRIPTION

The present disclosure relates, in some embodiments, to compositions, organisms, systems, and methods for enhancing a plant's innate ability, if any, to respond to contact (e.g., infection) with a pathogen (e.g., bacteria, yeast, fungus, virus). In some embodiments, the present disclosure relates to compositions, organisms, systems, and methods for expressing a gene product (e.g., an antimicrobial peptide) in a plant (e.g., citrus). For example, the present disclosure relates to expression control sequences (e.g., promoters), expression cassettes, expression vectors, microorganisms, and/or plants comprising one or more antimicrobial peptides and/or one or more nucleic acids encoding one or more antimicrobial peptides.

I. Compositions

A. Antimicrobial Peptides

The present disclosure relates, according to some embodiments, to peptides and/or proteins having insecticidal activity, antimicrobial activity, and/or antiviral activity, which may include, without limitation, avidin, vegetative insecticidal proteins (e.g., Vip3A), insecticidal crystal proteins from *Bacillus thuringiensis* (e.g., Cry1, Cry1Ab, Cry2, Cry9), pea albumin (e.g., PA1b), hirsutellin A, lectins (e.g., snow drop lily lectin, garlic lectin, onion lectin), amylase inhibitors (e.g., alpha amylase inhibitor), arcelins (e.g., arcelins from beans), proteinase inhibitors, lysozymes (e.g., bovine lysozyme, human lysozyme, mollusk lysozyme), defensin (e.g., SoD2, SoD7, Def1, Def2, Def3, Def4, Def5, Def6, and/or Def7), chitinase, β-1,3-glucanase, variants thereof, and/or combinations thereof. An antimicrobial peptide may comprise, for example, one or more antimicrobial-peptides belonging to the family of plant defensins. These polypeptides were originally isolated from spinach leaves (*Spinacia oleracea*). In some embodiments, a defensin may be small (about 5 kDa), may be basic and/or may be cysteine-rich. In some embodiments, a defensin may comprise a peptide having an amino acid sequence sharing at least about 95% identity, at least about 96% identity, at least about 97% identity, at least about 98% identity, at least about 99% identity, and/or about 100% identity with SEQ ID NO: 1, SEQ ID NO: 2, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 87, and/or SEQ ID NO: 88. In some embodiments, an antimicrobial peptide may further comprise one or more amino acids that are independently and/or collectively either neutral (e.g., do not adversely impact antibacterial functionality) and/or augment antibacterial functionality (e.g., by directing the peptide to a desired location (e.g., cellular and/or extracellular). For example, a defensin may comprise a signal peptide derived from the tobacco pathogenesis-related (PR)-1b protein that allows the transport of the peptides into the apoplast of plant cells (e.g., via the secretory pathway) and/or accumulation in the intercellular spaces of leaves, stems, flowers, fruits, seeds, and/or roots. A defensin may comprise, according to some embodiments, a peptide having an amino acid sequence sharing at least about 95% identity, at least about 96% identity, at least about 97% identity, at least about 98% identity, at least about 99% identity, and/or about 100% identity with SEQ ID NO: 1, SEQ ID NO: 2, SEQ ID NO: 7, SEQ ID NO: 8; SEQ ID NO: 28, SEQ ID NO: 32, SEQ ID NO: 33, SEQ ID NO: 34, SEQ ID NO: 35, SEQ ID NO: 36, SEQ ID NO: 37, and/or SEQ ID NO: 38. Differences in peptide sequences among defensins may give rise to qualitative and/or quantitative differences in performance relative to one or more other defensins. For example, Def3, Def4, Def5, Def6, and/or Def7 (e.g., peptides having the sequence of SEQ ID NO: 34, 35, 36, 37, or 38) may perform differently than one or more other defensins within a plant cell or a plant tissue (e.g., increases or decreases in mobility, insecticidal activity, antimicrobial activity, susceptibility to processing and/or subcellular targeting, accumulation, peptide stability, degradation, and/or longevity as compared to other defensin peptides).

B. Nucleic Acids

The present disclosure relates, in some embodiments, to nucleic acids (e.g., cassettes, vectors) comprising one or more sequences encoding one or more antimicrobial peptides. For example, a nucleic acid may comprise a cassette comprising a synthetic or artificial defensin nucleic acid sequence (e.g. nucleic acid sequences SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, and/or SEQ ID NO: 73). A synthetic or artificial defensin nucleic acid may encode the same amino acid sequence as a native spinach defensin with codons modified (e.g., optimized) from the native nucleotide sequence for citrus codon usage. A nucleic acid comprising a defensin coding sequence may comprise a sequence encoding a signal peptide (e.g., SEQ ID NO: 59, SEQ ID NO: 60). In some embodiments, expression of a nucleic acid comprising a sequence encoding an antimicrobial peptide may be optimized by positioning an initiation codon in a favorable (e.g., optimal) 5' context. According to some embodiments, a nucleic acid may comprise an expression control sequence (e.g., operably linked to a coding sequence). For example, a nucleic acid may comprise a coding gene sequence under the control of a dual enhanced CaMV 35S promoter with a 5' UTR from TEV plant potyvirus (e.g., to provide a translation-enhancing activity to the defensin genes).

According to some embodiments, a nucleic acid may comprise a nucleotide sequence having at least about 75% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 80% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 85% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 90% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 95% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 97% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 98% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 99% identity to SEQ ID NOS: 3, 4, 5, 6, 9, 10, 11, 12, 29, 30, 31, 46, 47, 48, 49, 50, 51, 52, 53, 54, 55, 56, 57, and/or 58; and/or about 100% identity to SEQ ID NOS: 3, 4, 5, 6, 9, 10, 11, 12, 29, 30, 31, 46, 47, 48, 49, 50, 51, 52, 53, 54, 55, 56, 57, and/or 58. A nucleotide sequence may encode, in some embodiments, an amino acid sequence having at least about 98% identity to SEQ ID NOS: 1, 2, 7, 8, 28, 32, 33, 34, 35, 36, 37, and/or 38, at least about 99% identity to SEQ ID NOS: 1, 2, 7, 8, 28, 32, 33, 34, 35, 36, 37, and/or 38, and/or about 100% identity to SEQ ID NOS: 1, 2, 7, 8, 28, 32, 33, 34, 35, 36, 37, and/or 38. According to some embodiments, a nucleic acid may have a first measure of sequence identity to a reference nucleic acid sequence and may encode an amino acid sequence having a second measure of sequence identity to a reference amino acid sequence. For example, a nucleic acid may have about 85% identity to SEQ ID NOS: 3, 4, 5, 6, 9, 10, 11, 12, 29, 30, 31, 46, 47, 48, 49, 50, 51, 52, 53, 54, 55, 56, 57, and/or 58, and encode an amino acid sequence having about 100% identity with SEQ ID NOS: 1, 2, 7, 8, 28, 32, 33, 34, 35, 36, 37, and/or 38, according to some embodiments.

A nucleic acid sequence, according to some embodiments, may hybridize to a nucleic acid having the nucleotide sequence of SEQ ID NOS: 3, 4, 5, 6, 9, 10, 11, 12, 29, 30, 31, 46, 47, 48, 49, 50, 51, 52, 53, 54, 55, 56, 57, and/or 58 under stringent conditions. Stringent conditions may include, for example, (a) 4×SSC at 65° C. followed by 0.1×SSC at 65° for 60 minutes and/or (b) 50% formamide, 4×SSC at 65° C. A nucleic acid may comprise a deletion fragment (e.g., a deletion of from about 1 to about 12 bases) of a nucleic acid having a sequence of SEQ ID NOS: 3, 4, 5, 6, 9, 10, 11, 12, 29, 30, 31, 46, 47, 48, 49, 50, 51, 52, 53, 54, 55, 56, 57, and/or 58 that retains antimicrobial activity against at least one microorganism capable of infecting a citrus plant. One of ordinary skill in the art having the benefit of the present disclosure may prepare one or more deletion fragments of a nucleic acid having a sequence of SEQ ID NOS: 3, 4, 5, 6, 9, 10, 11, 12, 29, 30, 31, 46, 47, 48, 49, 50, 51, 52, 53, 54, 55, 56, 57, and/or 58 and screen the resulting fragments for antimicrobial activity against at least one microorganism capable of infecting a citrus plant.

A nucleic acid sequence having a sequence like SEQ ID NOS: 3, 4, 5, 6, 30, 31, 46, 47, 48, 49, 50, 51, 52, 53, 54, 55, 56, 57, and/or 58 may be identified by database searches using the sequence or elements thereof as the query sequence using the Gapped BLAST algorithm (Altschul et al., 1997 *Nucl. Acids Res.* 25:3389-3402) with the BLOSUM62 Matrix, a gap cost of 11 and persistence cost of 1 per residue and an E value of 10. Sequence identity may be assessed by any available method according to some embodiments. For example, two sequences may be compared with either ALIGN (Global alignment) or LALIGN (Local homology alignment) in the FASTA suite of applications (Pearson and Lipman, 1988 *Proc. Nat. Acad. Sci.* 85:2444-2448; Pearson, 1990 *Methods in Enzymology* 183: 63-98) with the BLOSUM50 matrix and gap penalties of −16, −4. Sequence similarity may be assessed according to ClustalW (Larkin et al., 2007, *Bioinformatics* 23(21): 2947-2948), BLAST, FASTA or similar algorithm.

C. Expression Cassettes and Vectors

The disclosure relates, in some embodiments, to expression vectors and/or expression cassettes for expressing a nucleic acid sequence (e.g., a coding sequence) in a cell and comprising an expression control sequence and the nucleic acid sequence operably linked to the expression control sequence. Thus, for example, an expression cassette may comprise a heterologous coding sequence, the expression of which may be desired in a plant.

1. Expression Vectors

The disclosure relates, in some embodiments, to an expression vector which may comprise, for example, a nucleic acid having an expression control sequence and a coding sequence operably linked to the expression control sequence. In some embodiments, an expression control sequence may comprise one or more promoters, one or more operators, one or more enhancers, one or more ribosome binding sites, and/or combinations thereof. An expression control sequence may comprise, for example, a nucleic acid having promoter activity. An expression control sequence, according to some embodiments, may be constitutively active or conditionally active in (a) an organ selected from root, leaf, stem, flower, seed, and/or fruit, and/or (b) active in a tissue selected from epidermis, periderm, parenchyma, collenchyma, sclerenchyma, xylem, phloem, and/or secretory structures. An expression control sequence, according to some embodiments, may be operable to drive expression of a nucleic acid sequence (e.g., a coding sequence) in a cell. Metrics for expression may include, for example, rate of appearance and/or accumulation of a gene product (e.g., RNA and/or protein) and/or total accumulation of a gene product as of one or more time points (e.g., elapsed time after a starting point and/or a stage of development). Comparative assays for gene products may be qualitative, semi-quantitative, and/or quantitative in some embodiments. Comparative assays may indirectly and/or directly assess the presence and/or amount of gene product. In some embodiments, an expression control sequence may be sensitive to one or more stimuli (e.g., one or more small molecules, one or more plant defense-inducing agents, mechanical damage, temperature, pressure). For example, activity of an expression control sequence may be enhanced or suppressed upon infection with a microorganism (e.g., a bacteria or a virus).

Figure 2:
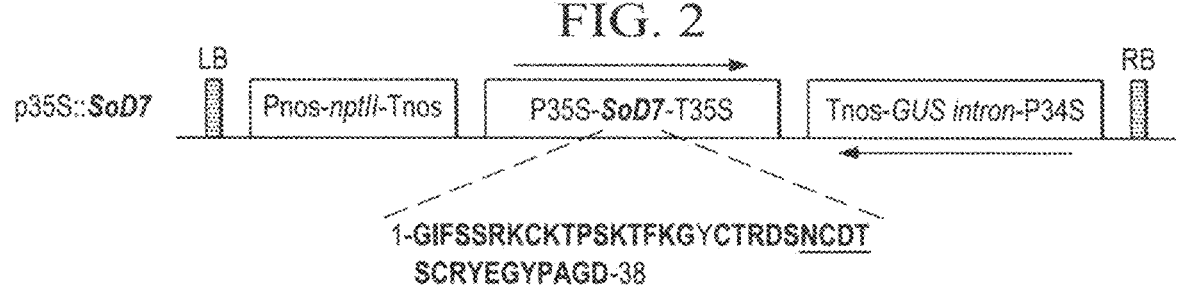
FIG. 2 illustrates an *Agrobacterium* transformation construct comprising a nucleic acid encoding SoD7 (SEQ ID NO: 2) according to specific example embodiments of the disclosure.

An expression vector may be contacted with a cell (e.g., a plant cell) under conditions that permit expression (e.g., transcription) of the coding sequence. Examples of expression vectors may include the *Agrobacterium* transformation constructs shown in FIG. 1 and FIG. 2. An expression control sequence may be contacted with a plant cell (e.g., an embryonic cell, a stem cell, a callous cell) under conditions that permit expression of the coding sequence in the cell and/or cells derived from the plant cell according to some embodiments. An expression vector may be contacted with a cell (e.g., a plant cell), in some embodiments, under conditions that permit inheritance of at least a portion of the expression vector in the cell's progeny. According to some embodiments, an expression vector may include one or more selectable markers. For example, an expression vector may include a marker for selection when the vector is in a bacterial host, a yeast host, and/or a plant host.

2. Expression Cassettes

According to some embodiments, the disclosure relates to an expression cassette which may comprise, for example, a nucleic acid having an expression control sequence and a coding sequence operably linked to the expression control sequence. An expression cassette may be comprised in an expression vector. A coding sequence, in some embodiments, may comprise any coding sequence expressible in at least one plant cell. For example, a coding sequence may comprise a plant sequence, a yeast sequence, a bacterial sequence, a viral sequence (e.g., plant virus), an artificial sequence, an antisense sequence thereof, a fragment thereof, a variant thereof, and/or combinations thereof. A coding sequence may comprise, in some embodiments, a sequence encoding one or more gene products with insecticidal, antibacterial, antifungal, antimicrobial, and/or antiviral activity. A coding sequence may comprise, in some embodiments, a start codon, an intron, and/or a translation termination sequence. According to some embodiments, a coding sequence may comprise one or more natural or artificial coding sequences (e.g., encoding a single protein or a chimera). According to some embodiments, an expression cassette may optionally comprise a termination sequence. A coding sequence, in some embodiments, may comprise a sequence at least partially codon optimized for expression in an organism of interest (e.g., a citrus plant).

An expression control sequence may be used, in some embodiments, to construct an expression cassette comprising, in the 5' to 3' direction, (a) the expression control sequence, (b) a heterologous gene or a coding sequence, or sequence complementary to a native plant gene under control of the expression control sequence, and/or (c) a 3' termination sequence (e.g., a termination sequence comprising a polyadenylation site). Examples of expression cassettes may include, in some embodiments, the cassettes shown in SEQ ID NOS: 13-16 and SEQ ID NOS: 61-73. An expression cassette may be incorporated into a variety of autonomously replicating vectors in order to construct an expression vector. An expression cassette may be constructed, for example, by ligating an expression control sequence to a sequence to be expressed (e.g., a coding sequence).

Some techniques for construction of expression cassettes are well known to those of ordinary skill in the art. For example, a variety of strategies are available for ligating fragments of DNA, the choice of which depends on the nature of the termini of the DNA fragments. An artisan of ordinary skill having the benefit of the present disclosure, a coding sequence (e.g., having antimicrobial activity) and/or portions thereof may be provided by other means, for example chemical or enzymatic synthesis. A nucleic acid may comprise, in a 5' to 3' direction, an expression control sequence, a linker (optional), and a coding sequence according to some embodiments. A nucleic acid may comprise, in some embodiments, one or more restriction sites and/or junction sites between an expression control sequence, a linker, and/or a coding sequence.

II. Microorganisms

The present disclosure relates, in some embodiments, to a microorganism comprising an antimicrobial peptide (e.g., a heterologous antimicrobial peptide) and/or a nucleic acid (e.g., a heterologous and/or expressible nucleic acid) comprising a nucleic acid sequence encoding an antimicrobial peptide. For example, a microorganism may comprise a bacteria, a yeast, and/or a virus. Examples of microorganisms may include, without limitation, *Agrobacterium tumefaciens*, *Escherichia coli*, a lepidopteran cell line, a Rice tungro bacilliform virus, a Commelina yellow mosaic virus, a Banana streak virus, a Taro bacilliform virus, and/or baculovirus. According to some embodiments, an antimicrobial peptide may be tolerated by and/or innocuous to its host microorganism. A microorganism may comprise an expression control sequence and an antimicrobial peptide coding sequence operably linked to the expression control sequence. A nucleic acid (e.g., a heterologous and/or expressible nucleic acid) comprising a nucleic acid sequence encoding an antimicrobial peptide may be present, in some embodiments, on a genomic nucleic acid and/or an extra-genomic nucleic acid.

III. Plants

The present disclosure relates, in some embodiments, to a plant cell (e.g., an embryonic cell, a stem cell, a callous cell), a tissue, and/or a plant comprising an antimicrobial peptide (e.g., a heterologous antimicrobial peptide) and/or a nucleic acid (e.g., a heterologous and/or expressible nucleic acid) comprising a nucleic acid sequence encoding an antimicrobial peptide. A plant and/or plant cell may be a dicot in some embodiments. Examples of a dicot may include, without limitation, coffee, tomato, pepper, tobacco, lima bean, *Arabidopsis*, rubber, orange, grapefruit, lemon, lime, tangerine, mandarin, pummelo, potato, squash, peas, and/or sugar beet. A plant cell may be included in a plant tissue, a plant organ, and/or a whole plant in some embodiments. A plant cell in a tissue, organ, and/or whole plant may be adjacent, according to some embodiments, to one or more isogenic cells and/or one or more heterogenic cells. In some embodiments, a plant may include primary transformants and/or progeny thereof. A plant comprising a nucleic acid (e.g., a heterologous and/or expressible nucleic acid) comprising a nucleic acid sequence encoding an antimicrobial peptide may further comprise an expression control sequence operably linked to the nucleic acid, in some embodiments. A nucleic acid sequence encoding an antimicrobial peptide may be expressed, according to some embodiments, in a plant in one or more up to all (e.g., substantially all) organs, tissues, and/or cell types including, without limitation, stalks, leaves, roots, seeds, flowers, fruit, meristem, parenchyma, storage parenchyma, collenchyma, sclerenchyma, epidermis, mesophyll, bundle sheath, guard cells, protoxylem, metaxylem, phloem, phloem companion, and/or combinations thereof. In some embodiments, a nucleic acid and/or its gene product (e.g., an antimicrobial peptide) may be located in and/or translocated to one or more organelles (e.g., vacuoles, chloroplasts, mitochondria, plastids).

IV. Methods

A. Transforming a Plant

The present disclosure relates, according to some embodiments, to methods for independent transformation of citrus (e.g., a native genome of a citrus plant). For example, a method may comprise independent transformation, using *Agrobacterium tumefaciens* (At), of the native genome of the orange (*Citrus sinensis*) cultivars "Rhode Red", "Hamlin", and/or "Marrs." A transformation method may comprise contacting a nucleic acid comprising a SoD2, SoD7, and/or another defensin sequence (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58) with a citrus plant according to some embodiments. A transformed plant (e.g., a transformed genome of a new orange cultivar) may independently contain, in some embodiments a sequence of a SoD2 gene, a SoD7 gene, and/or another defensin (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58) encoding microbial resistance not found within the native gene pool of the *Citrus* genus. According to some embodiments, a transformed orange cultivar plant may comprise a peptide encoded by a SoD2 gene, a SoD7 gene, and/or another defensin gene (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58). A transformed plant comprising a sequence of a SoD2 gene, a SoD7 gene, and/or another defensin gene (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58) and/or comprising a peptide encoded by a SoD2 gene, a SoD7 gene, and/or another defensin gene (e.g. SEQ ID NO: 32, SEQ ID NO. 33, SEQ ID NO: 34, SEQ ID NO: 35, SEQ ID NO: 36, SEQ ID NO: 37, SEQ ID NO: 38, SEQ ID NO: 86, and/or SEQ ID NO: 87) may display resistance to a range (e.g., a broad range) of bacterial and/or fungal pathogens in some embodiments. For example, a transformed plant comprising a sequence of a SoD2 gene and/or a SoD7 gene and/or comprising a peptide encoded by a SoD2 gene and/or a SoD7 gene may display resistance to bacterial canker (*Xanthomonas axonopodis* pv. citri) (Xac), and/or citrus Huanglongbing (ex greening) caused by *Candidatus Liberibacter asiaticus* (Las). See EXAMPLE section below.

B. Grafting

The present disclosure relates to grafting at least a portion of a first plant (e.g., a citrus plant) with at least a portion of a second plant (e.g., a citrus plant), according to some embodiments. A first plant may be in any desired condition including, without limitation, a healthy condition, a diseased condition, an injured condition, a stressed condition (e.g., heat, cold, water, and the like), and/or combinations thereof. A first plant may have any desired genotype including, without limitation, wild type, transgenic, mutant, and/or the like with respect to a gene and/or trait of interest.

A second plant may be in any desired condition including, without limitation, a healthy condition, a diseased condition, an injured condition, a stressed condition (e.g., heat, cold, water, and the like), and/or combinations thereof. A second plant may have any desired genotype including, without limitation, wild type, transgenic, mutant, and/or the like with respect to a gene and/or trait of interest. A first and/or a second plant may comprises at least one antimicrobial peptide and/or at least one nucleic acid comprising a sequence encoding at least one antimicrobial peptide. Where both a first plant comprises at least one antimicrobial peptide and/or at least one nucleic acid comprising a sequence encoding at least one antimicrobial peptide and a second plant comprises at least one antimicrobial peptide and/or at least one nucleic acid comprising a sequence encoding at least one antimicrobial peptide, it may be desirable for the first and second plants to have the same and/or different antimicrobial peptides and/or nucleic acids encoding antimicrobial peptides. Grafting may comprise cutting a portion of a first plant to form a fresh cut site, cutting a portion of a second plant to create a second cut site, and/or contacting a first cut site with a second cut site. A cut site may comprise at least one vascular bundle. Grafting may comprise forming a graft junction and/or, optionally, sealing the graft junction (e.g., by coating the periphery of the graft junction with one or more barrier materials).

C. Treating Plant Disease

The present disclosure relates, in some embodiments, to compositions, organisms, systems, and methods for preventing, ameliorating, and/or treating a plant disease (e.g., a citrus disease) and/or at least one symptom of a plant disease. For example, a method may comprise grafting at least a portion of a plant (e.g., a citrus plant) having a plant disease and/or expressing at least one symptom of a plant disease with at least a portion of a plant (e.g., a citrus plant) comprising an antimicrobial peptide. Examples of a plant disease include, without limitation, bacterial canker (*Xanthomonas axonopodis* pv. citri) (Xac), and/or citrus Huanglongbing (ex greening) caused by *Candidatus Liberibacter asiaticus* (Las). According to some embodiments, preventing, ameliorating, and/or treating a plant disease (e.g., a citrus disease) and/or at least one symptom of a plant disease may comprise treating and/or curing one or more devastating bacterial diseases of citrus. For example, plants comprising stably integrated SoD2 and SoD7 transgenes in expressible form may display resistance to, without limitation, bacterial canker (*Xanthomonas axonopodis* pv. citri) (Xac), and/or citrus Huanglongbing (ex greening) caused by *Candidatus Liberibacter asiaticus* (Las). Such resistance has been observed as described in the Examples below.

According to some embodiments, the present disclosure relates to compositions, organisms, systems, and methods for augmenting a plant's native resistance to and/or conferring on a plant resistance to a plant disease (e.g., a citrus disease). For example, a method may comprise contacting a plant with an antimicrobial peptide and/or an expressible nucleic acid comprising a nucleic acid sequence encoding an antimicrobial peptide. An expressible nucleic acid comprising a nucleic acid sequence encoding an antimicrobial peptide may be and/or comprise an expression cassette in some embodiments. Contacting may comprise, according to some embodiments, grafting at least a portion of a target plant with a plant comprising an antimicrobial peptide and/or an expressible nucleic acid comprising a nucleic acid sequence encoding an antimicrobial peptide. In some embodiments, contacting may comprise contacting at least a portion of a target plant with a vector (e.g., via *Agrobacterium*-mediated transformation) comprising an antimicrobial peptide and/or an expressible nucleic acid comprising a nucleic acid sequence encoding an antimicrobial peptide. Examples of a plant disease include, without limitation, bacterial canker (*Xanthomonas axonopodis* pv. citri) (Xac), and/or citrus Huanglongbing (ex greening) caused by *Candidatus Liberibacter asiaticus* (Las).

D. Making a Citrus-Expressible Antimicrobial Peptide

In some embodiments, the present disclosure relates to compositions, organisms, systems, and methods for forming a citrus-expressible nucleic acid comprising a nucleic acid sequence encoding at least one spinach-derived antimicrobial peptide. For example, a method may comprise identifying an amino acid sequence of an antimicrobial peptide of interest, reverse translating the amino acid sequence to produce a first nucleic acid sequence; codon-optimizing the first nucleic acid sequence for expression in citrus to produce a second nucleic acid sequence, and/or synthesizing a nucleic acid having the second nucleic acid sequence. A method may comprise, in some embodiments, covalently bonding a nucleic acid having the second nucleic acid sequence with one or more nucleic acids having expression control sequences that are operable in citrus in an operable orientation and/or position relative to the nucleic acid having the second nucleic acid sequence.

As will be understood by those skilled in the art who have the benefit of the instant disclosure, other equivalent or alternative pathogen resistant citrus compositions, organisms, systems, and methods can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of expression control sequences, coding sequences, linkers, and/or terminator sequences may be varied. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for microbial and/or plant (e.g., with regard to sanitary, infectivity, safety, toxicity, biometric, and other considerations). Where desired, some embodiments of the disclosure may be practiced to the exclusion of other embodiments. For example, some polypeptide embodiments may be practiced to the exclusion of a particular amino acid sequence (e.g., SEQ ID NO: 26) and/or some nucleic acid embodiments may be practiced to the exclusion of a particular nucleic acid sequence (e.g., SEQ ID NO: 27).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100.

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

EXAMPLES

Some specific example embodiments of the disclosure may be illustrated by one or more of the examples provided herein.

Example 1: Plant Material

Plant materials (e.g., *Citrus sinensis*) were generally prepared for transformation as described by Yang et al., *Plant Cell Reports* (2000) 19:1203 et seq.

Example 2: Plasmid Construction and Bacterial Strains

Plasmid construction and bacterial strains were generally performed as described by Yang et al., *Plant Cell Reports* (2000) 19:1203 et seq.

Example 3: *Agrobacterium* Co-Culture and Plant Transformation

*Agrobacterium* co-culture and plant transformation were generally performed as described by Yang et al., *Plant Cell Reports* (2000) 19:1203 et seq.

Example 4: Selection and Regeneration of Transgenic Shoots

Selection and regeneration of transgenic shoots were generally performed as described by Yang et al., *Plant Cell Reports* (2000) 19:1203 et seq.

Example 5: Grafting of Transgenic Shoots

Grafting of transgenic shoots were generally performed as described by Yang et al., *Plant Cell Reports* (2000) 19:1203 et seq.

Example 6: Southern and Northern Analysis

Southern and northern analysis were generally performed as described by Yang et al., *Plant Cell Reports* (2000) 19:1203 et seq.

Example 7: Expression in *Citrus* Trees

Table 1 illustrates specific example embodiments of nucleic acid sequences codon-optimized for citrus. Signal peptides and structural gene coding sequences shown are flanked on either side by specific restriction enzyme sites. These sequences were used to construct expression cassettes, vectors, and transformed *Agrobacterium* for preparation of transgenic plants.

TABLE 1

Example embodiments of specific nucleotide sequences of antimicrobial genes. The nucleotide sequences were optimized for codon usage in Citrus.

| Antimicrobial Gene | Source of the Optimized Synthetic Gene (code) | Antimicrobial genes specific nucleotide sequences. The 5' nucleotides include the cloning site and a preferred context for the start codon. The 3' nucleotides include the cloning site. |
|---|---|---|
| SoD2 | GenScript (07) | SEQ ID NO: 9 |
|  | CODA (09) | SEQ ID NO: 11 |
| SoD7 | GenScript (08) | SEQ ID NO: 10 |
|  | CODA (10) | SEQ ID NO: 12 |
| SoD2 | DNA 2.0 (11) | SEQ ID NO: 30 |
| SoD7 | DNA 2.0 (12) | SEQ ID NO: 31 |
| SoD2 + SoD7 | GenScript (13) | SEQ ID NOS: 9 and 10 |
| SoD2 + SoD7 no SP | DNA 2.0 (16) | SEQ ID NO: 30 and 31 |

Figure 11:
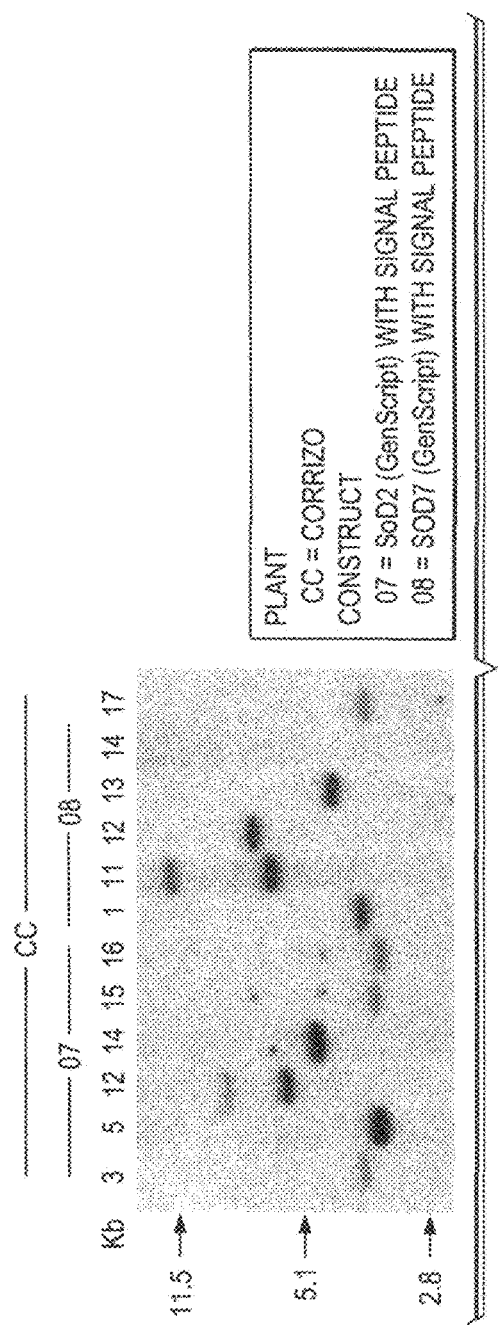
FIG. 11 is a representation of a Southern blot confirming insertion of defensins in Carrizo Citrange (CC) transformed with SoD2 (07) or SoD7 (08) nucleic acids, each comprising a GenScript-optimized sequence for expression in *Citrus*, according to a specific example embodiment of the disclosure.
Figure 12:
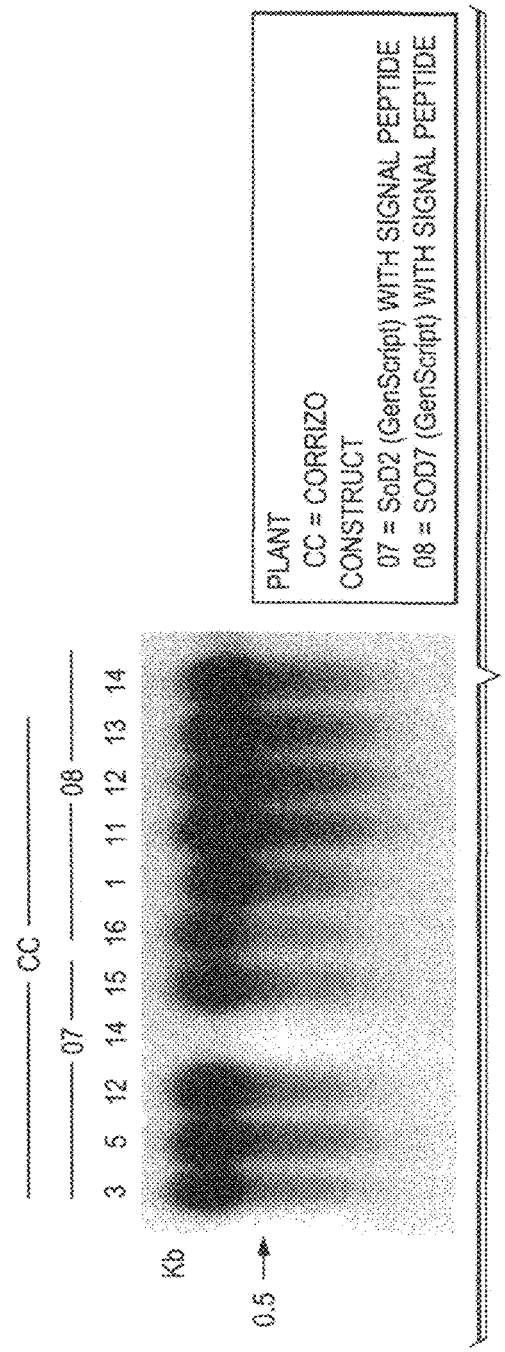
FIG. 12 is a representation of a northern blot showing RNA transcripts among transgenic events in Carrizo Citrange (CC) transformed with SoD2 (07) or SoD7 (08) nucleic acids, each comprising a GenScript-optimized sequence for expression in *Citrus*, according to a specific example embodiment of the disclosure.

The following cultivars were selected for transformation:
Orange: Hamlin ("04"), Rhode Red ("05"), and Marrs ("06") (FIGS. 3-7);
Grapefruit: Ruby Red ("01") (FIGS. 8-11) and Rio Red ("02") (Example 14 below);
Carrizo Citrange ("CC") (FIGS. 12-13);
Flying Dragon rootstock ("13" and "16");
Frost Eureka and Frost Lisbon (13" and "16");
Swingle rootstock (13" and "16"); and
C22 rootstock.
Constructs used for each cultivar are shown in Table 2.

TABLE 2

Orange, grapefruit, lemon and citrus rootstock cultivars transformed (seedling epicotyls) with three different synthetic sequences of each SoD2 and SoD7 genes encoding antimicrobial peptides from spinach (*Spinacia oleracea*) (at least 521 events in total).

| Generation | Defensin Synthetic Genes | Synthetic Gene Optimized-Codon Sequence (Sequence Code) | Citrus Cultivars (Cultivar Code) | Transgenic Events Codes (Cultivar and Gene) | Number of Transgenic Events |
|---|---|---|---|---|---|
| 2(141 events) | SoD2 + SP | GenScript (07) | Hamlin (04) | 0407 | 14 |
|  |  |  | Rhode Red (05) | 0507 | 12 |
|  |  |  | Marrs (06) | 0607 | 6 |
|  |  |  | Carrizo Citrange (CC) | CC2 | 18 |
|  |  | CODA (09) | Hamlin (04) | 0409 | 16 |
|  |  |  | Rhode Red (05) | 0509 | 6 |
|  | SoD7 + SP | GenScript (08) | Hamlin (04) | 0408 | 12 |
|  |  |  | Rhode Red (05) | 0508 | 8 |
|  |  |  | Marrs (06) | 0608 | 7 |
|  |  |  | Carrizo Citrange (CC) | CC7 | 29 |
|  |  | CODA (10) | Hamlin (04) | 0410 | 5 |
|  |  |  | Rhode Red (05) | 0510 | 8 |
| 3 (36 events) | SoD2-no SP | DNA 2.0 (11) | Hamlin (04) | 0411 | 11 |
|  |  |  | Ruby Red (01) | 0111 | 6 |
|  | SoD7-no SP | DNA 2.0 (12) | Hamlin (04) | 0412 | 13 |
|  |  |  | Ruby Red (01) | 0112 | 6 |
| 4 (187 events + 157 Swingle | SoD2 + 7 + SP | GenScript (13) | Hamlin (04) | 413 | 15 |
|  |  |  | Rhode Red (05) | 513 | 14 |
|  |  |  | Rio Red (02) | 213 | 18 |
|  |  |  | Frost Eureka Lemon (10) | 1013 | 30 |
|  |  |  | Frost Lisbon Lemon (11) | 1113 | 33 |
|  |  |  | Swingle Rootstock (12) | 1213 | 157 |
|  |  |  | Flying Dragon Rootstock (09) | 913 | 46 |

TABLE 2-continued

Orange, grapefruit, lemon and citrus rootstock cultivars transformed (seedling epicotyls) with three different synthetic sequences of each SoD2 and SoD7 genes encoding antimicrobial peptides from spinach (Spinacia oleracea) (at least 521 events in total).

| Generation | Defensin Synthetic Genes | Synthetic Gene Optimized-Codon Sequence (Sequence Code) | Citrus Cultivars (Cultivar Code) | Transgenic Events Codes (Cultivar and Gene) | Number of Transgenic Events |
|---|---|---|---|---|---|
| | | | C22 (08) | 813 | 15 |
| | | | Carrizo Citrange (07) | 713 | 16 |
| 4 | SoD2 + 7 | GenScript (07 + 08) | Hamlin (04) | 0413 | 15 |
| | | | Rhode Red (05) | 0513 | 1 |
| | | | Rio Red (02) | 0213 | 7 |
| | | | Carrizo Citrange (CC) | CC2 + 7 | 6 |
| 5 | SoD2 + 7-no SP | DNA 2.0 (16) | Hamlin (04) | 416 | Multiple GUS positive plants |
| | | | Frost Eureka Lemon (10) | 1016 | Multiple GUS positive plants |
| | | | Frost Lisbon Lemon (11) | 1116 | Multiple GUS positive plants |
| | | | Rhode Red (05) | 516 | Multiple GUS positive plants |

A. Transformation of Orange

Figure 3:
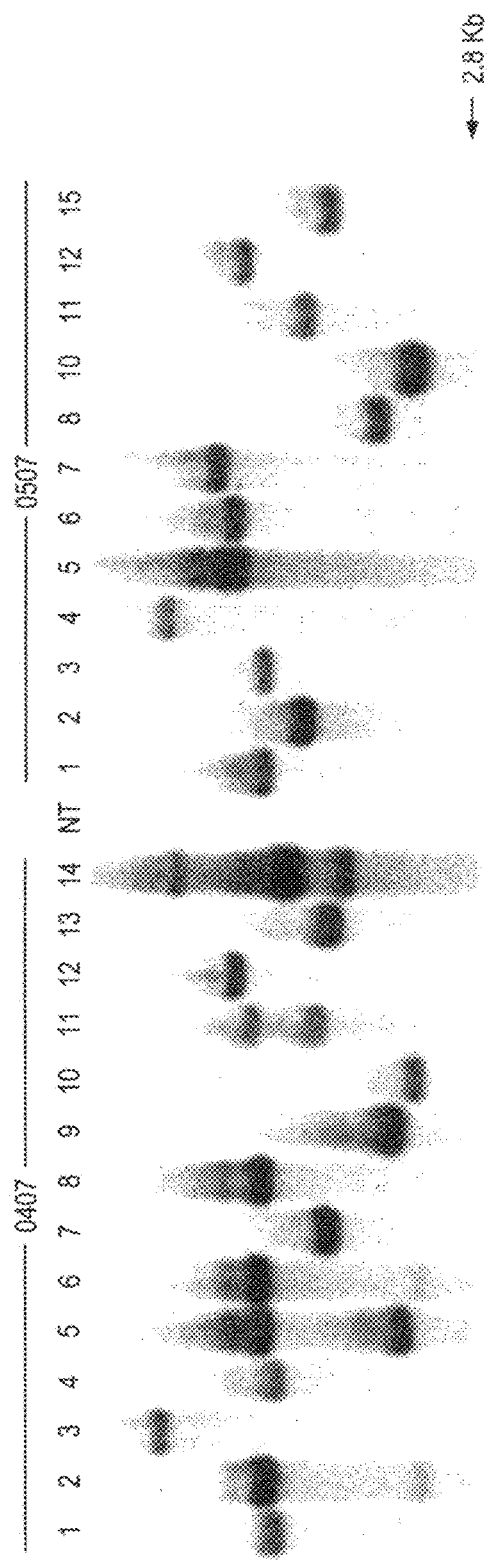
FIG. 3 is a representation of a Southern blot showing insertion number among transgenic events in Hamlin and Rhode Red transformed with a SoD2 (07) nucleic acid comprising a GenScript-optimized sequence for expression in *Citrus*, according to a specific example embodiment of the disclosure.
Figure 4:
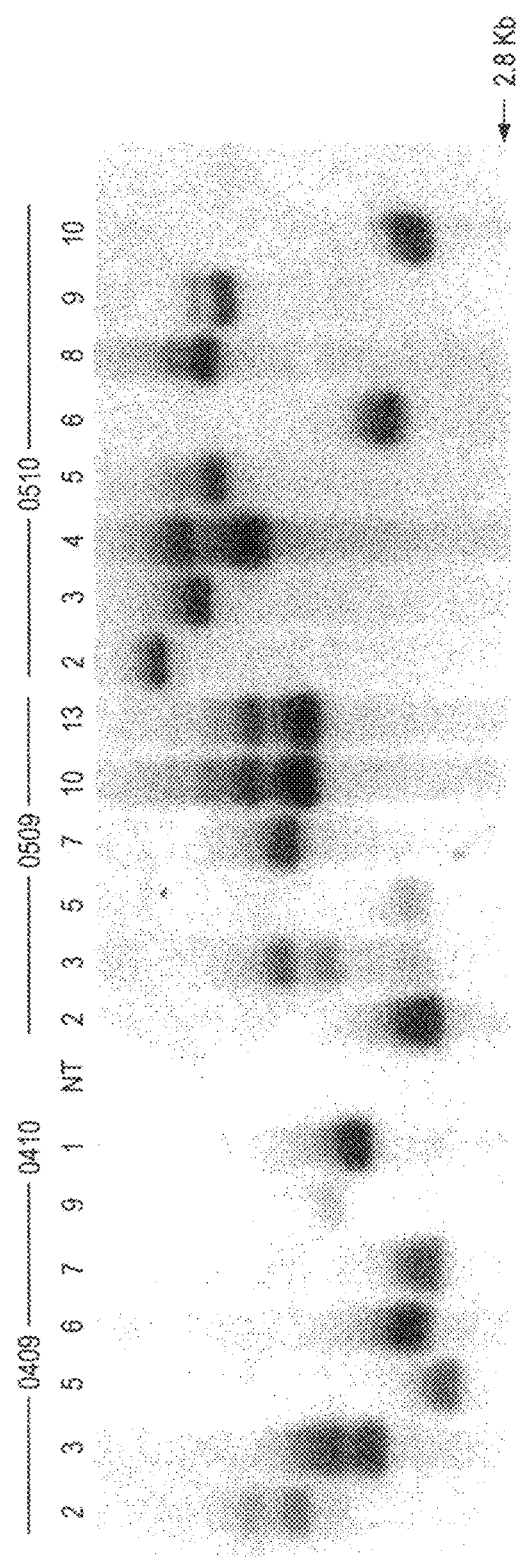
FIG. 4 is a representation of a Southern blot showing insertion number among transgenic events in Hamlin and Rhode Red transformed with SoD2 (09) or SoD7 (10) nucleic acids, each comprising a CODA-optimized sequence for expression in *Citrus*, according to specific example embodiments of the disclosure.

Orange plants were transformed with a single construct comprising GenScript-optimized SoD2 with signal peptide ("07"), GenScript-optimized SoD7 with signal peptide ("08"), CODA-optimized SoD2 with signal peptide ("09"), or CODA-optimized SoD2 with signal peptide ("10"). FIG. 3 is a representation of a Southern blot showing insertion number among transgenic events in Hamlin transformed with GenScript-optimized SoD2 (0407) and Rhode Red transformed with GenScript-optimized SoD2 (0507). FIG. 4 is a representation of a Southern blot showing insertion number among transgenic events in Hamlin transformed with CODA-optimized SoD2 (0409) or CODA-optimized SoD7 (0410) and Rhode Red transformed with CODA-optimized SoD2 (0509) or CODA-optimized SoD7 (0510). Additional transformation events are shown for GenScript-optimized SoD7 ("08") and CODA-optimized SoD2 ("09") in Hamlin in FIG. 9.

Figure 5:
FIG. 5 is a representation of a northern blot showing RNA transcripts among transgenic events in Marrs, transformed with SoD2 (07) or SoD7 (08) nucleic acids, each comprising a GenScript-optimized sequence for expression in *Citrus*, according to a specific example embodiment of the disclosure.
Figure 6:
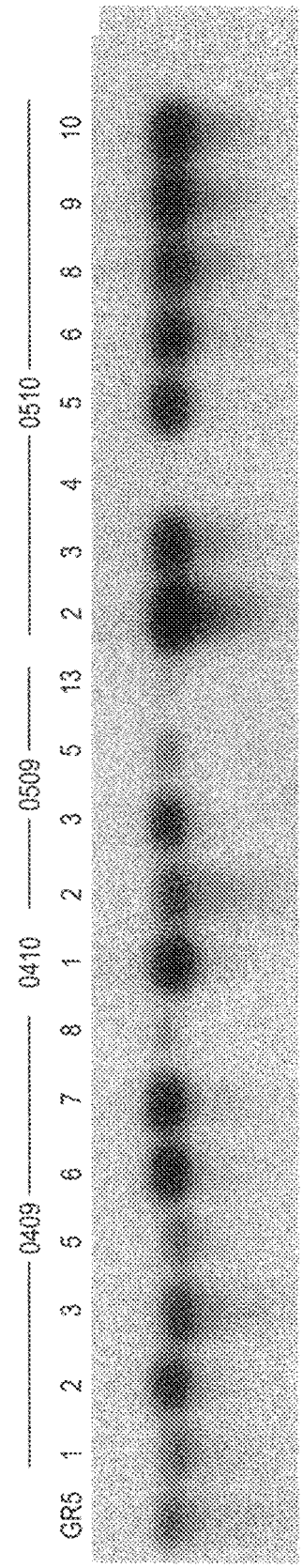
FIG. 6 is a representation of a northern blot showing RNA transcripts among transgenic events in Hamlin and Rhode Red, transformed with SoD2 (09) or SoD7 (10) nucleic acids, each comprising a CODA-optimized sequence for expression in *Citrus*, according to a specific example embodiment of the disclosure.
Figure 7:
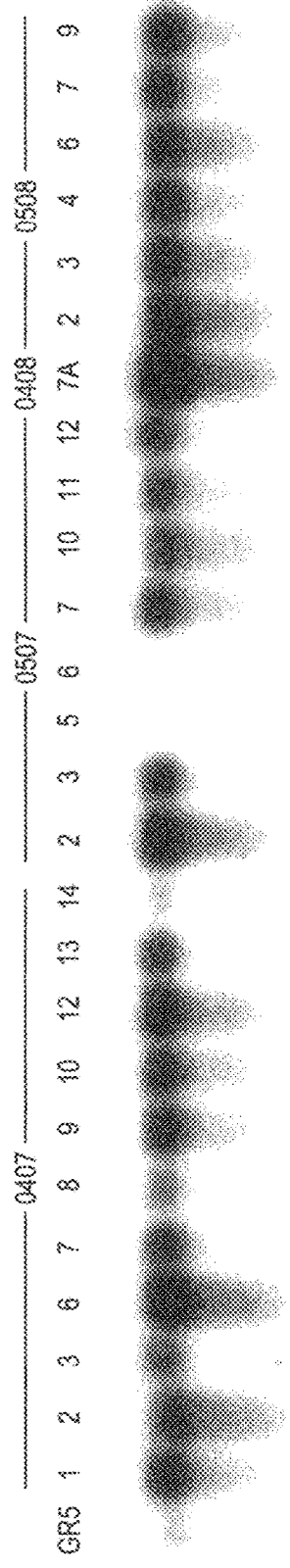
FIG. 7 is a representation of a northern blot showing RNA transcripts among transgenic events in Hamlin and Rhode Red, transformed with SoD2 (07) or SoD7 (08) nucleic acids, each comprising a GenScript-optimized sequence for expression in *Citrus*, according to a specific example embodiment of the disclosure.

Transgenic plants of the orange cultivars Hamlin, Rhode Red, and Marrs (n=82) produce high levels of transcripts of these antimicrobial genes (Table 2 and FIGS. 5-7). FIG. 5 is a representation of a northern blot showing RNA transcripts among transgenic events in Marrs, transformed with genes SoD2 (0607) or SoD7 (0608) GenScript-optimized for codon use in Citrus. FIG. 6 is a representation of a northern blot showing RNA transcripts among transgenic events in Hamlin transformed with CODA-optimized SoD2 (0409) or CODA-optimized SoD7 (0410) and Rhode Red transformed with CODA-optimized SoD2 (0509) or CODA-optimized SoD7 (0510). FIG. 7 is a representation of a northern blot showing RNA transcripts among transgenic events in Hamlin transformed with GenScript-optimized SoD2 (0407) or GenScript-optimized SoD7 (0408) and Rhode Red transformed with GenScript-optimized SoD2 (0507) or GenScript-optimized SoD7 (0508). For identification, Table 2 contains the transgenic event codes for cultivar and gene combination.

Figure 8:
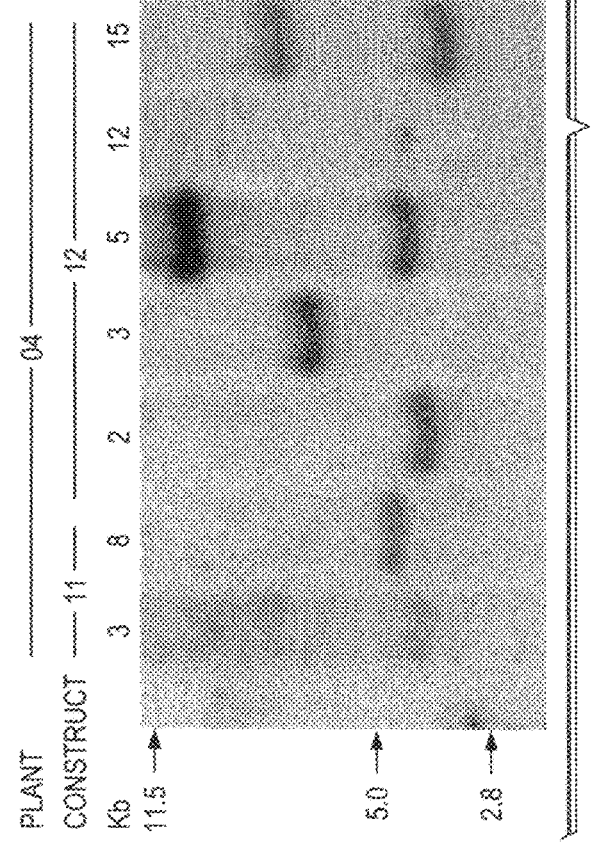
FIG. 8 is a representation of a Southern blot confirming insertion of SoD2 or SoD7 in Hamlin plants, transformed with SoD2 (11) or SoD7 (12) nucleic acids, each comprising a DNA 2.0-optimized sequence for expression in *Citrus*, according to a specific example embodiment of the disclosure.

Orange plants (Hamlin) were also transformed with a single construct comprising DNA 2.0-optimized SoD2 without signal peptide ("11") or DNA 2.0-optimized SoD7 without signal peptide ("12"). FIG. 8 is a representation of a Southern blot confirming insertion of SoD2 or SoD7 in these orange plants. Additional transformation events are shown for SoD7 (12) in Hamlin in FIG. 9.

B. Transformation of Grapefruit

Figure 9:
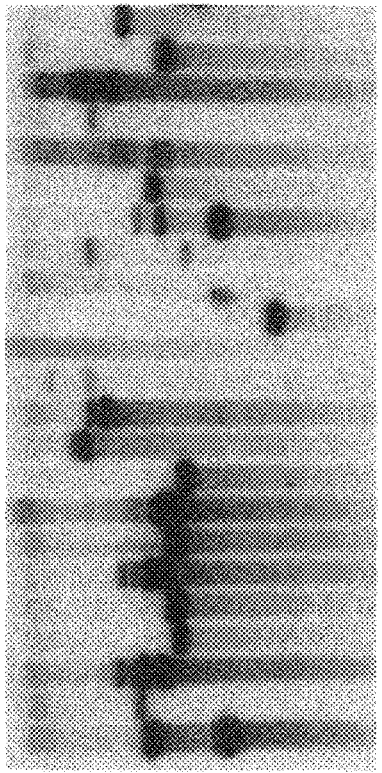
FIG. 9 is a representation of a Southern blot confirming insertion of defensins in Ruby Red (01) or Hamlin (04) transformed with SoD2 (09, 11), SoD7 (08, 12), or both SoD2 and SoD7 (13) nucleic acids, each comprising a sequence optimized for expression in *Citrus* using a sequence optimization algorithm (GenScript for 08 and 13; Coda for 09, and DNA 2.0 for 11 and 12), according to a specific example embodiment of the disclosure.
Figure 10:
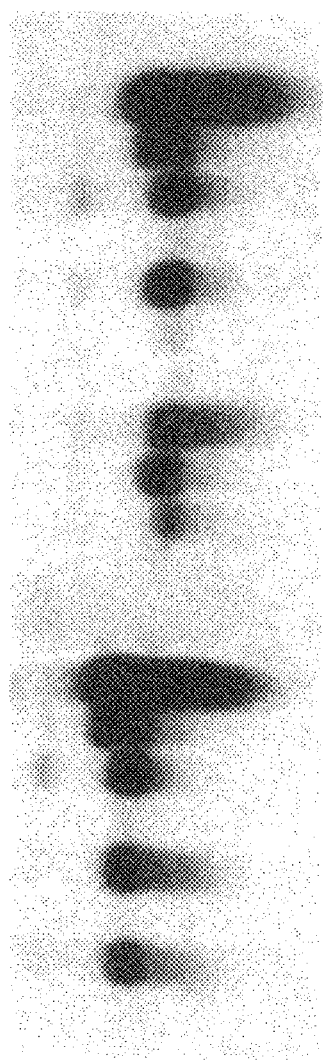
FIG. 10 is a representation of a northern blot showing RNA transcripts among transgenic events in Ruby Red (01) or Hamlin (04), transformed with SoD2 (11), SoD7 (08, 12), or both SoD2 and SoD7 (13) nucleic acids, each comprising a GenScript-optimized sequence (08 and 13) or DNA 2.0-optimized sequence (11 and 12) for expression in *Citrus*, according to a specific example embodiment of the disclosure.

Ruby Red ("01") plants were transformed with a single construct comprising DNA 2.0-optimized SoD2 without signal peptide ("11") or DNA 2.0-optimized SoD7 without signal peptide ("12"). FIG. 9 is a representation of a Southern blot (membrane was exposed to probes for both SoD2 and SoD7) confirming insertion of SoD2 or SoD7 in these grapefruit plants. FIG. 10 is a representation of a northern blot (membrane was exposed to probes for both SoD2 and SoD7) showing RNA transcripts among transgenic events in Ruby Red transformed with SoD2 (0111) or SoD7 (0112). For identification, Table 2 contains the transgenic event codes for cultivar and gene combination.

C. Transformation of Carrizo Citrange and C22

Carrizo Citrange and C22 rootstocks have been transformed with a construct comprising uidA and either SoD2 or SoD7 or SoD2+SoD7. FIG. 11 is a representation of a Southern blot confirming insertion of SoD2 (lanes marked "07") and SoD7 (lanes marked "08") in these Carrizo Citrange plants. FIG. 12 is a representation of a northern blot showing RNA transcripts isolated from these Carrizo Citrange plants (marked "CC") transformed with SoD2 (GenScript-optimized sequence with signal peptide) and SoD7 (GenScript-optimized sequence with signal peptide). For identification, Table 2 contains the transgenic event codes for cultivar and gene combination. A number of C22 transformation events have been confirmed in each by positive GUS staining.

Swingle and Flying Dragon (citrus rootstock) plants were transformed with various constructs including a single construct comprising GenScript-optimized SoD2 and SoD7 with signal peptide. Successful tranformation of C22, Flying Dragon, and Swingle plants has been at least confirmed by positive GUS staining.

D. Transformation of Lemon

Frost Lisbon and Frost Eureka (lemon) plants were transformed with various constructs including a single construct comprising GenScript-optimized SoD2 and SoD7 with signal peptide. Successful tranformation of C22, Flying Dragon, and Swingle plants has been at least confirmed by positive GUS staining.

E. Status of Transformation Events

The following cultivars of citrus and citrus rootstock have been transformed (seedling epicotyls) with synthetic sequences of SoD2 and SoD7 genes encoding antimocrobial from spinach (Spinacia oleracea), with the transformation even being stably maintained for between two and five years.

Orange:
  'Hamlin' Sweet Orange
  'Marrs' Sweet Orange
  'Rhode Red' Valencia
Grapefruit:
  'Rio Red' Grapefruit
  'Ruby Red' Grapefruit
Lemon:
  'Frost Eureka' Lemon
  'Frost Lisbon' Lemon
  'Limoneria 8A' Lemon
Lime:
  Key Lime
Rootstock:
  'Carrizo'
  'C22'
  'Flying Dragon'
  'Swingle'
  'Benton Citrange'

Example 8: Canker Disease Resistance Assay

Canker disease resistance was assessed using a detached leaf assay generally as described by Francis M I et al., 2010, *Eur J Plant Pathol* 127:571-578. Briefly, detached immature leaves (~75% expanded) were triple rinsed in sterile water to remove debris, sanitized by brief immersion in 70% ethanol followed by 0.5% sodium hypochloride, and again triple rinsed in sterile water. Sanitized leaves (3-4 per replicate×3 replicates) were infiltrated on their abaxial surface with an aqueous suspension of an Xcc strain isolated in Dade County Florida. Inoculated leaves were pressed on the surface of soft water agar plates, parafilm sealed, and incubated in an environmentally-controlled growth chamber.

Figure 13A:
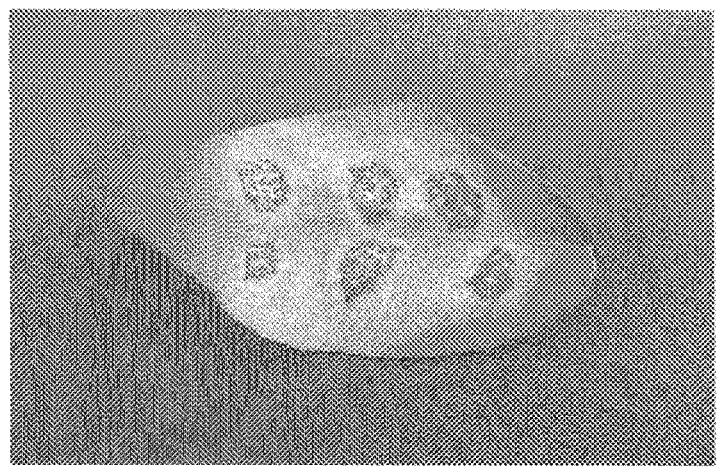
FIG. 13A is a photograph of an excised leaf from a non-transgenic grapefruit tree innoculated with a citrus canker pathogen according to specific example embodiments of the disclosure.
Figure 13B:
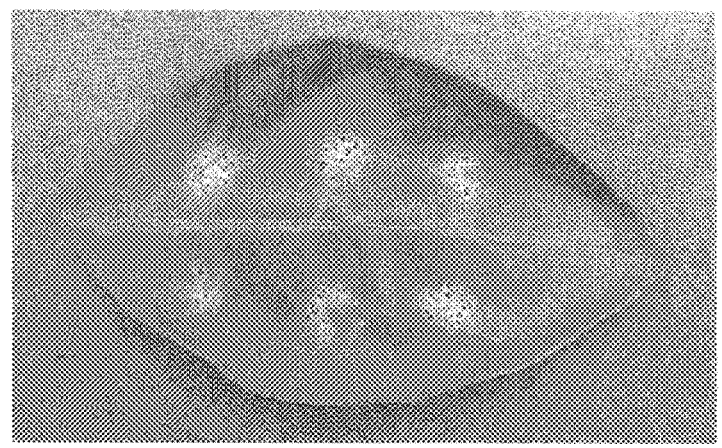
FIG. 13B is a photograph of an excised leaf from an SoD2 transgenic grapefruit tree innoculated with a citrus canker pathogen according to specific example embodiments of the disclosure.

FIG. 13A shows the result of inoculating a non-transgenic 'Rio Red' leaf with the citrus canker pathogen, as described above, and FIG. 13B shows the result of inoculating a transgenic leaf from a plant of 'Rio Red' expressing SoD2 with the citrus canker pathogen, as described above. A large reduction in the size and number of lesion on the transgenic can be seen.

Example 9: *Citrus* Greening (HLB) Disease Resistance Assay by Grafting

Figure 14:
FIG. 14 is a photograph of chimeric grapefruit trees resulting from the graft of uninfected, non-transgenic scions on citrus greening infected, non-transgenic rootstocks (left and center) or the graft of uninfected, SoD2 transgenic scions on citrus greening infected, non-transgenic rootstock (right), according to specific example embodiments of the disclosure.

FIG. 14 shows the result of graft inoculating non-transgenic 'Rio Red' (two trees on the left) or transgenic 'Rio Red' expressing SoD2 one tree on the right) with the citrus greening pathogen. A non-transgenic rootstock (*Cleopatra mandarin*) infected with HLB is used. Onto this rootstock several buds of transgenic 'Rio Red' are grafted and this is replicated. The same protocol is followed for non-transgenic buds of 'Rio Red'. After 8 weeks, vigorous growth can be seen from the transgenic graft, where there is no growth on the controls.

Example 10: *Citrus* Greening (HLB) Disease Resistance Assay by Psyllid Inoculation Resistance to bacterial infection and growth was assessed by two metrics. First, resistance was evaluated by the percentage of infection, namely the number of exposed plants that were infected. Second, a PCR-based method was used to amplify bacterial sequences. In this method, the relative degree of infection influences the number of PCR cycles required to produce detectable signal. For example a heavily infested plant might only require a few cycles while a plant with a low bacterial titer may require more cycles. In general, a plant that requires 30 or more cycles to observe detectable signal is regarded to be uninfected. Since some infections of citrus progress slowly, samples were collected for testing at 5 to 11 months after the time of first exposure and thereafter over a period of 6-9 months. The frequency of sample collection may vary from about every 45 days to about every 120 days. Ten to 15 replicates of each transgenic event plus non-transgenic controls are placed haphazardly in an insect proof green house that contains thousands' of psyllids carrying the citrus greening pathogen. The first PCR testing is done about five months after continuous exposure to psyllids. DNA extraction and PCR to detect the pathogen is essentially as described by Trey M S et al., 2006, *Proc. Fla. State Hort. Soc.* 119:89-93.

Example 11: Propagation and Resistance of Generation 1

Red Grapefruit (2 varieties) and Sweet Orange (3 varieties) were transformed with *Agrobacterium* comprising an expression vector having an artificial defensin gene construct that included a 2-amino acid insertion in the signal peptide and a single amino acid deletion in the coding sequence (SEQ ID NOS: 26 and 27). A total of 6 transformation events were further tested based on having high levels of SoD2 RNA expressed. Plants were cultivated as described herein and bacterial resistance was assessed as described. A first set of samples were collected after 11 months in the field (D0). Subsequent samples were collected the indicated number of days (42-471) after the first sampling (e.g., D42=11 months+42 days). Results are shown in Table 3.

TABLE 3

| Generation 1 Infection Data | | | | | | | |
|---|---|---|---|---|---|---|---|
| Plant Line | N | 0 | 42 | 90 | 127 | 271 | 384 | 471 |
| GR 311 Hamlin | 1 | 0% | 0% | 0% | 0% | 100% | 100% | 100% |
| Non Transgenic Hamlin | 1 | 0% | 0% | 100% | 100% | 100% | 100% | 100% |
| GR 420 Grapefruit | 1 | 0% | 0% | 0% | 0% | 0% | 100% | 100% |
| GR 824 Grapefruit | 2 | 0% | 0% | 50% | 50% | 100% | 100% | 100% |
| GR 867 Grapefruit | 1 | 0% | 0% | 0% | 0% | 100% | 100% | 100% |
| GR 882 Grapefruit | 2 | 0% | 0% | 0% | 50% | 50% | 50% | 50% |
| GR 890 Grapefruit | 1 | 0% | 0% | 0% | 0% | 0% | 100% | 100% |
| Non Transgenic Grapefruit | 7 | 0% | 0% | 0% | 14% | 0% | 57% | 57% |
| Non Transgenic Grapefruit Border | 6 | 0% | 0% | 0% | 0% | 50% | 50% | 50% |
| Total | 22 | 0% | 0% | 9% | 18% | 41% | 68% | 68% |

Example 12: Propagation and Resistance of Generation 2

Sweet Orange (2 varieties) were transformed with *Agrobacterium* comprising one of the following defensin gene constructs:
  (a) GenScript-optimized SoD2 with tobacco PR-1b signal peptide (SEQ ID NO: 9), (b) CODA-optimized SoD2 with tobacco PR-1b signal peptide (SEQ ID NO: 11),
(c) GenScript-optimized SoD7 with tobacco PR-1b signal peptide (SEQ ID NO: 10), or
(d) CODA-optimized SoD7 with tobacco PR-1b signal peptide (SEQ ID NO: 12).

A total of 71 transformation events were observed. Plants were cultivated as described herein and bacterial resistance was assessed as described. A first set of samples were collected after 5 months in the psyllid house (Day 0). Subsequent samples were collected the indicated number of days after the first sampling (e.g., Day 73=5 months+73 days). Results are shown in FIG. 15, FIG. 16, Table 4, and Table 5.

TABLE 4

Generation 2 Infection Data

| Code | Scion[1] | Genotype[2] | Rootstock[3] | Gene[4] | 1st Sampling Day 0 | 1st Sampling Mean Ct | 2nd Sampling Day 73 | 2nd Sampling Mean Ct | 3rd Sampling Day 170 | 3rd Sampling Mean Ct | Partial 4th Sampling Day 317 | Partial 4th Sampling Mean Ct |
|---|---|---|---|---|---|---|---|---|---|---|---|---|
| 0407-01 | H | SO | Cm | SoD2 (G) | 13% | 23.02 | 33% | 26.09 | 33% | 23.28 | | |
| 0407-02 | H | SO | Cm | SoD2 (G) | 0% | | 27% | 28.78 | 47% | 26.55 | | |
| 0407-03 | H | SO | Cm | SoD2 (G) | 0% | | 7% | 24.84 | 33% | 29.32 | | |
| 0407-04 | H | SO | Cm | SoD2 (G) | 20% | 25.56 | 27% | 27.18 | 40% | 25.28 | | |
| 0407-06 | H | SO | Cm | SoD2 (G) | 7% | 31.07 | 7% | 26.16 | 13% | 22.52 | 67% | 28.81 |
| 0407-07 | H | SO | Cm | SoD2 (G) | 20% | 27.37 | 13% | 25.96 | 27% | 25.85 | 80% | 27.26 |
| 0407-09 | H | SO | Cm | SoD2 (G) | 13% | 26.05 | 27% | 26.83 | 33% | 22.90 | | |
| 0407-10 | H | SO | Cm | SoD2 (G) | 7% | 23.57 | 27% | 26.04 | 47% | 25.32 | | |
| 0407-11 | H | SO | Cm | SoD2 (G) | 7% | 26.75 | 33% | 26.21 | 67% | 24.87 | | |
| 0407-12 | H | SO | Cm | SoD2 (G) | 7% | 31.66 | 13% | 24.51 | 33% | 23.39 | | |
| 0407-13 | H | SO | Cm | SoD2 (G) | 13% | 23.52 | 27% | 27.89 | 40% | 23.54 | | |
| 0408-01 | H | SO | Cm | SoD7 (G) | 13% | 24.88 | 27% | 25.55 | 53% | 26.15 | | |
| 0408-07A | H | SO | Cm | SoD7 (G) | 7% | 23.40 | 20% | 28.48 | 27% | 22.64 | 80% | 27.08 |
| Hamlin NT Control | H | SO | Cm | Control | 0% | | 20% | 28.83 | 40% | 24.59 | 87% | 25.92 |
| 0409-02 | H | SO | Cm | SoD2 (C) | 7% | 27.34 | 0% | | 20% | 24.04 | 80% | 26.23 |
| 0409-03 | H | SO | Cm | SoD2 (C) | 7% | 22.28 | 7% | 28.79 | 27% | 22.12 | 93% | 25.52 |
| 0409-06 | H | SO | Cm | SoD2 (C) | 0% | | 20% | 26.52 | 40% | 24.01 | | |
| 0409-07 | H | SO | Cm | SoD2 (C) | 0% | | 20% | 26.31 | 40% | 23.17 | | |
| 0410-01 | H | SO | Cm | SoD7 (C) | 0% | | 40% | 22.96 | 73% | 24.78 | | |
| 0507-01 | RR | SO | Cm | SoD2 (G) | 0% | | 47% | 26.35 | 60% | 23.60 | | |
| 0507-02 | RR | SO | Cm | SoD2 (G) | 13% | 28.26 | 40% | 22.18 | 47% | 25.14 | | |
| 0507-03 | RR | SO | Cm | SoD2 (G) | 13% | 24.61 | 47% | 26.64 | 60% | 23.59 | | |
| 0507-04 | RR | SO | Cm | SoD2 (G) | 13% | 26.21 | 27% | 25.25 | 40% | 24.63 | | |
| 0507-07 | RR | SO | Cm | SoD2 (G) | 0% | | 13% | 27.42 | 27% | 22.61 | 67% | 29.19 |
| O507-08 | RR | SO | Cm | SoD2 (G) | 7% | 25.97 | 40% | 26.37 | 40% | 24.03 | | |
| 0507-10 | RR | SO | Cm | SoD2 (G) | 7% | 26.04 | 27% | 25.71 | 40% | 25.29 | | |
| 0507-11 | RR | SO | Cm | SoD2 (G) | 0% | | 40% | 26.51 | 53% | 22.26 | | |
| 0507-12 | RR | SO | Cm | SoD2 (G) | 0% | | 20% | 17.61 | 13% | 22.56 | 77% | 27.17 |
| 0507-15 | RR | SO | Cm | SoD2 (G) | 13% | 24.49 | 53% | 25.65 | 73% | 23.10 | | |
| 0508-02 | RR | SO | Cm | SoD7 (G) | 13% | 29.40 | 47% | 26.25 | 73% | 23.90 | | |
| 0508-03 | RR | SO | Cm | SoD7 (G) | 7% | 31.44 | 33% | 24.53 | 60% | 25.37 | | |
| 0508-04 | RR | SO | Cm | SoD7 (G) | 13% | 25.65 | 20% | 28.00 | 60% | 25.74 | | |
| 0508-06 | RR | SO | Cm | SoD7 (G) | 0% | | 7% | 27.72 | 27% | 24.33 | 79% | 25.56 |
| 0508-07 | RR | SO | Cm | SoD7 (G) | 27% | 26.86 | 67% | 25.30 | 100% | 24.76 | 100% | 21.87 |
| 0508-08 | RR | SO | Cm | SoD7 (G) | 7% | 24.35 | 27% | 24.55 | 53% | 23.07 | | |
| 0508-09 | RR | SO | Cm | SoD7 (G) | 20% | 25.55 | 33% | 24.69 | 60% | 24.40 | | |
| 0508-10 | RR | SO | Cm | SoD7 (G) | 7% | 25.96 | 33% | 25.94 | 47% | 23.30 | | |
| Rhode Red NT Control | RR | SO | Cm | Control | 13% | 27.03 | 27% | 25.64 | 67% | 25.46 | 100% | 22.32 |
| 0509-02 | RR | SO | Cm | SoD2 (C) | 13% | 24.36 | 53% | 23.07 | 60% | 23.77 | | |
| 0509-03 | RR | SO | Cm | SoD2 (C) | 13% | 25.28 | 27% | 26.60 | 53% | 26.02 | | |
| 0509-07 | RR | SO | Cm | SoD2 (C) | 7% | 30.19 | 20% | 24.85 | 47% | 25.71 | | |
| 0509-10 | RR | SO | Cm | SoD2 (C) | 20% | 27.29 | 20% | 24.93 | 67% | 26.26 | | |
| 0510-02 | RR | SO | Cm | SoD7 (C) | 7% | 30.66 | 27% | 23.36 | 47% | 24.42 | | |
| 0510-03 | RR | SO | Cm | SoD7 (C) | 7% | 22.01 | 20% | 24.70 | 53% | 25.39 | | |
| 0510-05 | RR | SO | Cm | SoD7 (C) | 7% | 31.54 | 7% | 31.03 | 7% | 31.22 | 17% | 35.78 |
| 0510-06 | RR | SO | Cm | SoD7 (C) | 0% | | 33% | 26.56 | 80% | 24.48 | 93% | 23.67 |
| 0510-08 | RR | SO | Cm | SoD7 (C) | 7% | 23.07 | 47% | 25.29 | 60% | 22.32 | | |
| 0510-09 | RR | SO | Cm | SoD7 (C) | 0% | | 33% | 24.63 | 47% | 24.02 | | |
| 0510-10 | RR | SO | Cm | SoD7 (C) | 0% | | 20% | 27.68 | 60% | 25.16 | | |
| Extra NT Controls | | | | | | | | | | | | |
| Hamlin | H | SO | Cm | Control | 0% | | 40% | 27.29 | 47% | 23.25 | | |
| Hamlin | H | SO | Cm | Control | 7% | 24.49 | 13% | 24.87 | 33% | 25.58 | | |
| Hamlin | H | SO | Cm | Control | 0% | | 33% | 24.44 | 33% | 25.82 | | |

TABLE 4-continued

Generation 2 Infection Data

| | | | | | 1st Sampling | | 2nd Sampling | | 3rd Sampling | | Partial 4th Sampling | |
|---|---|---|---|---|---|---|---|---|---|---|---|---|
| Code | Scion[1] | Genotype[2] | Rootstock[3] | Gene[4] | Day 0 | Mean Ct | Day 73 | Mean Ct | Day 170 | Mean Ct | Day 317 | Mean Ct |
| Rhode Red | RR | SO | Cm | Control | 7% | 24.61 | 33% | 26.27 | 27% | 22.98 | | |
| Rhode Red | RR | SO | Cm | Control | 0% | | 40% | 27.07 | 33% | 24.49 | | |
| Rhode Red | RR | SO | Cm | Control | 7% | 24.36 | 33% | 29.01 | 47% | 26.50 | | |

[1]H = Hamlin; RR = Rhode Red
[2]SO = Sweet Orange
[3]Cm = Cleopatra mandarin
[4](G) = GenScript-optimized sequence; (C) = CODA-optimized sequence

Example 13: Propagation and Resistance of Generation 3

One Sweet Orange variety and one grapefruit variety were transformed with *Agrobacterium* comprising one of the following defensin gene constructs:

(a) GenScript-optimized SoD2 with no signal peptide (SEQ ID NO: 3), or (b) GenScript-optimized SoD7 with no signal peptide (SEQ ID NO: 4).

A total of 36 transformation events were observed. Plants were cultivated as described herein and bacterial resistance was assessed as described. A first set of samples were collected after 5 months in the psyllid house (Day 0). Subsequent samples were collected the indicated number of days after the first sampling (e.g., Day 103=5 months+103 days). Results are shown in FIG. 16 and Table 5.

TABLE 5

Generations 2 and 3 Infection Data

| | | | | | | 2nd Sampling | | | 3rd Sampling | | |
|---|---|---|---|---|---|---|---|---|---|---|---|
| Code | Scion[1] | Genotype[2] | Rootstock[3] | Gene[4] | 1st Sampling Day 0 | Day 103 | Avg Ct | Ct of Positive | Day 215 | Avg Ct | Ct of Positive |
| 41103 | H | SO | Cm | SoD2 (—P) | 10% | 10% | 37.98 | 24.78 | 10% | 36.83 | 19.62 |
| 41108 | H | SO | Cm | SoD2 (—P) | 0% | 0% | 40.00 | | 0% | 38.93 | |
| 41107 | H | SO | Cm | SoD2 (—P) | 10% | 14% | 37.24 | 23.44 | 14% | 35.28 | 21.02 |
| 41110 | H | SO | Cm | SoD2 (—P) | 0% | 10% | 38.18 | 26.35 | 20% | 35.24 | 23.33 |
| 40918 | H | SO | Cm | SoD2 (C) | 0% | 0% | 39.74 | | 10% | 36.97 | 21.53 |
| 40915 | H | SO | Cm | SoD2 (C) | 0% | 11% | 38.07 | 25.22 | 22% | 34.31 | 24.44 |
| 41004 | H | SO | Cm | SoD7 (C) | 0% | 10% | 38.37 | 23.72 | 20% | 35.24 | 25.54 |
| 40814 | H | SO | Cm | SoD7 (G) | 0% | 20% | 36.62 | 26.39 | 10% | 36.85 | 24.35 |
| 40817 | H | SO | Cm | SoD7 (G) | 10% | 10% | 37.97 | 22.93 | 30% | 34.17 | 23.40 |
| 11206 | RR | Gf | Cm | SoD7 (—P) | 0% | 30% | 35.18 | 23.93 | 40% | 32.27 | 24.69 |
| 11204 | RR | Gf | Cm | SoD7 (—P) | 0% | 10% | 37.63 | 24.56 | 30% | 33.49 | 22.16 |
| 40813 | H | SO | Cm | SoD7 (G) | 10% | 11% | 37.73 | 22.63 | 44% | 31.96 | 22.62 |
| 11201 | RR | Gf | Cm | SoD7 (—P) | 0% | 30% | 35.87 | 26.76 | 30% | 33.71 | 23.06 |
| 41109 | H | SO | Cm | SoD2 (—P) | 0% | 10% | 38.46 | 24.64 | 10% | 37.25 | 22.14 |
| 11208 | RR | Gf | Cm | SoD7 (—P) | 0% | 0% | 39.82 | | 0% | 38.42 | |
| 11108 | RR | Gf | Cm | SoD2 (—P) | 0% | 0% | 38.60 | | 13% | 36.15 | 21.66 |
| 11103 | RR | Gf | Cm | SoD2 (—P) | 0% | 20% | 36.98 | 26.00 | 20% | 33.73 | 19.99 |
| 60811 | M | SO | Cm | SoD7 (G) | 0% | 0% | 39.66 | | 0% | 39.03 | |
| Marrs WT | M | SO | Cm | Control | 0% | 10% | 38.81 | 28.14 | 20% | 35.57 | 24.93 |
| 40820 | H | SO | Cm | SoD7 (G) | 10% | 20% | 36.99 | 25.96 | 30% | 34.94 | 23.65 |
| 41101 | H | SO | Cm | SoD2 (—P) | 0% | 10% | 37.65 | 23.09 | 20% | 34.53 | 21.92 |
| Ruby Red WT | RR | Gf | Cm | Control | 0% | 0% | 39.39 | | 30% | 34.88 | 26.93 |
| 11105 | RR | Gf | Cm | SoD2 (—P) | 0% | 10% | 38.64 | 26.38 | 20% | 36.32 | 24.70 |
| 40810 A | H | SO | Cm | SoD7 (G) | 0% | 25% | 35.46 | 24.94 | 50% | 30.83 | 23.08 |
| 11203 | RR | Gf | Cm | SoD7 (—P) | 0% | 20% | 37.84 | 29.19 | 20% | 35.55 | 21.51 |
| 40914 | H | SO | Cm | SoD2 (C) | 0% | 0% | 39.66 | | 30% | 35.22 | 26.78 |
| 40812 | H | SO | Cm | SoD7 (G) | 0% | 10% | 37.99 | 27.44 | 20% | 35.67 | 21.75 |
| 41102 | H | SO | Cm | SoD2 (—P) | 10% | 40% | 35.03 | 27.58 | 60% | 29.83 | 23.83 |
| Hamlin WT | H | SO | Cm | Control | 0% | 40% | 33.76 | 24.41 | 50% | 29.52 | 22.14 |
| 60813 | M | SO | Cm | SoD7 (G) | 0% | 0% | 40.00 | | 13% | 37.06 | 24.02 |
| 60804 | M | SO | Cm | SoD7 (G) | 10% | 0% | 39.80 | | 0% | 37.74 | |
| 60703 | M | SO | Cm | SoD2 (G) | 0% | 33% | 36.35 | 30.88 | 33% | 36.07 | 25.07 |
| 60862 | M | SO | Cm | SoD7 (G) | 0% | 0% | 39.18 | | 10% | 37.87 | 31.23 |
| 60702 | M | SO | Cm | SoD2 (G) | 0% | 10% | 38.30 | 27.16 | 20% | 35.46 | 24.11 |
| 41211 | H | SO | Cm | SoD7 (—P) | 10% | 20% | 36.47 | 24.33 | 30% | 34.02 | 21.20 |
| 41203 | H | SO | Cm | SoD7 (—P) | 0% | 0% | 39.93 | | 0% | 38.17 | |
| 60812 | M | SO | Cm | SoD7 (G) | 0% | 0% | 40.00 | | 10% | 36.79 | 23.40 |
| 60810 | M | SO | Cm | SoD7 (G) | 10% | 20% | 37.25 | 26.25 | 70% | 27.87 | 23.44 |
| 60767 | M | SO | Cm | SoD2 (G) | 0% | 10% | 38.51 | 25.13 | 40% | 33.77 | 25.40 |
| 60701 | M | SO | Cm | SoD2 (G) | 0% | 20% | 37.45 | 28.07 | 50% | 30.37 | 23.85 |

TABLE 5-continued

Generations 2 and 3 Infection Data

| Code | Scion[1] | Genotype[2] | Rootstock[3] | Gene[4] | 1st Sampling Day 0 | 2nd Sampling | | | 3rd Sampling | | |
|---|---|---|---|---|---|---|---|---|---|---|---|
| | | | | | | Day 103 | Avg Ct | Ct of Positive | Day 215 | Avg Ct | Ct of Positive |
| 41210 | H | SO | Cm | SoD7 (—P) | 0% | 0% | 39.60 | | 20% | 34.62 | 22.91 |
| 41202 | H | SO | Cm | SoD7 (—P) | 10% | 17% | 35.89 | 23.81 | 50% | 30.85 | 22.69 |
| 60706 | M | SO | Cm | SoD2 (G) | 0% | 10% | 37.64 | 25.23 | 50% | 30.82 | 23.24 |
| 41209 | H | SO | Cm | SoD7 (—P) | 0% | 40% | 33.36 | 24.97 | 70% | 27.11 | 22.03 |
| 41113 | H | SO | Cm | SoD2 (—P) | 20% | 60% | 31.02 | 25.03 | 80% | 25.36 | 21.70 |
| 41215 | H | SO | Cm | SoD7 (—P) | 20% | 40% | 33.73 | 24.32 | 70% | 25.95 | 21.94 |
| 60808 | M | SO | Cm | SoD7 (G) | 0% | 0% | 39.35 | | 22% | 36.32 | 22.11 |
| 41208 | H | SO | Cm | SoD7 (—P) | 0% | 0% | 39.62 | | 11% | 37.30 | 22.04 |
| 41112 | H | SO | Cm | SoD2 (—P) | 20% | 20% | 35.94 | 25.32 | 40% | 31.22 | 22.22 |
| 41214 | H | SO | Cm | SoD7 (—P) | 0% | 20% | 36.57 | 24.47 | 50% | 29.72 | 21.99 |
| 60705 | M | SO | Cm | SoD2 (G) | 0% | 10% | 37.96 | 23.82 | 10% | 36.57 | 21.02 |
| 41204 | H | SO | Cm | SoD7 (—P) | 0% | 0% | 40.00 | | 10% | 36.50 | 22.28 |
| 41111 | H | SO | Cm | SoD2 (—P) | 10% | 13% | 37.98 | 23.82 | 25% | 35.18 | 24.46 |
| Hamlin WT | H | SO | Cm | Control | 0% | 25% | 35.56 | 26.41 | 55% | 29.82 | 22.51 |
| Marrs WT | M | SO | Cm | Control | 0% | 0% | 39.16 | | 33% | 33.11 | 22.73 |

[1]H = Hamlin; RR = Ruby Red; M = Marrs
[2]SO = Sweet Orange; Gf = Grapefruit
[3]Cm = Cleopatra mandarin
[4](G) = GenScript-optimized sequence; (C) = CODA-optimized sequence; (—P) = DNA 2.0-optimized sequence with no signal peptide Example 14: Propagation and Resistance of Generation 4

A first line of Sweet Orange (2 varieties), one grapefruit, and two rootstocks were prepared to co-express (i) GenScript SoD2 with tobacco PR-1b signal peptide (SEQ ID NO: 9) and (ii) GenScript SoD7 with tobacco PR-1b signal peptide (SEQ ID NO: 10). More specifically, plants were transformed with a double defensin construct comprising, in a 5' to 3' direction SoD2, uidA, and SoD7 (13). A total of 29 transformation events were observed with another 28 GUS-positive candidates in tissue culture or just out of tissue culture. Plants confirmed to co-express SoD2 and SoD7 will be cultivated and evaluated in infection assays to determine the degree to which coexpression prevents, ameliorates, and/or treats infection.

FIG. 9 is a representation of a Southern blot (membrane was exposed to probes for both SoD2 and SoD7) showing insertion number among transgenic events in Hamlin transformed with a double defensin construct comprising SoD2 and SoD7 (0413). FIG. 10 also shows insertion number among transgenic events in Hamlin transformed with a double defensin construct comprising SoD2 and SoD7 (0413).

Figure 17:
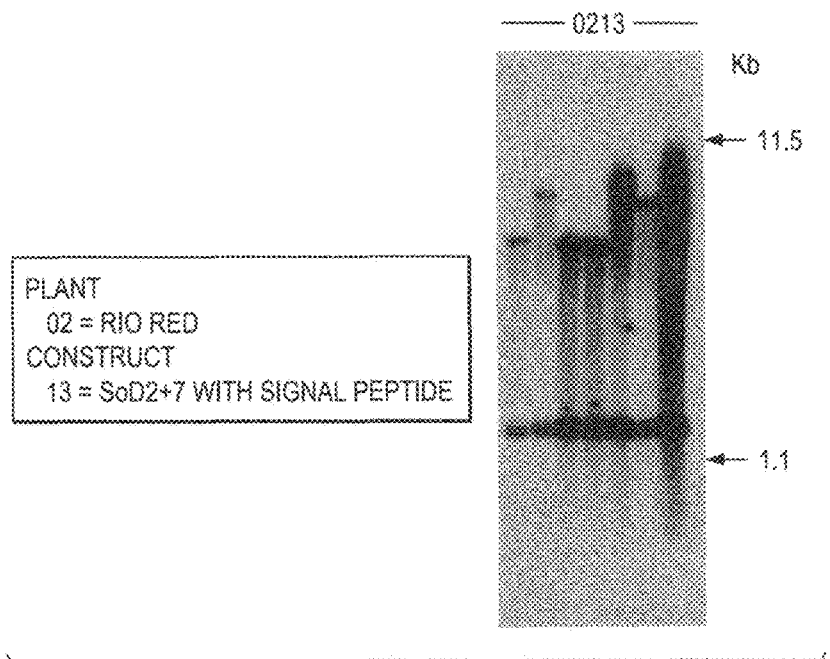
FIG. 17 is a representation of a Southern blot confirming insertion of defensins in Rio Red (02) transformed with both SoD2 and SoD7 (13) nucleic acids, each comprising a GenScript-optimized sequence for expression in *Citrus*, according to a specific example embodiment of the disclosure.
Figure 18:
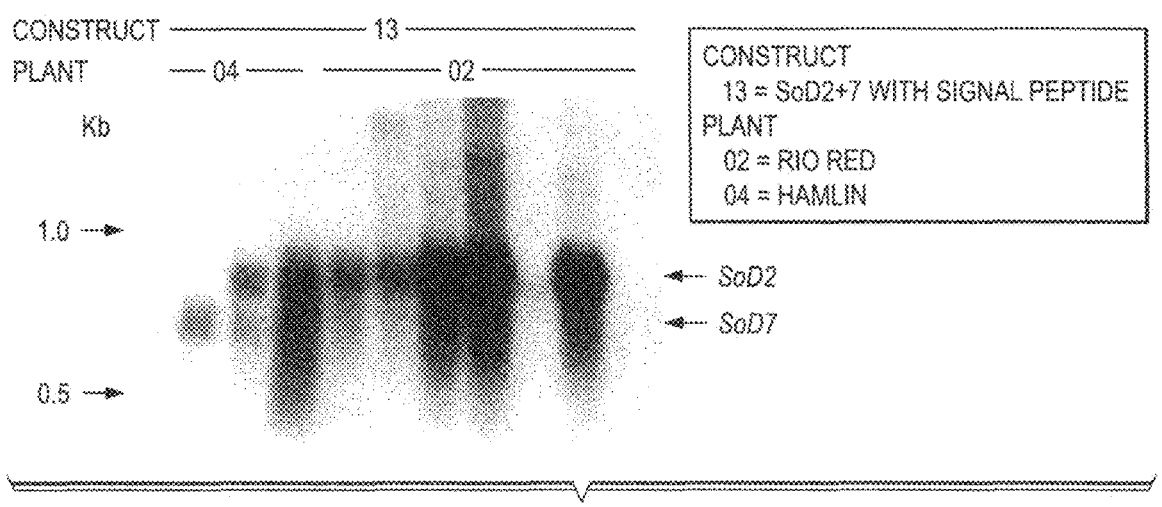
FIG. 18 is a representation of a northern blot showing RNA transcripts among transgenic events in Rio Red (02) or Hamlin (04), transformed with both SoD2 and SoD7 (13) nucleic acids, each comprising a GenScript-optimized sequence for expression in *Citrus*, according to a specific example embodiment of the disclosure.

Rio Red plants (02) were transformed with a double defensin construct (13). FIG. 17 is a representation of a Southern blot confirming insertion of both SoD2 and SoD7 in these Rio Red plants. DNA was cut with a single restriction enzyme that cut within SoD2, uidA, and SoD7 and blotted with both SoD2 and SoD7 probes simultaneously. FIG. 18 is a representation of a northern blot showing RNA transcripts isolated from Rio Red plants (marked "02") transformed with SoD2 (GenScript-optimized sequence with signal peptide) and SoD7 (GenScript-optimized sequence with signal peptide). RNA transcripts isolated from Hamlin plants (marked "04") are also shown.

Example 15: Propagation and Resistance of Generation 5

Evaluation of coexpression of SoD2 and SoD7 is underway. A line of Sweet Orange (1 variety) was prepared to co-express (i) DNA 2.0 SoD2 with no signal peptide (SEQ ID NO: 30) and (ii) DNA 2.0 SoD7 with no signal peptide (SEQ ID NO: 31). Transformation and expression may be confirmed by Southern and northern blotting analysis. Plants may be cultivated as described herein and bacterial resistance evaluated as described. Plants confirmed to co-express SoD2 and SoD7 may be cultivated and evaluated in infection assays to determine the degree to which coexpression prevents, ameliorates, and/or treats infection.

Example 16: Expression of Defensin Constructs in Various Plants

Stable expression of defensin constructs comprising nucleic acid sequences codon-optimized for citrus has been confirmed in the following:

| Cultivar | Gene Code | # Events |
|---|---|---|
| Rio Red Grapefruit | 13 | 18 |
| Ruby Red Grapefruit | 11 and 12 | 12 |
| Hamlin Sweet Orange | 07, 08, 09, 10, 11, 12, 13, and 16 | over 86 |
| Marrs Sweet Orange | 07 and 08 | 13 |
| Rhode Red Valencia Orange | 07, 08, 09, 10, 13 | over 48 |
| Frost Eureka Lemon | 13 and 16 | over 30 |
| Frost Lisbon Lemon | 13 and 16 | over 33 |
| C22 and Carrizo Citrange Rootstocks | 07, 08, 13 | 42 |
| Flying dragon and Swingle Rootstocks | 13 | Multiple GUS+ |

For all constructs, individual transformation events have been found spanning a range of expression levels from no expression (e.g., since Southern results demonstrate the gene is present, often in multiple copies, it may be that the transgene has been silenced) to low expression to high expression.

Example 17: Antibodies to SoD2 and SoD7

Figure 19:
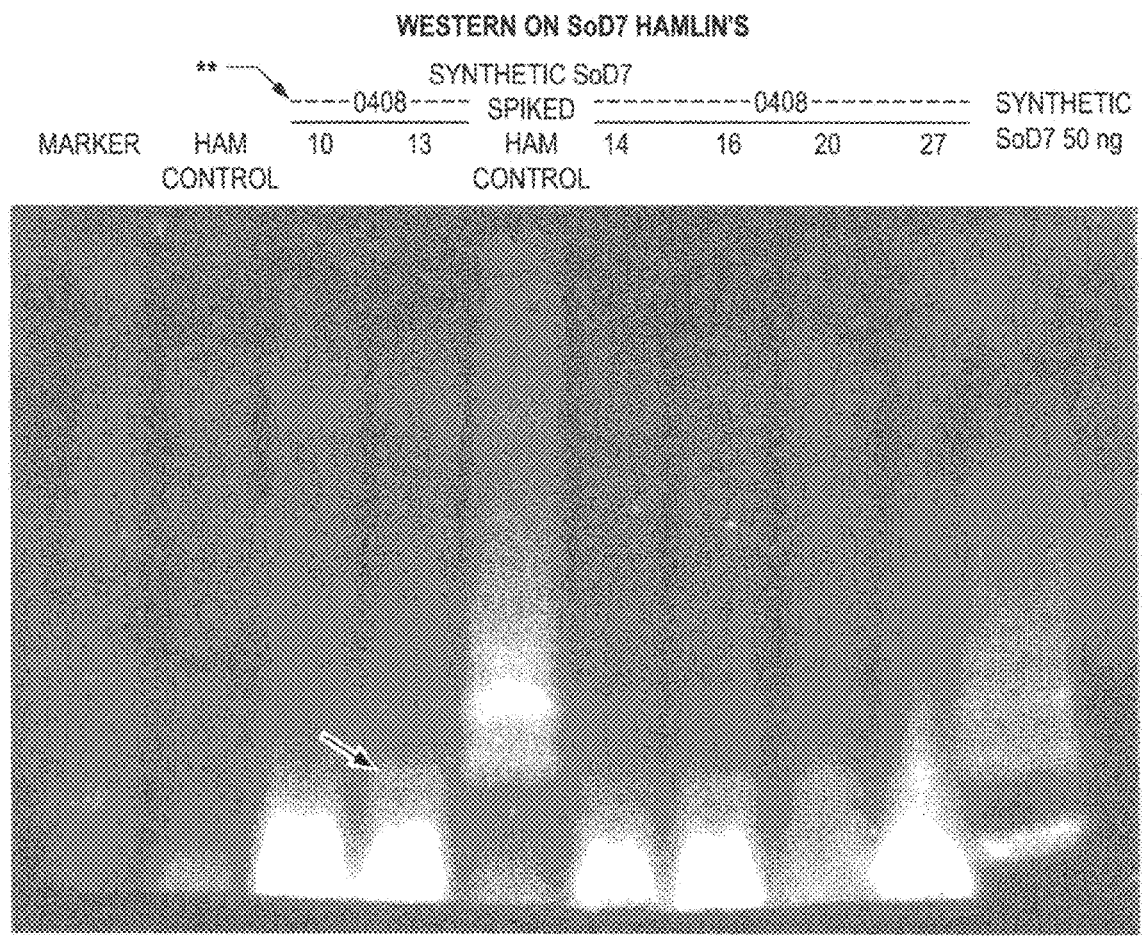
FIG. 19 is a Western blot illustrating binding of an anti-SoD7 according to specific example embodiments of the disclosure to samples containing SoD7.

Antibodies were raised to SoD2 and SoD7. Full length SoD7 peptide was synthesized by GenScript. Aliquots of synthetic SoD7 (200 ug each time) were injected into each of 2 different rabbits every three weeks for a total of 4 injections. Sera was collected 2 weeks after the third and 2 weeks after the fourth injections. IgG was purified using a Protein A column. SoD7 specific IgG was purified by passing the IgG preparation over a column of synthetic SoD7 conjugated to agarose beads and then eluting with a low pH buffer Eluate was screened for binding to a dilution series from 1 ng to 100 ng synthetic SoD7. FIG. 19 is a Western blot illustrating binding of the purified SoD7-specific IgG antibodies to about 20 ng of SoD7 peptide in either transgenic plants (lanes 3, 4, and 6-9), non-transgenic plants spiked with synthetic SoD7 peptide (lane 5), or pure synthetic SoD7 (lane 10).

Example 18: Spinach Defensin Sequences and Codon Optimization

Spinach (*Spinacea oleracea*, viroflay) defensin gene sequences were assembled using next-generation sequencing reads deposited in NCBI sequence read archive (SRA) by employing bioinformatics tools and methods (e.g., Dohm et al., 2013, *Nature*, 505, 546-549; Yao et al., 2005, *Plant Mol. Biol*, 57, 445-460). SEQ ID NOs: 81, 82, 83, 84, 85, and 86 are specific example embodiments of assembled scaffold regions that comprise nucleic acid sequences of spinach (*Spinacia oleracea*) defensin genes. Table 6 illustrates specific example embodiments of assembled scaffold regions, nucleic acid sequences, and peptide sequences of spinach defensins.

TABLE 6

Example embodiments of assembled scaffold regions, nucleic acid sequences, and peptide sequences from Spinach (*Spinacea oleracea*, viroflay) encoding defensin genes.

| Spinach Scaffold Region (SEQ ID NO) | Nucleic Acid Sequence of Defensin Gene (SEQ ID NO) | Genscript Optimized Synthetic Defensin Gene (SEQ ID NO) | VGD Optimized Synthetic Defensin Gene (SEQ ID NO) | Defensin Peptide Sequence (SEQ ID NO) |
|---|---|---|---|---|
| 81 | 39 | 46 | 52 | 32 |
| 82 | 40 | 47 | 53 | 33 |
| 83 | 41 | 48 | 54 | 34 |
| 84 | 42 | NA | 55 | 35 |
| 84 | 43 | 49 | 56 | 36 |
| 85 | 44 | 50 | 57 | 37 |
| 86 | 45 | 51 | 58 | 38 |

SEQ ID NOs: 39, 40, 41, 42, 43, 44, and 45 are specific example embodiments of nucleic acid sequences of spinach (*Spinacia oleracea*) defensin genes, Def1, Def2, Def3, Def4, Def5, Def6, and Def7, respectively.

Nucleic acid sequences encoding defensin genes (e.g. SEQ ID NOS: 39-45) were optimized using the GenScript codon-optimization algorithm available at http://www.genscript.com/codon_opt.html. Briefly, the algorithm uses a complex sorting matrix, including transcription, translation and protein folding, to sift through over 10,000 candidate sequences to identify a predicted best sequence for expression in a given organism. SEQ ID NOs 46, 47, 48, 49, 50, and 51 are specific example embodiments of Genscript codon optimized sequences of SEQ ID NOs: 39, 40, 41, 43, 44, and 45, respectively.

Nucleic acid sequences encoding defensin genes (e.g. SEQ ID NOS: 39-45) were optimized in a two-step approach using the Visual Gene Developer (VGD) platform of Jung S and McDonald K, 2011, *BMC Bioinformatics* 12: 340-353.

First, the sequences were optimized for minimum mRNA secondary structure and binding energy (Gibbs free energy [G]=−0.2 to 0 kcal/base). Next, the optimized mRNA sequences were subjected to favorable synonymous codon optimization using a pre-calculated Codon Adaptation Index (CAI) for *Citrus sinensis* (Csi). The Csi-CAI was calculated from a codon usage matrix generated using data from 116 Csi codon sequences (47126 codons) available in Kazusa codon database (www.kazusa.or.jp/codon). SEQ ID NOs 52, 53, 54, 55, 56, 57, and 58 are specific example embodiments of VGD codon optimized sequences of SEQ ID NOs: 39, 40, 41, 42, 43, 44, and 45, respectively.

Predicted mRNA secondary structures of SEQ ID NOs: 39, 40, 41, 42, 43, 44, and 45, may be constructed using the Visual Gene Developer platform of Jung S and McDonald K, 2011, *BMC Bioinformatics* 12: 340-353.

Example 19: SEQ ID NOS 32, 33, 34, 35, 36, 37, and 38 Peptide Sequence Alignment SEQ ID NOs: 32, 33, 34, 35, 36, 37, and 38 are specific example embodiments of defensin peptide sequences from spinach (*Spinacia oleracea*).

Figure 20:
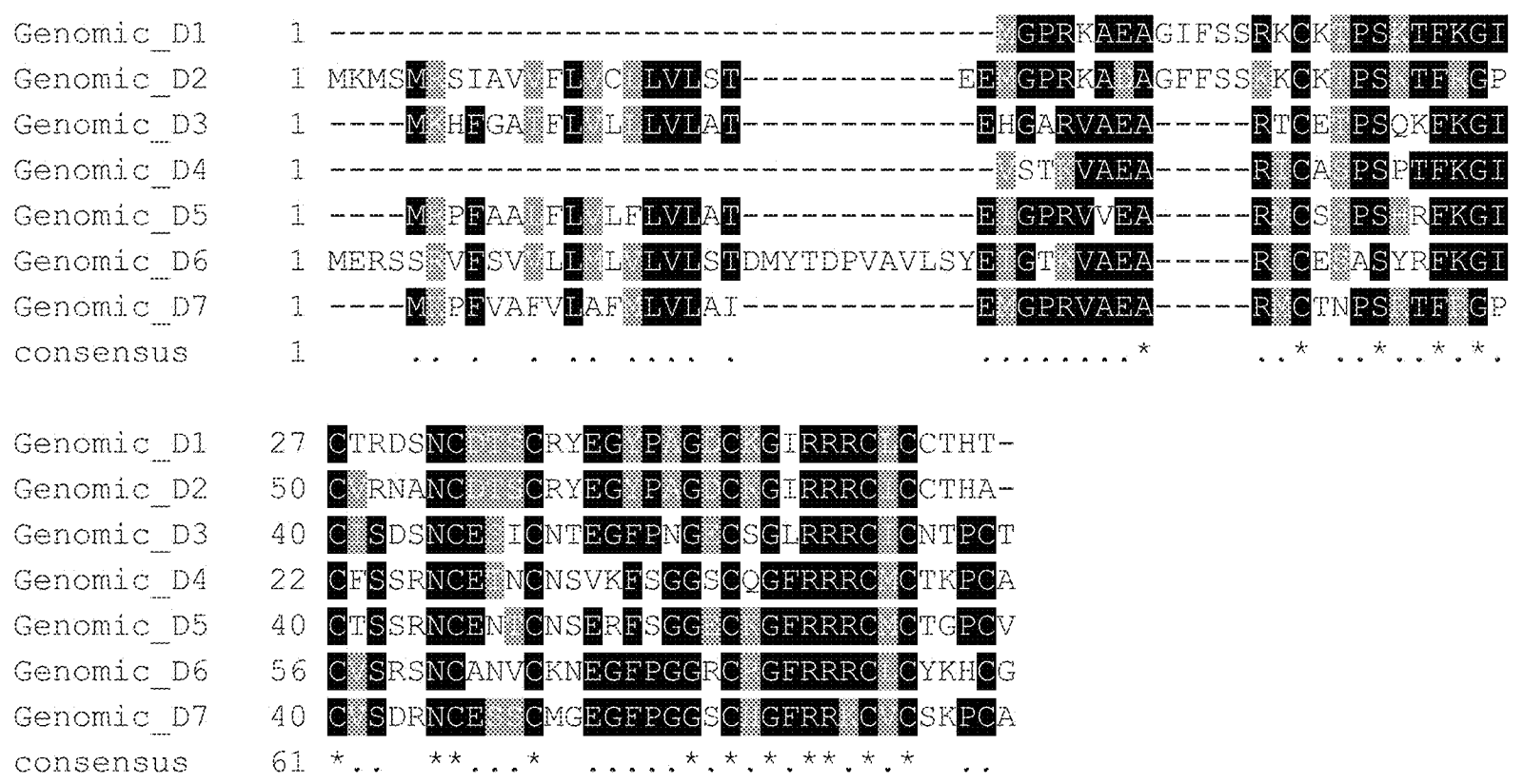

Multiple sequence alignment of SEQ ID NO: 32 (Genomic D1), SEQ ID NO: 33 (Genomic D2), SEQ ID NO: 34 (Genomic D3), SEQ ID NO: 35 (Genomic D4), SEQ ID NO: 36 (Genomic D5), SEQ ID NO: 37 (Genomic D6), and SEQ ID NO: 38 (Genomic D7) was performed using ClustalW. FIG. 20 illustrates the resulting alignment of the spinach defensin peptides. The consensus symbols are indicated below the alignments with identically conserved residues indicated by black shading and an asterisk. Amino acids with ≥50% identity are shaded gray and marked with a period.

Figure 21A:
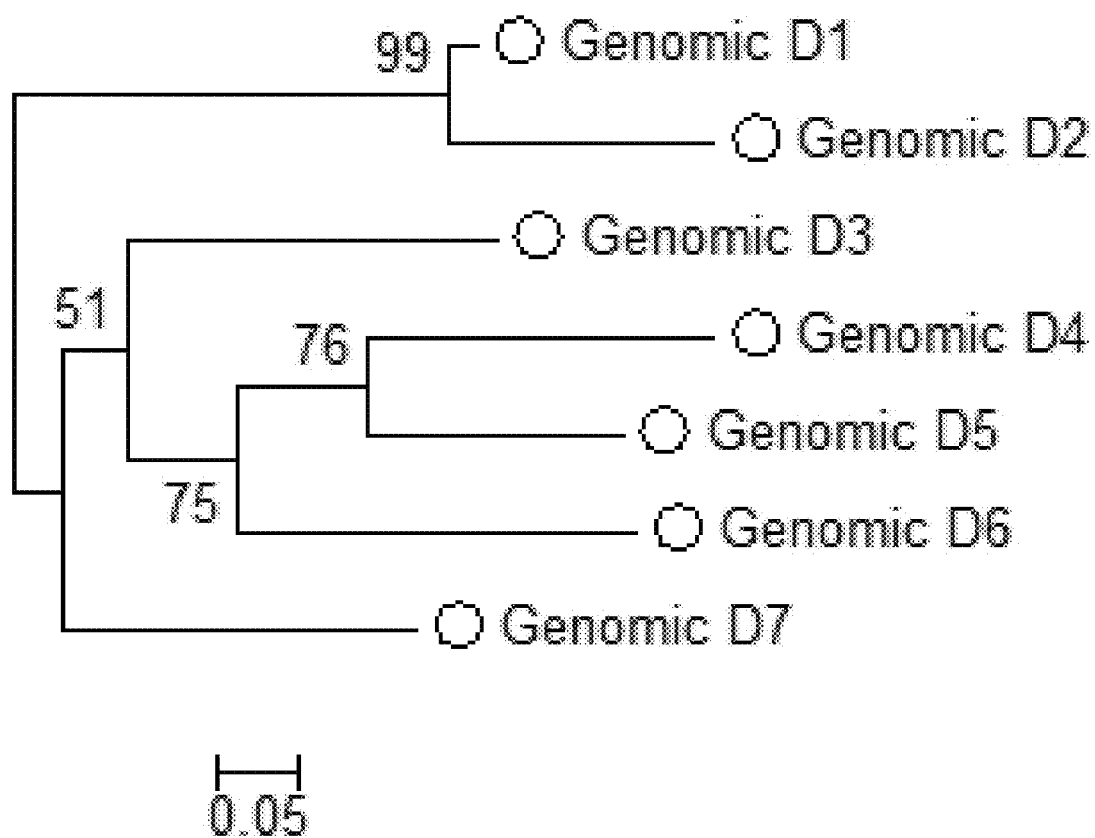
FIG. 21A is a representation of the results of phylogenetic analyses of SEQ ID NOS 32, 33, 34, 35, 36, 37, and 38 according to a specific example embodiment of the disclosure.
Figure 21B:
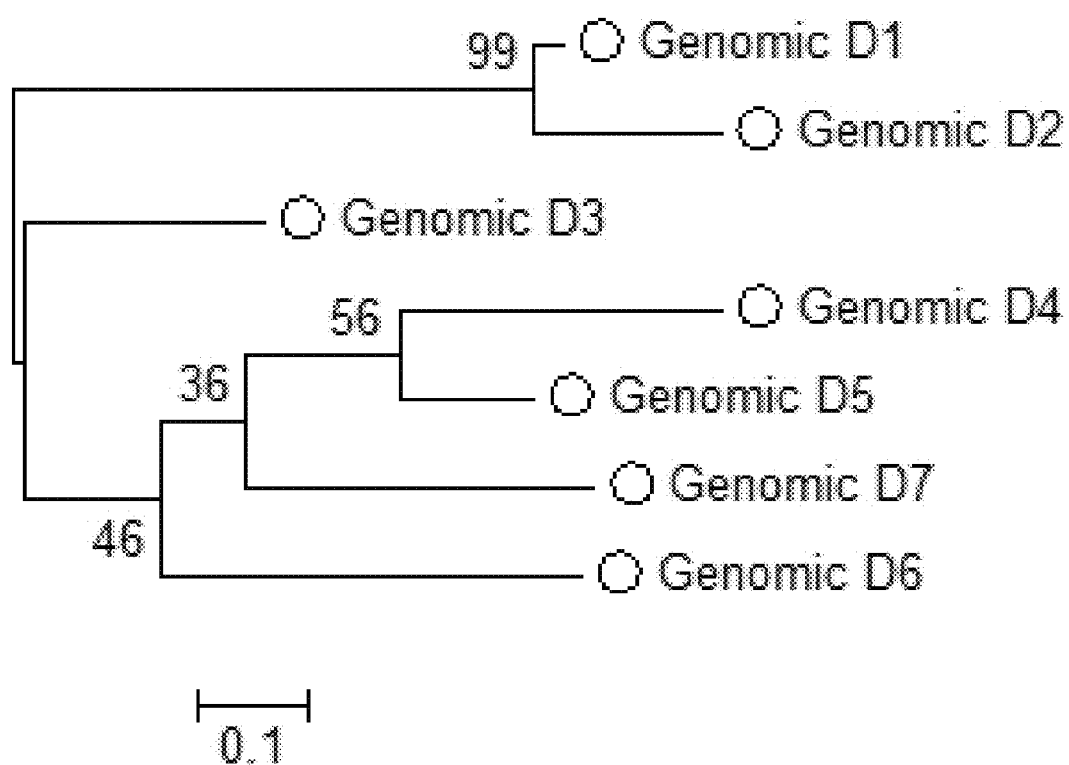
FIG. 21B is a representation of the results of phylogenetic analyses of SEQ ID NOS 32, 33, 34, 35, 36, 37, and 38 according to a specific example embodiment of the disclosure.

FIG. 21A and FIG. 21B illustrate the results of phylogenetic analyses of SEQ ID NOs: 32, 33, 34, 35, 36, 37, and 38. Using the sequence alignment from FIG. 20, tree construction was performed following (A) the Neighbor Joining method as illustrated in FIG. 21A, and (B) the Maximum Likelihood method as illustrated in FIG. 21B.

In the neighbor joining analysis shown in FIG. 21A, optimal tree topology with a minimum sum of branch length value settings were selected. A Bootstrap test with 1000 replicates resulted in the percentage of replicate trees in which associated taxa clustered together. These values are indicated next to their respective branches in FIG. 21A. Branch length units indicate the number of amino acid substitutions per site, and represent evolutionary distances as computed using the Poisson correction method.

FIG. 21B illustrates a maximum likelihood tree wherein the tree topology with the highest log likelihood is shown. The heuristic search was performed using initial tree(s) generated using the Neighbor-Join and BioNJ algorithms to a matrix of pairwise distances under the JTT substitution model, followed by selection of a tree topology with superior log likelihood value.

Example 21: Peptide Sequence Analysis of Spinach Defensins

Figure 22:
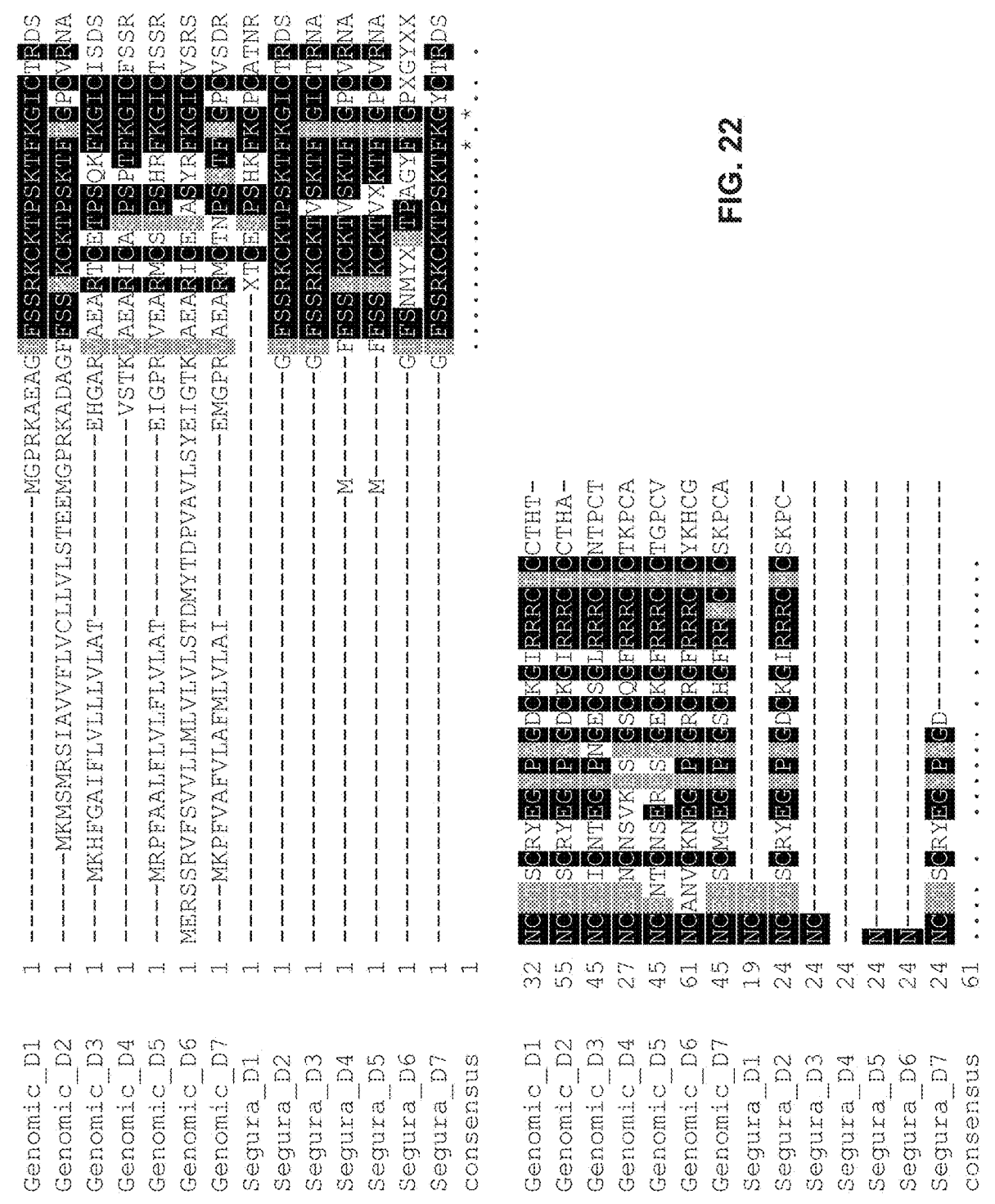

Multiple sequence alignment of SEQ ID NO: 32 (Genomic D1), SEQ ID NO: 33 (Genomic D2), SEQ ID NO: 34 (Genomic D3), SEQ ID NO: 35 (Genomic D4), SEQ ID NO: 36 (Genomic D5), SEQ ID NO: 37 (Genomic D6), SEQ ID NO: 38 (Genomic D7), and reported spinach defensin subfamily IV sequences (Segura D1-Segura D7) as described by Segura, A. et al., 1998, *FEBS Letters* 435: 159-162 was performed using ClustalW. FIG. 22 illustrates the resulting alignment. The consensus symbols are indicated below the alignments with identically conserved residues indicated by black shading and an asterisk. Amino acids with ≥50% identity are shaded gray and marked with a period.

Phylogenetic analyses were performed using the multiple sequence alignment illustrated in FIG. 22. Tree construction was performed using (A) the Neighbor Joining method as illustrated in FIG. 23A, and (B) the Maximum Likelihood method as illustrated in FIG. 23B.

Figure 23A:
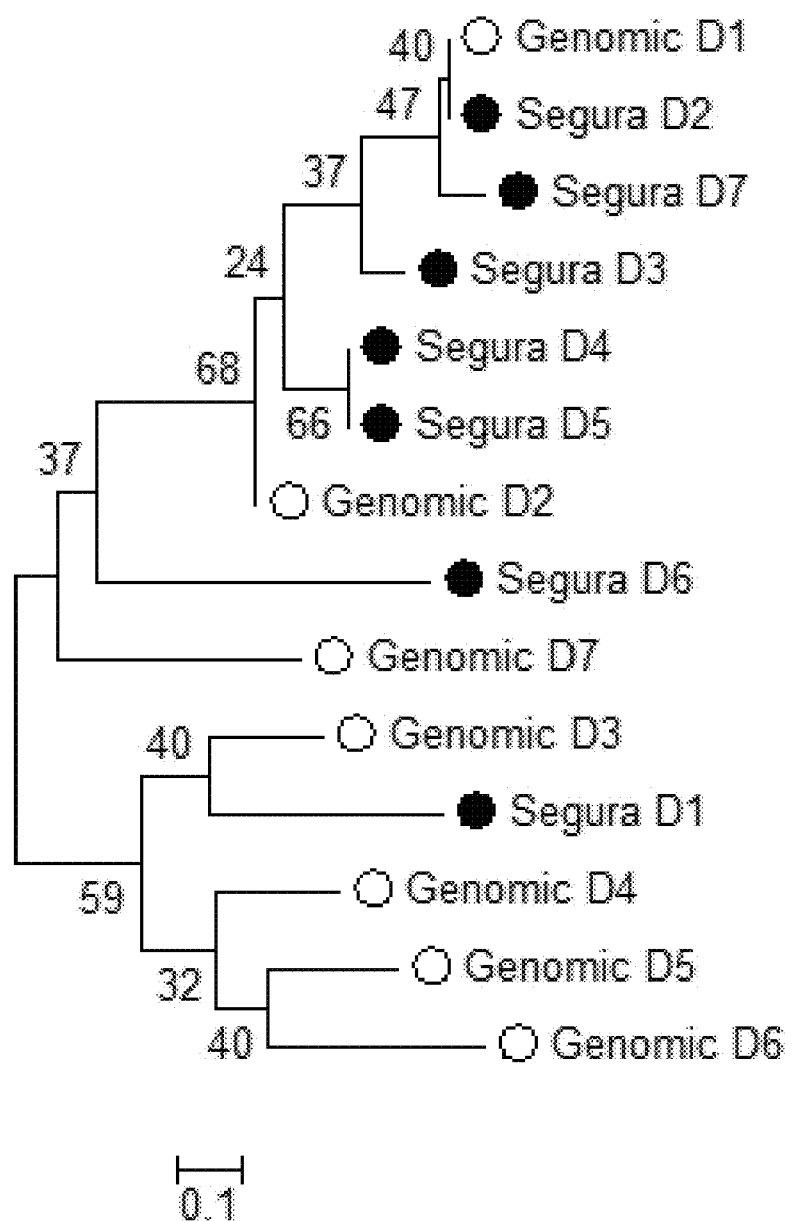
FIG. 23A is a representation of the results of phylogenetic analyses of SEQ ID NOS 32, 33, 34, 35, 36, 37, 38, and group IV defensin sequences according to a specific example embodiment of the disclosure.

In the neighbor joining analysis shown in FIG. 23A, optimal tree topology with a minimum sum of branch length value settings were selected. A Bootstrap test with 1000 replicates resulted in the percentage of replicate trees in which associated taxa clustered together. These values are indicated next to their respective branches in FIG. 23A. Branch length units indicate the number of amino acid substitutions per site, and represent evolutionary distances as computed using the Poisson correction method.

Figure 23B:
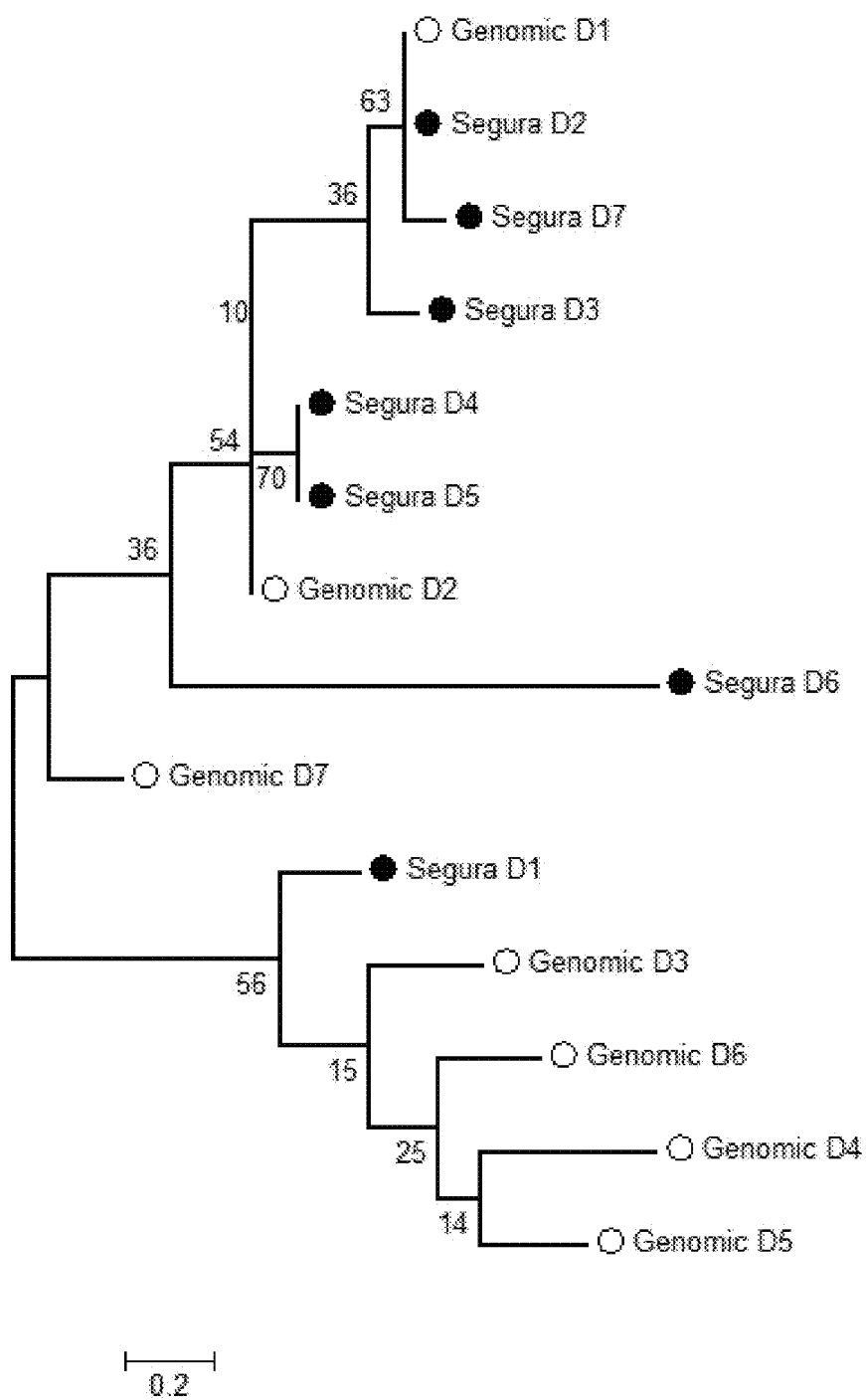
FIG. 23B is a representation of the results of phylogenetic analyses of SEQ ID NOS 32, 33, 34, 35, 36, 37, 38, and group IV defensin sequences according to a specific example embodiment of the disclosure.

FIG. 23B illustrates a maximum likelihood tree wherein the tree topology with the highest log likelihood is shown. The heuristic search was performed using initial tree(s) generated using the Neighbor-Join and BioNJ algorithms to a matrix of pairwise distances under the JTT substitution model, followed by selection of a tree topology with superior log likelihood value.

Example 22: Peptide Sequence Analysis of Defensins

Multiple sequence alignment was performed using ClustalW to compare the following peptide sequences: SEQ ID NO: 32 (Genomic D1); SEQ ID NO: 33 (Genomic D2); SEQ ID NO: 34 (Genomic D3); SEQ ID NO: 35 (Genomic D4); SEQ ID NO: 36 (Genomic D5); SEQ ID NO: 37 (Genomic D6); SEQ ID NO: 38 (Genomic D7); reported spinach defensin subfamily IV sequences (Segura D1-Segura D7) as described by Segura, A. et al., 1998, *FEBS Letters* 435: 159-162; representative group I defensin sequences (Rs-AFP2, At-AFP1, Hs-AFP1) as illustrated in Segura et al.; representative group II defensin sequences (Ah-Amp1), Dm-AMP1) as illustrated in Segura et al.; and representative group III defensing sequences (St-PTH1, SIalpha2) as illustrated in Segura et. al. FIG. 24 illustrates the resulting alignment. The consensus symbols are indicated below the alignments with identically conserved residues indicated by black shading and an asterisk. Amino acids with ≥50% identity are shaded gray and marked with a period.

Phylogenetic analyses were performed using the multiple sequence alignment illustrated in FIG. 24. Tree construction was performed using (A) the Neighbor Joining method as illustrated in FIG. 25A, and (B) the Maximum Likelihood method as illustrated in FIG. 25B.

Figure 25A:
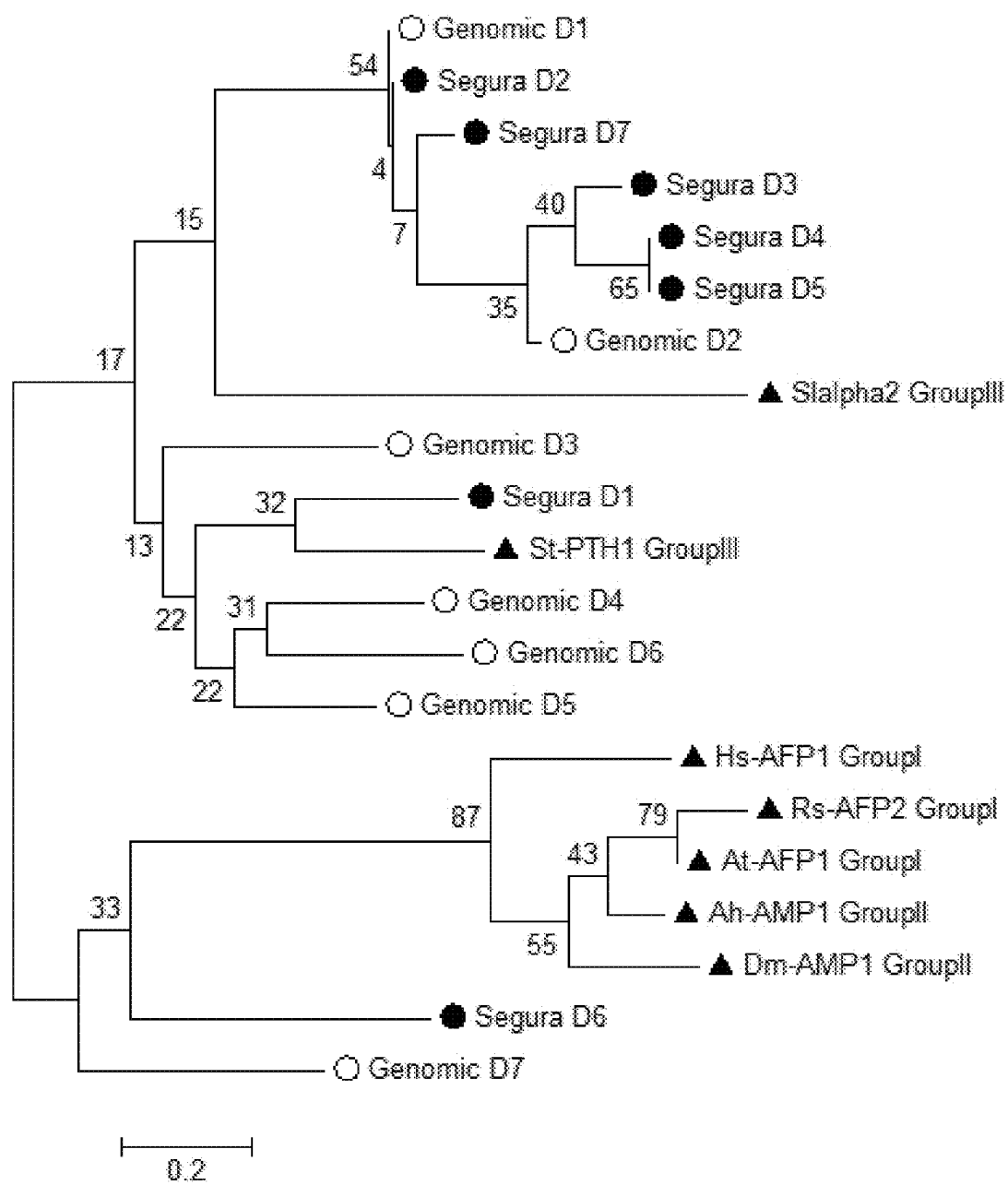
FIG. 25A is a representation of the results of phylogenetic analyses of SEQ ID NOS 32, 33, 34, 35, 36, 37, 38, and representative defensin sequences from groups I, II, III, and IV according to a specific example embodiment of the disclosure.

In the neighbor joining analysis shown in FIG. 25A, optimal tree topology with a minimum sum of branch length value settings were selected. A Bootstrap test with 1000 replicates resulted in the percentage of replicate trees in which associated taxa clustered together. These values are indicated next to their respective branches in FIG. 25A. Branch length units indicate the number of amino acid substitutions per site, and represent evolutionary distances as computed using the Poisson correction method.

Figure 25B:
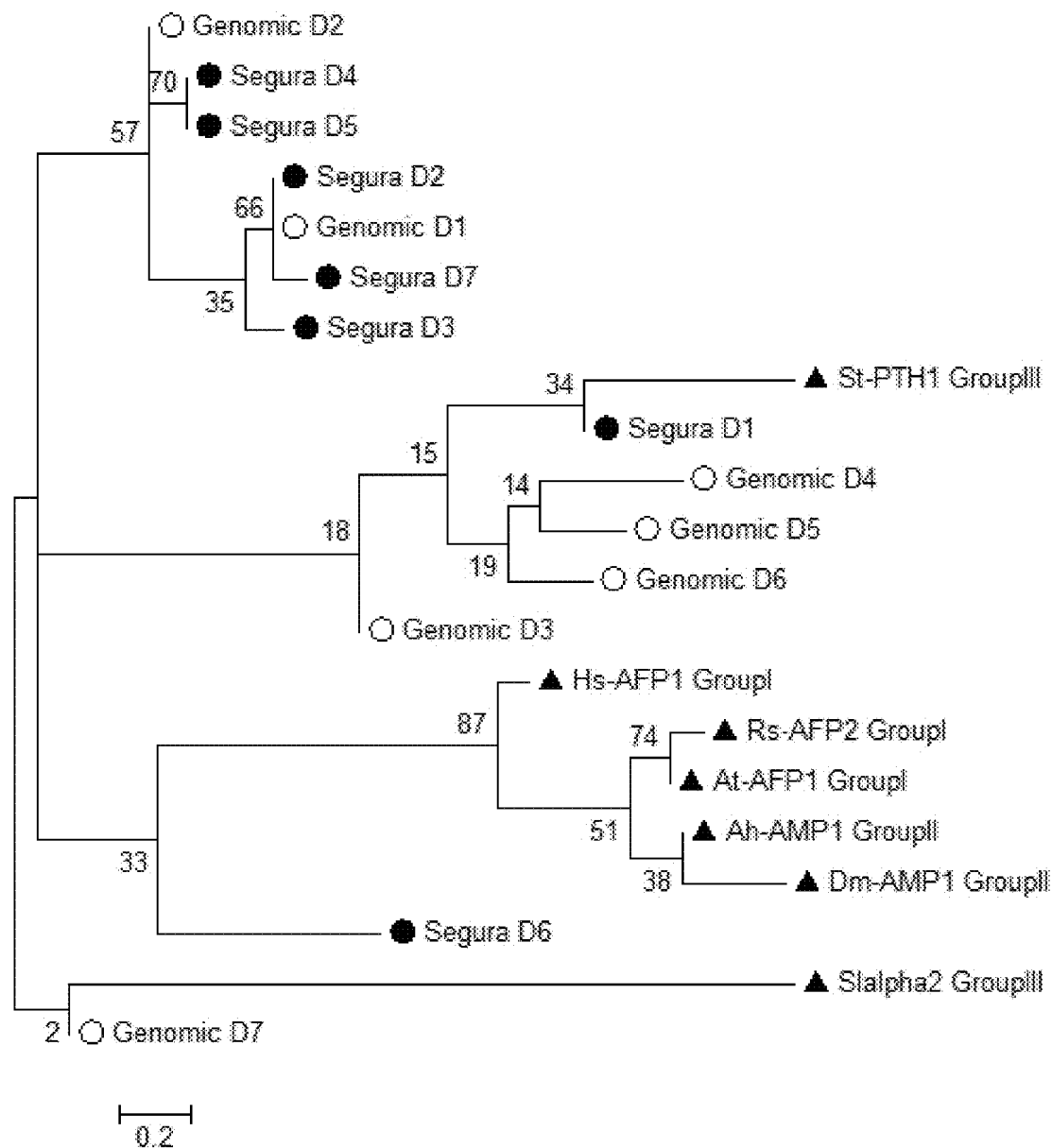
FIG. 25B is a representation of the results of phylogenetic analyses of SEQ ID NOS 32, 33, 34, 35, 36, 37, 38, and representative defensin sequences from groups I, II, III, and IV according to a specific example embodiment of the disclosure.

FIG. 25B illustrates a maximum likelihood tree wherein the tree topology with the highest log likelihood is shown. The heuristic search was performed using initial tree(s) generated using the Neighbor-Join and BioNJ algorithms to a matrix of pairwise distances under the JTT substitution model, followed by selection of a tree topology with superior log likelihood value.

Example 23: Constructs

Table 7 illustrates specific example embodiments of chimeric nucleic acid sequences encoding a signal peptide and a defensin gene codon-optimized for citrus. Signal peptides and structural gene coding sequences shown are flanked on either side by specific restriction enzyme sites. These sequences were used to construct expression cassettes, vectors, and transformed *Agrobacterium* for preparation of transgenic plants.

TABLE 7

Example embodiments of chimeric nucleotide sequences of defensin genes. The nucleotide sequences were optimized for codon usage in Citrus.

| Defensin Gene | Source of the Optimized Synthetic Gene (SEQ ID NO) | A chimeric nucleotide sequence. The 5' nucleotides include the cloning site and a preferred context for the start codon. The 3' nucleotides include the cloning site. |
|---|---|---|
| Def2 | GenScript (47) | SEQ ID NO: 59 |
|  | VGD (53) | SEQ ID NO: 60 |

Figure 26A:
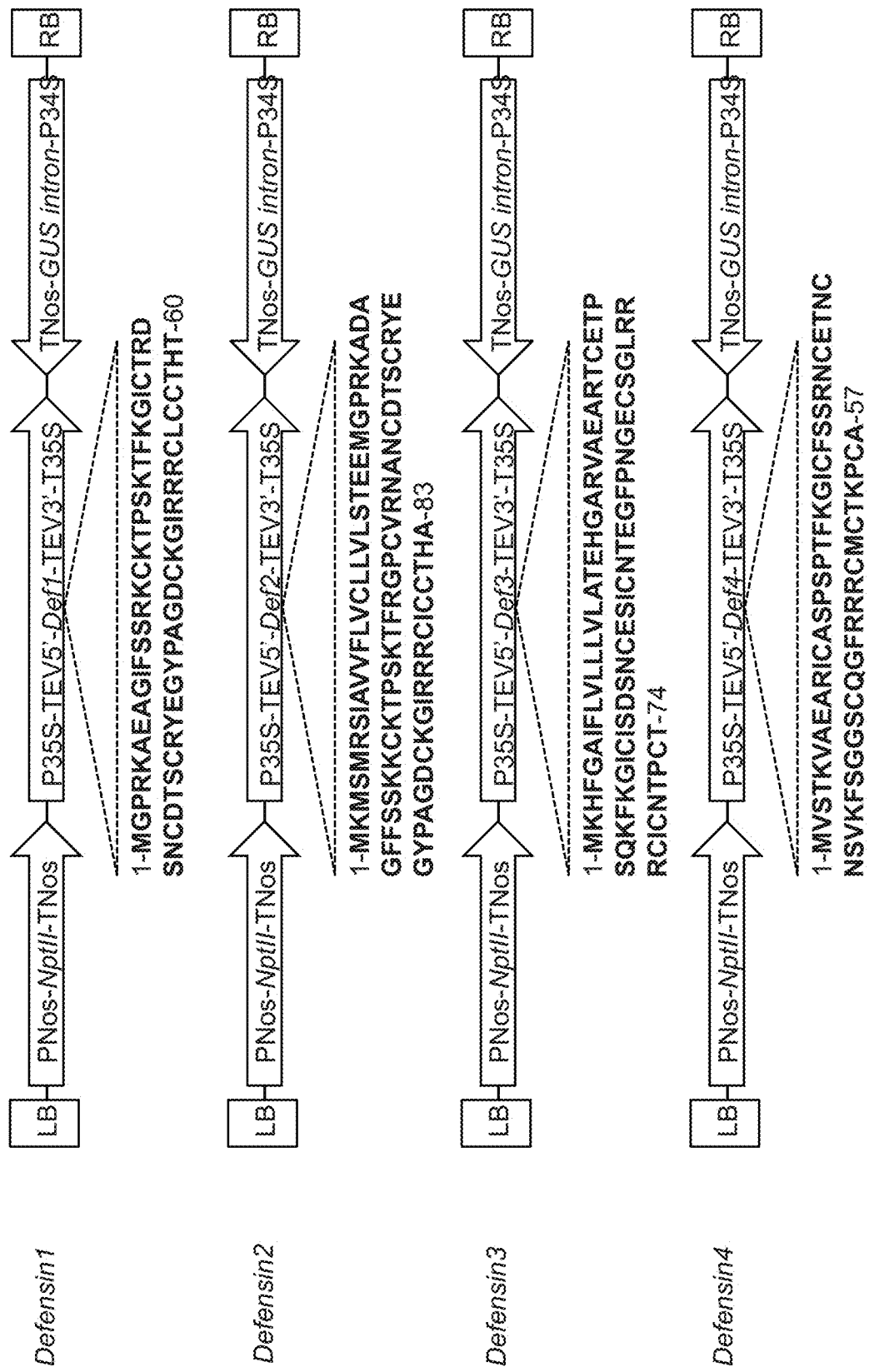
FIG. 26A illustrates expression cassettes encoding individual defensin genes codon optimized for citrus including Def1 (SEQ ID NO: 32), Def2 (Seq ID NO: 33), Def3 (SEQ ID NO: 34), and Def 4 (SEQ ID NO: 35), according to a specific example embodiment of the disclosure.
Figure 26B:
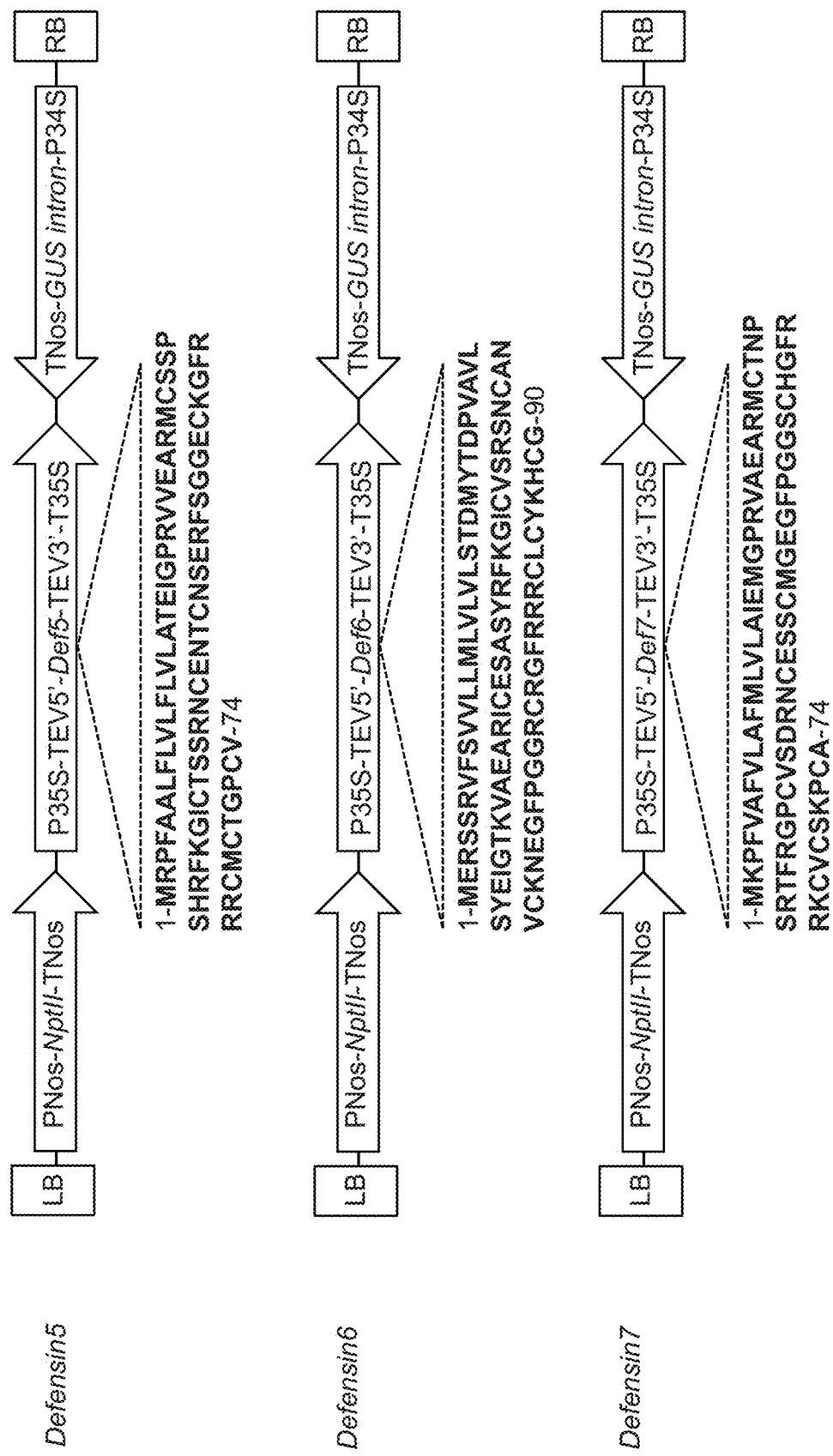
FIG. 26B illustrates expression cassettes encoding individual defensin genes codon optimized for citrus, including Def5 (SEQ ID NO: 36), Def6 (Seq ID NO: 37), and Def7 (SEQ ID NO: 38), according to a specific example embodiment of the disclosure.
Figure 27:
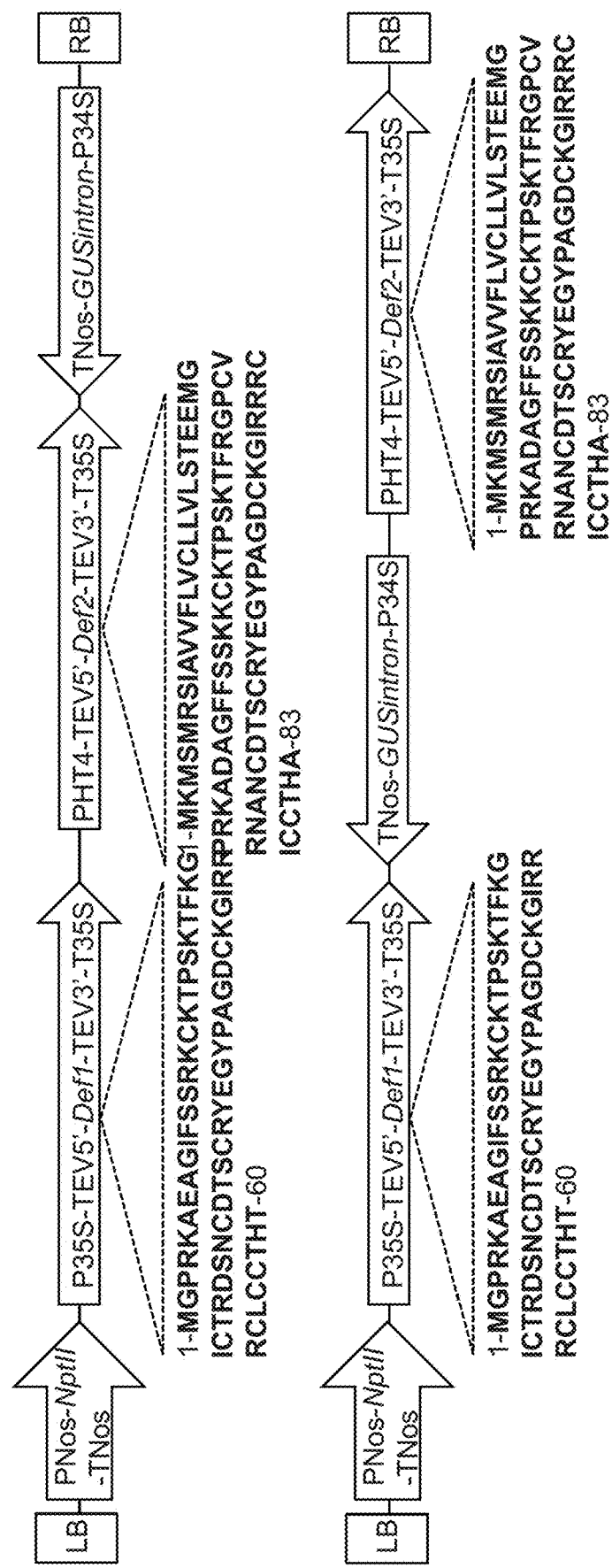
FIG. 27 illustrates expression cassettes for the co-expression of multiple defensin genes codon-optimized for citrus, including Def1 (SEQ ID NO: 32), Def2 (Seq ID NO: 33), according to a specific example embodiment of the disclosure.

FIG. 26A and FIG. 26B illustrate specific example embodiments of expression cassettes encoding a defensin gene codon-optimized for citrus. Upstream of the defensin gene coding sequences is a promoter sequence, a translational enhancer, and a XbaI restriction enzyme site. While downstream of the defensin gene coding sequence is a KpnI restriction enzyme site, a translational enhancer, and a terminator sequence. The entire construct is flanked by the left and right borders of the Ti plasmid. FIG. 27 illustrates specific example embodiments of expression cassettes encoding a multiple defensin genes, with each defensin gene codon-optimized for citrus. FIG. 28 illustrates the potential combinations for co-expression of spinach defensins.

Example 24: Constructs

Examples of successful generation of transgenic plants achieved using the compositions and methods of the disclosure are shown in Tables 8 and 9.

TABLE 8

Citrus

| Genomic Spinach Defensin Expression Construct | Number of Transgenic Events | Variety-Citrus |
|---|---|---|
| Defensin 1 | 1 | Mexican Lime |
| Defensin 3 | 1 | Mexican Lime |
| Defensin 5 | 4 | Mexican Lime |
| Defensin 6 | 4 | Mexican Lime |
| Defensin 3 | 2 | Sour Orange (root stock) |
| Defensin 6 | 2 | Sour Orange (root stock) |
| Defensin 1 | 8 | Frost Lisbon Lemon |
| Defensin 2 | 11 | Frost Lisbon Lemon |

TABLE 9

| Potato | | |
|---|---|---|
| Genomic Spinach Defensin Expression Construct | Number of Transgenic Events | Variety-Potato |
| Defensin 1 | 4 | Atlantic |
| Defensin 2 | 6 | Atlantic |
| Defensin 3 | 2 | Atlantic |
| Defensin 5 | 8 | Atlantic |
| Defensin 6 | 8 | Atlantic |
| Defensin 7 | 2 | Atlantic |

What is claimed is:

1. A citrus plant comprising at least one defensin peptide comprising a first defensin peptide, wherein the amino acid sequence of the first defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38; wherein the peptide has antimicrobial activity in the citrus plant.

2. The citrus plant according to claim 1, wherein the amino acid sequence of the first defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38.

3. The citrus plant according to claim 1, wherein the amino acid sequence of the first defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38.

4. The citrus plant according to claim 1 further comprising a second defensin peptide, wherein the amino acid sequence of the second defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38.

5. The citrus plant according to claim 4, wherein the amino acid sequence of the second defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38.

6. The citrus plant according to claim 4, wherein the amino acid sequence of the second defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38.

7. The citrus plant according to claim 4, wherein the amino acid sequence of the first defensin peptide and the amino acid sequence of the second defensin peptide are different.

8. The citrus plant according to claim 1, wherein the plant is orange, grapefruit, lemon, or lime.

9. A citrus plant comprising at least one defensin nucleic acid comprising a first defensin nucleic acid, wherein the nucleic acid sequence of the first defensin nucleic acid is at least 98% identical to SEQ ID NO: 46, at least 98% identical to SEQ ID NO: 47, at least 98% identical to SEQ ID NO: 48, at least 98% identical to SEQ ID NO: 49, at least 98% identical to SEQ ID NO: 50, at least 98% identical to SEQ ID NO: 51, at least 98% identical to SEQ ID NO: 52, at least 98% identical to SEQ ID NO: 53, at least 98% identical to SEQ ID NO: 54, at least 98% identical to SEQ ID NO: 55, at least 98% identical to SEQ ID NO: 56, at least 98% identical to SEQ ID NO: 57, or at least 98% identical to SEQ ID NO: 58; wherein the first nucleic acid encodes a peptide having antimicrobial activity in the citrus plant.

10. The citrus plant according to claim 9, wherein the nucleic acid sequence of the first defensin nucleic acid is at least 99% identical to SEQ ID NO: 46, at least 99% identical to SEQ ID NO: 47, at least 99% identical to SEQ ID NO: 48, at least 99% identical to SEQ ID NO: 49, at least 99% identical to SEQ ID NO: 50, at least 99% identical to SEQ ID NO: 51, at least 99% identical to SEQ ID NO: 52, at least 99% identical to SEQ ID NO: 53, at least 99% identical to SEQ ID NO: 54, at least 99% identical to SEQ ID NO: 55, at least 99% identical to SEQ ID NO: 56, at least 99% identical to SEQ ID NO: 57, or at least 99% identical to SEQ ID NO: 58.

11. The citrus plant according to claim 9, wherein the nucleic acid sequence of the first defensin nucleic acid is 100% identical to the nucleic acid sequence of SEQ ID NO: 46, 100% identical to the nucleic acid sequence of SEQ ID NO: 47, 100% identical to the nucleic acid sequence of SEQ ID NO: 48, 100% identical to the nucleic acid sequence of SEQ ID NO: 49, 100% identical to the nucleic acid sequence of SEQ ID NO: 50, 100% identical to the nucleic acid sequence of SEQ ID NO: 51, 100% identical to the nucleic acid sequence of SEQ ID NO: 52, 100% identical to the nucleic acid sequence of SEQ ID NO: 53, 100% identical to the nucleic acid sequence of SEQ ID NO: 54, 100% identical to the nucleic acid sequence of SEQ ID NO: 55, 100% identical to the nucleic acid sequence of SEQ ID NO: 56, 100% identical to the nucleic acid sequence of SEQ ID NO: 57, or 100% identical to the nucleic acid sequence of SEQ ID NO: 58.

12. The citrus plant according to claim 9 further comprising a second defensin nucleic acid,
wherein the nucleic acid sequence of the second defensin nucleic acid is at least 98% identical to SEQ ID NO: 46, at least 98% identical to SEQ ID NO: 47, at least 98% identical to SEQ ID NO: 48, at least 98% identical to SEQ ID NO: 49, at least 98% identical to SEQ ID NO: 50, at least 98% identical to SEQ ID NO: 51, or at least 98% identical to SEQ ID NO: 52, at least 98% identical to SEQ ID NO: 53, at least 98% identical to SEQ ID NO: 54, at least 98% identical to SEQ ID NO: 55, at least 98% identical to SEQ ID NO: 56, at least 98% identical to SEQ ID NO: 57, or at least 98% identical to SEQ ID NO: 58.

13. The citrus plant according to claim 9 further comprising a second defensin nucleic acid,
wherein the nucleic acid sequence of the second defensin nucleic acid is at least 99% identical to SEQ ID NO: 46, at least 99% identical to SEQ ID NO: 47, at least 99% identical to SEQ ID NO: 48, at least 99% identical to SEQ ID NO: 49, at least 99% identical to SEQ ID NO: 50, at least 99% identical to SEQ ID NO: 51, or at least 99% identical to SEQ ID NO: 52, at least 99% identical to SEQ ID NO: 53, at least 99% identical to SEQ ID NO: 54, at least 99% identical to SEQ ID NO: 55, at least 99% identical to SEQ ID NO: 56, at least 99% identical to SEQ ID NO: 57, or at least 99% identical to SEQ ID NO: 58.

14. The citrus plant according to claim 9 further comprising a second defensin nucleic acid,
wherein the nucleic acid sequence of the second defensin nucleic acid is 100% identical to SEQ ID NO: 46, 100% identical to SEQ ID NO: 47, 100% identical to SEQ ID NO: 48, 100% identical to SEQ ID NO: 49, 100% identical to SEQ ID NO: 50, 100% identical to SEQ ID NO: 51, 100% identical to SEQ ID NO: 52, 100% identical to SEQ ID NO: 53, 100% identical to SEQ ID NO: 54, 100% identical to SEQ ID NO: 55, 100% identical to SEQ ID NO: 56, 100% identical to SEQ ID NO: 57, or 100% identical to SEQ ID NO: 58.

15. The citrus plant according to claim 12, wherein the nucleic acid sequence of the first defensin nucleic acid and the nucleic acid sequence of the second defensin nucleic acid are different.

16. The citrus plant according to claim 9, wherein the plant is orange, grapefruit, lemon, or lime.

17. A citrus composition comprising at least one defensin peptide comprising a first defensin peptide, wherein the amino acid sequence of the first defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38; wherein the peptide has antimicrobial activity in the citrus composition.

18. The citrus composition according to claim 17, wherein the amino acid sequence of the first defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38.

19. The citrus composition according to claim 17, wherein the amino acid sequence of the first defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38.

20. The citrus composition according to claim 17 further comprising a second defensin peptide, wherein the amino acid sequence of the second defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38.

21. The citrus composition according to claim 20, wherein the amino acid sequence of the second defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38.

22. The citrus composition according to claim 20, wherein the amino acid sequence of the second defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38.

23. The citrus composition according to claim 20, wherein the amino acid sequence of the first defensin peptide and the amino acid sequence of the second defensin peptide are different.

* * * * *

SEQUENCE LISTING

```
<160> NUMBER OF SEQ ID NOS: 102

<210> SEQ ID NO 1
<211> LENGTH: 52
<212> TYPE: PRT
<213> ORGANISM: Spinacia oleracea
<220> FEATURE:
<221> NAME/KEY: mat_peptide
<222> LOCATION: (1)..(52)
<223> OTHER INFORMATION: SoD2 peptide

<400> SEQUENCE: 1

Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Gly Tyr Pro Ala Gly Asp Cys Lys Gly Ile Arg Arg Arg Cys Met Cys
        35                  40                  45

Ser Lys Pro Cys
    50

<210> SEQ ID NO 2
<211> LENGTH: 38
<212> TYPE: PRT
<213> ORGANISM: Spinacia oleracea
<220> FEATURE:
<221> NAME/KEY: mat_peptide
<222> LOCATION: (1)..(38)
<223> OTHER INFORMATION: SoD7 peptide

<400> SEQUENCE: 2

Gly Ile Phe Ser Ser Arg Lys Cys Lys Thr Pro Ser Lys Thr Phe Lys
1               5                   10                  15

Gly Tyr Cys Thr Arg Asp Ser Asn Cys Asp Thr Ser Cys Arg Tyr Glu
            20                  25                  30

Gly Tyr Pro Ala Gly Asp
        35

<210> SEQ ID NO 3
<211> LENGTH: 162
<212> TYPE: DNA
<213> ORGANISM: Artificial Sequence
<220> FEATURE:
<223> OTHER INFORMATION: SoD2 codon-optimized with GenScript

<400> SEQUENCE: 3
ggtattttct catctaggaa gtgcaaaact ccttcaaaga cttttaaggg aatttgcact      60
agggattcta attgcgatac ttcttgcaga tacgagggat atccagctgg cgattgcaaa    120
ggaattagga ggagatgtat gtgttcaaag ccatgttaat aa                      162

<210> SEQ ID NO 4
```

```
<211> LENGTH: 120
<212> TYPE: DNA
<213> ORGANISM: Artificial Sequence
<220> FEATURE:
<223> OTHER INFORMATION: SoD7 codon-optimized with GenScript

<400> SEQUENCE: 4
ggaattttct cttcaaggaa gtgcaagact ccatctaaga ctttcaaggg atattgtact    60
agggattcta actgcgatac atcatgcaga tacgagggct atcctgctgg cgattaataa   120

<210> SEQ ID NO 5
<211> LENGTH: 162
<212> TYPE: DNA
<213> ORGANISM: Artificial Sequencce
<220> FEATURE:
<223> OTHER INFORMATION: SoD2 codon-optimized with CODA

<400> SEQUENCE: 5 ggtatcttt ctagtagaaa gtgtaagact ccttctaaga cttttaaagg tatttgcact    60
agagattcta attgtgacac ttcttgtaga tatgaaggtt atcctgctgg tgattgtaag   120
ggtattagaa gaagatgtat gtgttctaag ccttgttaat ag                     162

<210> SEQ ID NO 6
<211> LENGTH: 120
<212> TYPE: DNA
<213> ORGANISM: Artificial Sequence
<220> FEATURE:
<223> OTHER INFORMATION: SoD7 codon-optimized with CODA

<400> SEQUENCE: 6
ggtatttttt catctcgtaa gtgtaagact ccttctaaga cttttaaggg ttattgcact    60
agagattcta attgtgatac atcttgtaga tatgaaggtt atcctgctgg tgattaatag   120

<210> SEQ ID NO 7
<211> LENGTH: 82
<212> TYPE: PRT
<213> ORGANISM: Artificial Sequence
<220> FEATURE:
<223> OTHER INFORMATION: Chimeric peptide comprising a signal peptide
      and SoD2
<220> FEATURE:
<221> NAME/KEY: Signal
<222> LOCATION: (1)..(30)
<223> OTHER INFORMATION: PR-1b signal peptide
<220> FEATURE:
<221> NAME/KEY: mat_peptide
<222> LOCATION: (31)..(82)
<223> OTHER INFORMATION: SoD2 peptide

<400> SEQUENCE: 7

Met Gly Phe Phe Leu Phe Ser Gln Met Pro Ser Phe Leu Val Ser
-30                 -25                 -20                 -15

Thr Leu Leu Leu Phe Leu Ile Ile Ser His Ser Ser His Ala Gly Ile
                -10                  -5                  -1   1

Phe Ser Ser Arg Lys Cys Lys Thr Pro Ser Lys Thr Phe Lys Gly Ile
                  5                  10                  15

Cys Thr Arg Asp Ser Asn Cys Asp Thr Ser Cys Arg Tyr Glu Gly Tyr
             20                  25                  30

Pro Ala Gly Asp Cys Lys Gly Ile Arg Arg Arg Cys Met Cys Ser Lys
35                  40                  45                  50

Pro Cys

<210> SEQ ID NO 8
```

```
<211> LENGTH: 68
<212> TYPE: PRT
<213> ORGANISM: Artificial Sequence
<220> FEATURE:
<223> OTHER INFORMATION: Chimeric peptide comprising a signal peptide
      and SoD7
<220> FEATURE:
<221> NAME/KEY: Signal
<222> LOCATION: (1)..(30)
<223> OTHER INFORMATION: PR-1b signal peptide
<220> FEATURE:
<221> NAME/KEY: mat_peptide
<222> LOCATION: (31)..(68)
<223> OTHER INFORMATION: SoD7 peptide

<400> SEQUENCE: 8

Met Gly Phe Phe Leu Phe Ser Gln Met Pro Ser Phe Phe Leu Val Ser
-30              -25                 -20                 -15

Thr Leu Leu Leu Phe Leu Ile Ile Ser His Ser His Ala Gly Ile
            -10                 -5                  -1   1

Phe Ser Ser Arg Lys Cys Lys Thr Pro Ser Lys Thr Phe Lys Gly Tyr
            5                   10                  15

Cys Thr Arg Asp Ser Asn Cys Asp Thr Ser Cys Arg Tyr Glu Gly Tyr
            20                  25                  30

Pro Ala Gly Asp
35

<210> SEQ ID NO 9
<211> LENGTH: 268
<212> TYPE: DNA
<213> ORGANISM: Artificial Sequence
<220> FEATURE:
<223> OTHER INFORMATION: Chimeric nucleic acid encoding a signal peptide
      and SoD2 codon-optimized with GenScript
<220> FEATURE:
<221> NAME/KEY: misc_feature
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
<221> NAME/KEY: misc_feature
<222> LOCATION: (101)..(256)
<223> OTHER INFORMATION: CDS of GenScript-optimized SoD2 (07)
<220> FEATURE:
<221> NAME/KEY: misc_feture
<222> LOCATION: (263)..(268)
<223> OTHER INFORMATION: XbaI restriction site

<400> SEQUENCE: 9
tctagaaaca atgggcttct cccttttctc tcaaatgcct tcattttcc ttgtttctac      60 tcttcttctt tttcttatta tttctcattc ttctcatgct ggtattttct catctaggaa    120
gtgcaaaact ccttcaaaga cttttaaggg aatttgcact agggattcta attgcgatac    180
ttcttgcaga tacgagggat atccagctgg cgattgcaaa ggaattagga ggagatgtat    240
gtgttcaaag ccatgttaat aatctaga                                       268

<210> SEQ ID NO 10
<211> LENGTH: 226
<212> TYPE: DNA
<213> ORGANISM: Artificial Sequence
<220> FEATURE:
<223> OTHER INFORMATION: Chimeric nucleic acid encoding a signal peptide
      and SoD7 codon-optimized with GenScript
<220> FEATURE:
<221> NAME/KEY: misc_feature
```

```
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
<221> NAME/KEY: misc_feature
<222> LOCATION: (101)..(214)
<223> OTHER INFORMATION: CDS of GenScript-optimized SoD7 (08)
<220> FEATURE:
<221> NAME/KEY: misc_feature
<222> LOCATION: (221)..(226)
<223> OTHER INFORMATION: XbaI restriction site

<400> SEQUENCE: 10
tctagaaaca atgggtttct tcttgttttc tcaaatgcct tcattctttc ttgtttcaac      60
tttgcttctt tttcttatta tttctcattc atctcatgct ggaattttct cttcaaggaa     120
gtgcaagact ccatctaaga ctttcaaggg atattgtact agggattcta actgcgatac     180
atcatgcaga tacgagggct atcctgctgg cgattaataa tctaga                    226

<210> SEQ ID NO 11
<211> LENGTH: 268
<212> TYPE: DNA
<213> ORGANISM: Artificial Sequence
<220> FEATURE:
<223> OTHER INFORMATION: Chimeric nucleic acid encoding a signal peptide
      and SoD2 codon-optimized with CODA
<220> FEATURE:
<221> NAME/KEY: misc-feature
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
<221> NAME/KEY: misc_feature
<222> LOCATION: (101)..(256)
<223> OTHER INFORMATION: CDS of CODA-optimized SoD2 (09)
<220> FEATURE:
<221> NAME/KEY: misc_feature
<222> LOCATION: (263)..(268)
<223> OTHER INFORMATION: Sac I, SstI restriction site

<400> SEQUENCE: 11
tctagaaaca atgggtttct ttttgttttc tcatttttcc ttgtgtctac                  60
tcttcttctt tttcttatta tttctcattc ttctcatgct ggtatctttt ctagtagaaa     120
gtgtaagact ccttctaaga cttttaaagg tatttgcact agagattcta attgtgacac     180
ttcttgtaga tatgaaggtt atcctgctgg tgattgtaag ggtattagaa gaagatgtat     240
gtgttctaag ccttgttaat aggagctc                                         268

<210> SEQ ID NO 12
<211> LENGTH: 226
<212> TYPE: DNA
<213> ORGANISM: Artificial Sequence
<220> FEATURE:
<223> OTHER INFORMATION: Chimeric nucleic acid encoding a signal peptide
      and SoD7 codon-optimized with CODA
<220> FEATURE:
<221> NAME/KEY: misc_feature
<222> LOCATION: (1)..(6)
<223> OTHER INFORMATION: XbaI restriction site
<220> FEATURE:
<221> NAME/KEY: sig_peptide
<222> LOCATION: (11)..(100)
<223> OTHER INFORMATION: PR-1b signal peptide
<220> FEATURE:
```

```
<221> NAME/KEY: misc_feature
<222> LOCATION: (101)..(214)
<223> OTHER INFORMATION: CDS of CODA-optimized SoD7 (10)
<220> FEATURE:
<221> NAME/KEY: misc_feature
<222> LOCATION: (221)..(226)
<223> OTHER INFORMATION: SacI, SstI restriction site

<400> SEQUENCE: 12
tctagaaaca atgggattct ttttgttttc tcaaatgcct tctttcttc ttgtgtctac    60 tcttcttctt tttcttatta tttctcattc ttctcatgct ggtattttt catctcgtaa   120 gtgtaagact ccttctaaga cttttaaggg ttattgcact agagattcta attgtgatac   180
atcttgtaga tatgaaggtt atcctgctgg tgattaatag gagctc                  226

<210> SEQ ID NO 13
<211> LENGTH: 1462
<212> TYPE: DNA
<213> ORGANISM: Artificial Sequence
<220> FEATURE:
<223> OTHER INFORMATION: SoD2 expression cassette comprising a chimeric
      nucleic acid encoding a signal peptide and SoD2
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: sig_peptide
<222> LOCATION: (934)..(1023)
<223> OTHER INFORMATION: PR-1b signal peptide
<220> FEATURE:
<221> NAME/KEY: misc_feature
<222> LOCATION: (1024)..(1179)
<223> OTHER INFORMATION: CDS of encodes SoD2 peptide
<220> FEATURE:
<221> NAME/KEY: misc_feature
<222> LOCATION: (1186)..(1191)
<223> OTHER INFORMATION: SacI, SstI restriction site
<220> FEATURE:
<221> NAME/KEY: misc_feature
<222> LOCATION: (1192)..(1257)
<223> OTHER INFORMATION: polylinker
<220> FEATURE:
<221> NAME/KEY: terminator
<222> LOCATION: (1257)..(1462)
<223> OTHER INFORMATION: 35ST

<400> SEQUENCE: 13
atggtggagc acgacactct cgtctactcc aagaatatca agatacagt ctcagaagac     60 caaagggcta ttgagacttt tcaacaaagg gtaatatcgg gaaacctcct cggattccat   120
tgcccagcta tctgtcactt catcaaaagg acagtagaaa aggaaggtgg cacctacaaa   180
tgccatcatt gcgataaagg aaaggctatc gttcaagatg cctctgccga cagtggtccc   240
aaagatggac ccccacccac gaggagcatc gtggaaaaag aagacgttcc aaccacgtct   300
tcaaagcaag tggattgatg tgataacatg gtggagcacg acactctcgt ctactccaag   360
aatatcaaag atacagtctc agaagaccaa aggctattg agacttttca acaaagggta   420
atatcgggaa acctcctcgg attccattgc ccagctatct gtcacttcat caaaaggaca   480
gtagaaaagg aaggtggcac ctacaaatgc catcattgcg ataaaggaaa ggctatcgtt   540
```

```
caagatgcct ctgccgacag tggtcccaaa gatggacccc cacccacgag gagcatcgtg      600
gaaaaagaag acgttccaac cacgtcttca aagcaagtgg attgatgtga tatctccact      660
gacgtaaggg atgacgcaca atcccactat ccttcgcaag accttcctct atataaggaa      720
gttcatttca tttggagagg acacgctgaa atcaccagtc tctctctaca aatctatctc      780
aaataacaaa tctcaacaca acatatacaa aacaaacgaa tctcaagcaa tcaagcattc      840
tacttctatt gcagcaattt aaatcatttc ttttaaagca aaagcaattt tctgaaaatt      900
ttcaccattt acgaacgata gcatctagaa acaatgggct tcttcctttt ctctcaaatg      960
ccttcatttt tccttgtttc tactcttctt ctttttctta ttatttctca ttcttctcat     1020
gctggtattt tctcatctag gaagtgcaaa actccttcaa agacttttaa gggaatttgc     1080
actagggatt ctaattgcga tacttcttgc agatacgagg gatatccagc tggcgattgc     1140
aaaggaatta ggaggagatg tatgtgttca aagccatgtt aataatctag aacgcgtgaa     1200
ttcgaggcct cggatccctc gaggagctcg taccegggg tccgcaaaaa tcaccagtct     1260
ctctctacaa atctatctct ctctattttt tccagaata atgtgtgagt agttcccaga     1320
taagggaatt agggttctta tagggtttcg ctcatgtgtt gagcatataa gaaaccctta     1380
gtatgtattt gtatttgtaa aatacttcta tcaataaaat ttctaattcc taaaaccaaa     1440
atccagtgac ctgcaggcat gc                                              1462

<210> SEQ ID NO 14
<211> LENGTH: 1420
<212> TYPE: DNA
<213> ORGANISM: Artificial Sequence
<220> FEATURE:
<223> OTHER INFORMATION: SoD7 expression cassette comprising a chimeric
      nucleic acid encoding a signal peptide and SoD7
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: sig_peptide
<222> LOCATION: (934)..(1023)
<223> OTHER INFORMATION: PR-1b signal peptide
<220> FEATURE:
<221> NAME/KEY: misc_feature
<222> LOCATION: (1024)..(1143)
<223> OTHER INFORMATION: CDS of Encodes SoD7 peptide
<220> FEATURE:
<221> NAME/KEY: misc_feature
<222> LOCATION: (1144)..(1149)
<223> OTHER INFORMATION: SacI, SstI restriction site
<220> FEATURE:
<221> NAME/KEY: misc_feature
<222> LOCATION: (1150)..(1215)
<223> OTHER INFORMATION: polylinker
<220> FEATURE:
<221> NAME/KEY: terminator
<222> LOCATION: (1216)..(1420)
<223> OTHER INFORMATION: 35ST

<400> SEQUENCE: 14
atggtggagc acgacactct cgtctactcc aagaatatca agatacagt ctcagaagac       60 caaagggcta ttgagacttt tcaacaaagg gtaatatcgg gaaacctcct cggattccat      120
```

```
tgcccagcta tctgtcactt catcaaaagg acagtagaaa aggaaggtgg cacctacaaa      180
tgccatcatt gcgataaagg aaaggctatc gttcaagatg cctctgccga cagtggtccc      240
aaagatggac ccccacccac gaggagcatc gtggaaaaag aagacgttcc aaccacgtct      300
tcaaagcaag tggattgatg tgataacatg gtggagcacg acactctcgt ctactccaag      360
aatatcaaag atacagtctc agaagaccaa agggctattg agacttttca acaaagggta      420
atatcgggaa acctcctcgg attccattgc ccagctatct gtcacttcat caaaaggaca      480
gtagaaaagg aaggtggcac ctacaaatgc catcattgcg ataaaggaaa ggctatcgtt      540
caagatgcct ctgccgacag tggtcccaaa gatggacccc cacccacgag gagcatcgtg      600 gaaaagaag acgttccaac cacgtcttca aagcaagtgg attgatgtga tatctccact      660
gacgtaaggg atgacgcaca atcccactat ccttcgcaag accttcctct atataaggaa      720
gttcatttca tttggagagg acacgctgaa atcaccagtc tctctctaca aatctatctc      780
aaataacaaa tctcaacaca acatatacaa aacaaacgaa tctcaagcaa tcaagcattc      840
tacttctatt gcagcaattt aaatcatttc ttttaaagca aaagcaattt tctgaaaatt      900
ttcaccattt acgaacgata gcatctagaa acaatgggtt tcttcttgtt ttctcaaatg      960
ccttcattct ttcttgtttc aactttgctt cttttttctta ttatttctca ttcatctcat     1020
gctggaattt tctcttcaag gaagtgcaag actccatcta agactttcaa gggatattgt     1080
actagggatt ctaactgcga tacatcatgc agatacgagg ctatcctgc tggcgattaa      1140 taatctagaa cgcgtgaatt cgaggcctcg gatccctcga ggagctcggt acccggggtc     1200
cgcaaaaatc accagtctct ctctacaaat ctatctctct ctattttct ccagaataat      1260 gtgtgagtag ttcccagata agggaattag ggttcttata gggtttcgct catgtgttga     1320
gcatataaga aacccttagt atgtatttgt atttgtaaaa tacttctatc aataaaattt     1380
ctaattccta aaaccaaaat ccagtgacct gcaggcatgc                            1420
```

<210> SEQ ID NO 15
<211> LENGTH: 1424
<212> TYPE: DNA
<213> ORGANISM: Artificial Sequence
<220> FEATURE:
<223> OTHER INFORMATION: Chimeric nucleic acid encoding a signal peptide and SoD2
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: sig_peptide
<222> LOCATION: (934)..(1023)
<223> OTHER INFORMATION: PR-1b signal peptide
<220> FEATURE:
<221> NAME/KEY: misc_feature
<222> LOCATION: (1024)..(1179)
<223> OTHER INFORMATION: CDS of Encodes SoD2 peptide
<220> FEATURE:
<221> NAME/KEY: misc_feature
<222> LOCATION: (1186)..(1191)
<223> OTHER INFORMATION: SacI, SstI restriction site
<220> FEATURE:
<221> NAME/KEY: misc_feature
<222> LOCATION: (1192)..(1219)

<223> OTHER INFORMATION: polylinker
<220> FEATURE:
<221> NAME/KEY: terminator
<222> LOCATION: (1220)..(1424)
<223> OTHER INFORMATION: 35ST

<400> SEQUENCE: 15

```
atggtggagc acgacactct cgtctactcc aagaatatca agatacagt ctcagaagac      60
caaagggcta ttgagacttt tcaacaaagg gtaatatcgg gaaacctcct cggattccat    120
tgcccagcta tctgtcactt catcaaaagg acagtagaaa aggaaggtgg cacctacaaa    180
tgccatcatt gcgataaagg aaaggctatc gttcaagatg cctctgccga cagtggtccc    240
aaagatggac ccccacccac gaggagcatc gtggaaaaag aagacgttcc aaccacgtct    300
tcaaagcaag tggattgatg tgataacatg gtggagcacg acactctcgt ctactccaag    360
aatatcaaag atacagtctc agaagaccaa agggctattg agacttttca acaaagggta    420
atatcgggaa acctcctcgg attccattgc ccagctatct gtcacttcat caaaaggaca    480
gtagaaaagg aaggtggcac ctacaaatgc catcattgcg ataaaggaaa ggctatcgtt    540
caagatgcct ctgccgacag tggtcccaaa gatggacccc acccacgag gagcatcgtg      600
gaaaagaag acgttccaac cacgtcttca agcaagtgg attgatgtga tatctccact       660
gacgtaaggg atgacgcaca atcccactat ccttcgcaag accttcctct atataaggaa    720
gttcatttca tttggagagg cacgctgaa atcaccagtc tctctctaca aatctatctc      780
aaataacaaa tctcaacaca acatatacaa aacaaacgaa tctcaagcaa tcaagcattc    840
tacttctatt gcagcaattt aaatcatttc ttttaaagca aaagcaattt ctgaaaatt     900
ttcaccattt acgaacgata gcatctagaa acaatgggtt ctttttgtt ttctcaaatg     960
ccttcatttt tccttgtgtc tactcttctt cttttcta ttatttctca ttcttctcat     1020
gctggtatct tttctagtag aaagtgtaag actccttcta agacttttaa aggtatttgc    1080
actagagatt ctaattgtga cacttcttgt agatatgaag gttatcctgc tggtgattgt    1140
aagggtatta gaagaagatg tatgtgttct aagccttgtt aataggagct cggtacccgg    1200
ggtccgcaaa atcaccagt ctctctctac aaatctatct ctctctattt ttctccagaa    1260
taatgtgtga gtagttccca gataagggaa ttagggttct tatagggttt cgctcatgtg    1320
ttgagcatat aagaaaccct tagtatgtat ttgtatttgt aaaatacttc tatcaataaa    1380
atttctaatt cctaaaacca aaatccagtg acctgcaggc atgc                     1424
```

<210> SEQ ID NO 16
<211> LENGTH: 1388
<212> TYPE: DNA
<213> ORGANISM: Artificial Sequence
<220> FEATURE:
<223> OTHER INFORMATION: Chimeric nucleic acid encoding a signal peptide and SoD7
<220> FEATURE:
<221> NAME/KEY: promoter
<222> LOCATION: (1)..(780)
<223> OTHER INFORMATION: 35SP
<220> FEATURE:
<221> NAME/KEY: 5'UTR
<222> LOCATION: (781)..(923)
<223> OTHER INFORMATION: TEV 5' UTR
<220> FEATURE:
<221> NAME/KEY: misc_feature
<222> LOCATION: (781)..(923)
<223> OTHER INFORMATION: XbaI restriction site
<220> FEATURE:
<221> NAME/KEY: sig_peptide
<222> LOCATION: (934)..(1023)

<223> OTHER INFORMATION: PR-1b signal peptide
<220> FEATURE:
<221> NAME/KEY: misc_feature
<222> LOCATION: (1024)..(1137)
<223> OTHER INFORMATION: CDS of Encodes SoD7 peptide
<220> FEATURE:
<221> NAME/KEY: misc_feature
<222> LOCATION: (1144)..(1149)
<223> OTHER INFORMATION: SacI, SstI restriction site
<220> FEATURE:
<221> NAME/KEY: misc_feature
<222> LOCATION: (1150)..(1177)
<223> OTHER INFORMATION: polylinker
<220> FEATURE:
<221> NAME/KEY: terminator
<222> LOCATION: (1178)..(1382)
<223> OTHER INFORMATION: 35ST

<400> SEQUENCE: 16

```
atggtggagc acgacactct cgtctactcc aagaatatca agatacagt ctcagaagac      60
caaagggcta ttgagacttt tcaacaaagg gtaatatcgg gaaacctcct cggattccat    120
tgcccagcta tctgtcactt catcaaaagg acagtagaaa aggaaggtgg cacctacaaa    180
tgccatcatt gcgataaagg aaaggctatc gttcaagatg cctctgccga cagtggtccc    240
aaagatggac ccccacccac gaggagcatc gtggaaaaag aagacgttcc aaccacgtct    300
tcaaagcaag tggattgatg tgataacatg gtggagcacg acactctcgt ctactccaag    360
aatatcaaag atacagtctc agaagaccaa agggctattg agacttttca acaagggta    420
atatcgggaa acctcctcgg attccattgc ccagctatct gtcacttcat caaaaggaca    480
gtagaaaagg aaggtggcac ctacaaatgc catcattgcg ataaaggaaa ggctatcgtt    540
caagatgcct ctgccgacag tggtcccaaa gatggacccc cacccacgag gagcatcgtg    600
gaaaaagaag acgttccaac cacgtcttca agcaagtgg attgatgtga tatctccact    660
gacgtaaggg atgacgcaca atcccactat ccttcgcaag accttcctct atataaggaa    720
gttcatttca tttggagagg acacgctgaa atcaccagtc tctctctaca aatctatctc    780
aaataacaaa tctcaacaca acatatacaa aacaaacgaa tctcaagcaa tcaagcattc    840
tacttctatt gcagcaattt aaatcatttc ttttaaagca aaagcaattt tctgaaaatt    900
ttcaccattt acgaacgata gcatctagaa acaatgggat tcttttttgtt ttctcaaatg    960
ccttctttct tcttgtgtc tactcttctt ctttttctta ttatttctca ttcttctcat    1020
gctggtattt tttcatctcg taagtgtaag actccttcta agactttaa gggttattgc    1080
actagagatt ctaattgtga tacatcttgt agatatgaag ttatcctgc tggtgattaa    1140
taggagctcg gtacccgggg tccgcaaaaa tcaccagtct ctctctacaa atctatctct    1200
ctctatttt tccagaata atgtgtgagt agttcccaga taagggaatt agggttctta    1260
tagggtttcg ctcatgtgtt gagcatataa gaaaccctta gtatgtattt gtatttgtaa    1320
aatacttcta tcaataaaat ttctaattcc taaaaccaaa atccagtgac ctgcaggcat    1380
gcgagaga                                                             1388
```

<210> SEQ ID NO 17
<211> LENGTH: 780
<212> TYPE: DNA
<213> ORGANISM: Cauliflower mosaic virus
<220> FEATURE:
<221> NAME/KEY: promoter
<222> LOCATION: (1)..(780)
<223> OTHER INFORMATION: CaMV 35S promoter

<400> SEQUENCE: 17

-continued

```
atggtggagc acgacactct cgtctactcc aagaatatca agatacagt ctcagaagac      60 caaagggcta ttgagacttt tcaacaaagg gtaatatcgg gaaacctcct cggattccat    120
tgcccagcta tctgtcactt catcaaaagg acagtagaaa aggaaggtgg cacctacaaa    180
tgccatcatt gcgataaagg aaaggctatc gttcaagatg cctctgccga cagtggtccc    240
aaagatggac ccccacccac gaggagcatc gtggaaaaag aagacgttcc aaccacgtct    300
tcaaagcaag tggattgatg tgataacatg gtggagcacg acactctcgt ctactccaag    360
aatatcaaag atacagtctc agaagaccaa agggctattg agacttttca caaagggta     420 atatcgggaa acctcctcgg attccattgc ccagctatct gtcacttcat caaaaggaca    480
gtagaaaagg aaggtggcac ctacaaatgc catcattgcg ataaaggaaa ggctatcgtt    540
caagatgcct ctgccgacag tggtcccaaa gatggacccc cacccacgag gagcatcgtg    600 gaaaagaag acgttccaac cacgtcttca aagcaagtgg attgatgtga tatctccact    660
gacgtaaggg atgacgcaca atcccactat ccttcgcaag accttcctct atataaggaa    720
gttcatttca tttggagagg cacgctgaaa atcaccagtc tctctctaca aatctatctc    780
```

<210> SEQ ID NO 18
<211> LENGTH: 143
<212> TYPE: DNA
<213> ORGANISM: Tobacco etch virus
<220> FEATURE:
<221> NAME/KEY: enhancer
<222> LOCATION: (1)..(143)
<223> OTHER INFORMATION: TEV 5'UTR translational enhancer

<400> SEQUENCE: 18

```
aaataacaaa tctcaacaca acatatacaa aacaaacgaa tctcaagcaa tcaagcattc     60
tacttctatt gcagcaattt aaatcattc ttttaaagca aaagcaattt tctgaaaatt    120
ttcaccattt acgaacgata gca                                            143
```

<210> SEQ ID NO 19
<211> LENGTH: 205
<212> TYPE: DNA
<213> ORGANISM: Cauliflower mosaic virus
<220> FEATURE:
<221> NAME/KEY: terminator
<222> LOCATION: (1)..(205)
<223> OTHER INFORMATION: CaMV 35S terminator

<400> SEQUENCE: 19

```
tctctctcta caaatctatc tctctctatt tttctccaga ataatgtgtg agtagttccc     60
agataaggga attagggttc ttatagggtt tcgctcatgt gttgagcata taagaaaccc    120
ttagtatgta tttgtatttg taaaatactt ctatcaataa aatttctaat tcctaaaacc    180
aaaatccagt gacctgcagg catgc                                          205
```

<210> SEQ ID NO 20
<211> LENGTH: 31
<212> TYPE: DNA
<213> ORGANISM: Artificial Sequence
<220> FEATURE:
<223> OTHER INFORMATION: Zn5 Primer

<400> SEQUENCE: 20

```
ccaatgcatt gatcttcaaa tgggaatgaa t                                    31
```

<210> SEQ ID NO 21

-continued

<210> SEQ ID NO 21
<211> LENGTH: 28
<212> TYPE: DNA
<213> ORGANISM: Artificial Sequence
<220> FEATURE:
<223> OTHER INFORMATION: Zn6 Primer

<400> SEQUENCE: 21
aactgcagtt ctaagaccag tcaaacta                                      28

<210> SEQ ID NO 22
<211> LENGTH: 40
<212> TYPE: DNA
<213> ORGANISM: Artificial Sequence
<220> FEATURE:
<223> OTHER INFORMATION: Fcp Primer

<400> SEQUENCE: 22
ggcctctaga gttatggacg acgagacata gtaattgaag                         40

<210> SEQ ID NO 23
<211> LENGTH: 34
<212> TYPE: DNA
<213> ORGANISM: Artificial Sequence
<220> FEATURE:
<223> OTHER INFORMATION: Rcp Primer

<400> SEQUENCE: 23
gcgcgagctc gatgaaactc caccatcccg atag                               34

<210> SEQ ID NO 24
<211> LENGTH: 20
<212> TYPE: DNA
<213> ORGANISM: Artificial Sequence
<220> FEATURE:
<223> OTHER INFORMATION: GUSF Primer

<400> SEQUENCE: 24
gtagaaaccc caacccgtga                                               20

<210> SEQ ID NO 25
<211> LENGTH: 21
<212> TYPE: DNA
<213> ORGANISM: Artificial Sequence
<220> FEATURE:
<223> OTHER INFORMATION: GUSR Primer

<400> SEQUENCE: 25
gcggattcac cacttgcaaa g                                             21

<210> SEQ ID NO 26
<211> LENGTH: 83
<212> TYPE: PRT
<213> ORGANISM: Artificial Sequence
<220> FEATURE:
<223> OTHER INFORMATION: Variant of SoD2 comprising two additional
      N-terminal amino acids and a Gly33 deletion relative to spinach
      SoD2
<220> FEATURE:
<221> NAME/KEY: signal
<222> LOCATION: (1)..(32)
<223> OTHER INFORMATION: Modified PR-1b signal peptide
<220> FEATURE:
<221> NAME/KEY: mat_peptide
<222> LOCATION: (33)..(83)
<223> OTHER INFORMATION: Putative mature SoD2 peptide with a Gly33
      deletion relative to spinach SoD2

<400> SEQUENCE: 26

```
Met Gly Phe Phe Leu Phe Ser Gln Met Pro Ser Phe Leu Val Ser
    -30                 -25                 -20

Thr Leu Leu Leu Phe Leu Ile Ile Ser His Ser Ser His Ala Leu Glu
    -15                 -10                  -5                  -1

Gly Ile Phe Ser Ser Arg Lys Cys Lys Thr Pro Ser Lys Thr Phe Lys
1                5                  10                 15

Gly Ile Cys Thr Arg Asp Ser Asn Cys Asp Thr Ser Cys Arg Tyr Glu
            20                  25                  30

Tyr Pro Ala Gly Asp Cys Lys Gly Ile Arg Arg Arg Cys Met Cys Ser
        35                  40                  45

Lys Pro Cys
    50

<210> SEQ ID NO 27
<211> LENGTH: 265
<212> TYPE: DNA
<213> ORGANISM: Artificial Sequence
<220> FEATURE:
<223> OTHER INFORMATION: Variant of SoD2 comprising two additional
      N-terminal amino acids and a Gly33 deletion relative to spinach
      SoD2
<220> FEATURE:
<221> NAME/KEY: sig_peptide
<222> LOCATION: (8)..(103)
<223> OTHER INFORMATION: PR-1b signal peptide fragment
<220> FEATURE:
<221> NAME/KEY: misc_feature
<222> LOCATION: (104)..(259)
<223> OTHER INFORMATION: CDS of Putative mature SoD2 peptide with a
      Gly33 deletion relative to spinach SoD2

<400> SEQUENCE: 27
ttaattaatg ggattctttc tcttttcaca aatgccctca ttctttcttg tgtcgacact      60
tctcttattc ctaataatat ctcactcttc tcatgcgctc gagggaatat tcagctcccg    120
caagtgtaag acgccttcaa agactttcaa agggatatgt acgagagact caaactgtga    180
cacctcatgt cgttacgaat atccggcagg agactgtaaa ggaatacgtc gcagatgtat    240
gtgtagcaag ccttgttaga ggcct                                         265

<210> SEQ ID NO 28
<211> LENGTH: 38
<212> TYPE: PRT
<213> ORGANISM: Artificial Sequence
<220> FEATURE:
<223> OTHER INFORMATION: Core defensin based, in part, on Sod2 and Sod7
<220> FEATURE:
<221> NAME/KEY: VARIANT
<222> LOCATION: (18)..(18)
<223> OTHER INFORMATION: Any amino acid

<400> SEQUENCE: 28

Gly Ile Phe Ser Ser Arg Lys Cys Lys Thr Pro Ser Lys Thr Phe Lys
1                5                  10                 15

Gly Xaa Cys Thr Arg Asp Ser Asn Cys Asp Thr Ser Cys Arg Tyr Glu
            20                  25                  30

Gly Tyr Pro Ala Gly Asp
        35

<210> SEQ ID NO 29
<211> LENGTH: 120
<212> TYPE: DNA
<213> ORGANISM: Artificial Sequence
<220> FEATURE:
<223> OTHER INFORMATION: Core defensin based, in part, on Sod2 and Sod7
```

```
<220> FEATURE:
<221> NAME/KEY: variation
<222> LOCATION: (52)..(52)
<223> OTHER INFORMATION: t, any other base, or absent (e.g., if 53 and
      54 are also absent)
<220> FEATURE:
<221> NAME/KEY: misc_feature
<222> LOCATION: (52)..(54)
<223> OTHER INFORMATION: n is a, c, g, or t
<220> FEATURE:
<221> NAME/KEY: variation
<222> LOCATION: (53)..(53)
<223> OTHER INFORMATION: a, any other base, or absent (e.g., if 52 and
      54 are also absent)
<220> FEATURE:
<221> NAME/KEY: variation
<222> LOCATION: (54)..(54)
<223> OTHER INFORMATION: t, any other base, or absent (e.g., if 52 and
      53 are also absent)

<400> SEQUENCE: 29
ggaattttct cttcaaggaa gtgcaagact ccatctaaga ctttcaaggg annntgtact    60
agggattcta actgcgatac atcatgcaga tacgagggct atcctgctgg cgattaataa   120

<210> SEQ ID NO 30
<211> LENGTH: 174
<212> TYPE: DNA
<213> ORGANISM: Artificial Sequence
<220> FEATURE:
<223> OTHER INFORMATION: SoD2 codon-optimized with DNA 2.0

<400> SEQUENCE: 30
tctagaatgg gaatcttcag ttcgagaaag tgtaaaaccc cctcaaaaac attcaaaggt    60
atttgcacga gagattctaa ttgcgatact agctgccgtt atgagggtta ccctgctggc   120
gactgtaagg ggataaggag gagatgtatg tgctccaagc catgttaagg tacc         174

<210> SEQ ID NO 31
<211> LENGTH: 132
<212> TYPE: DNA
<213> ORGANISM: Artificial Sequence
<220> FEATURE:
<223> OTHER INFORMATION: SoD7 codon-optimized with DNA 2.0

<400> SEQUENCE: 31
tctagaatgg gtatcttctc aagcagaaag tgcaaaacac cttctaaaac ctttaaggga    60
tattgtacta gggactccaa ttgtgatacg agttgccgtt acgagggcta tccagctggg   120
gattaaggta cc                                                       132

<210> SEQ ID NO 32
<211> LENGTH: 60
<212> TYPE: PRT
<213> ORGANISM: Spinacia oleracea
<220> FEATURE:
<221> NAME/KEY: mat_peptide
<222> LOCATION: (1)..(60)
<223> OTHER INFORMATION: Def1 peptide

<400> SEQUENCE: 32

Met Gly Pro Arg Lys Ala Glu Ala Gly Ile Phe Ser Ser Arg Lys Cys
1               5                   10                  15

Lys Thr Pro Ser Lys Thr Phe Lys Gly Ile Cys Thr Arg Asp Ser Asn
            20                  25                  30

Cys Asp Thr Ser Cys Arg Tyr Glu Gly Tyr Pro Ala Gly Asp Cys Lys
        35                  40                  45
```

```
Gly Ile Arg Arg Arg Cys Leu Cys Cys Thr His Thr
    50                  55                  60
```

<210> SEQ ID NO 33
<211> LENGTH: 83
<212> TYPE: PRT
<213> ORGANISM: Spinacia oleracea
<220> FEATURE:
<221> NAME/KEY: mat_peptide
<222> LOCATION: (1)..(83)
<223> OTHER INFORMATION: Def2 peptide

<400> SEQUENCE: 33

```
Met Lys Met Ser Met Arg Ser Ile Ala Val Val Phe Leu Val Cys Leu
1               5                   10                  15

Leu Val Leu Ser Thr Glu Glu Met Gly Pro Arg Lys Ala Asp Ala Gly
            20                  25                  30

Phe Phe Ser Ser Lys Lys Cys Lys Thr Pro Ser Lys Thr Phe Arg Gly
        35                  40                  45

Pro Cys Val Arg Asn Ala Asn Cys Asp Thr Ser Cys Arg Tyr Glu Gly
    50                  55                  60

Tyr Pro Ala Gly Asp Cys Lys Gly Ile Arg Arg Cys Ile Cys
65                  70                  75                  80

Thr His Ala
```

<210> SEQ ID NO 34
<211> LENGTH: 74
<212> TYPE: PRT
<213> ORGANISM: Spinacia oleracea
<220> FEATURE:
<221> NAME/KEY: mat_peptide
<222> LOCATION: (1)..(74)
<223> OTHER INFORMATION: Def3 peptide

<400> SEQUENCE: 34

```
Met Lys His Phe Gly Ala Ile Phe Leu Val Leu Leu Val Leu Ala
1               5                   10                  15

Thr Glu His Gly Ala Arg Val Ala Glu Ala Arg Thr Cys Glu Thr Pro
            20                  25                  30

Ser Gln Lys Phe Lys Gly Ile Cys Ile Ser Asp Ser Asn Cys Glu Ser
        35                  40                  45

Ile Cys Asn Thr Glu Gly Phe Pro Asn Gly Glu Cys Ser Gly Leu Arg
    50                  55                  60

Arg Arg Cys Ile Cys Asn Thr Pro Cys Thr
65                  70
```

<210> SEQ ID NO 35
<211> LENGTH: 56
<212> TYPE: PRT
<213> ORGANISM: Spinacia oleracea
<220> FEATURE:
<221> NAME/KEY: mat_peptide
<222> LOCATION: (1)..(56)
<223> OTHER INFORMATION: Def4 peptide

<400> SEQUENCE: 35

```
Val Ser Thr Lys Val Ala Glu Ala Arg Ile Cys Ala Ser Pro Ser Pro
1               5                   10                  15

Thr Phe Lys Gly Ile Cys Phe Ser Ser Arg Asn Cys Glu Thr Asn Cys
            20                  25                  30

Asn Ser Val Lys Phe Ser Gly Gly Ser Cys Gln Gly Phe Arg Arg Arg
        35                  40                  45
```

```
Cys Met Cys Thr Lys Pro Cys Ala
    50                  55
```

<210> SEQ ID NO 36
<211> LENGTH: 74
<212> TYPE: PRT
<213> ORGANISM: Spinacia oleracea
<220> FEATURE:
<221> NAME/KEY: mat_peptide
<222> LOCATION: (1)..(74)
<223> OTHER INFORMATION: Def5 peptide

<400> SEQUENCE: 36

```
Met Arg Pro Phe Ala Ala Leu Phe Leu Val Leu Phe Leu Val Leu Ala
1               5                   10                  15

Thr Glu Ile Gly Pro Arg Val Val Glu Ala Arg Met Cys Ser Ser Pro
            20                  25                  30

Ser His Arg Phe Lys Gly Ile Cys Thr Cys Ser Arg Asn Cys Glu Asn
        35                  40                  45

Thr Cys Asn Ser Glu Arg Phe Ser Gly Gly Glu Cys Lys Gly Phe Arg
    50                  55                  60

Arg Arg Cys Met Cys Thr Gly Pro Cys Val
65                  70
```

<210> SEQ ID NO 37
<211> LENGTH: 90
<212> TYPE: PRT
<213> ORGANISM: Spinacia oleracea
<220> FEATURE:
<221> NAME/KEY: mat_peptide
<222> LOCATION: (1)..(90)
<223> OTHER INFORMATION: Def6 peptide

<400> SEQUENCE: 37

```
Met Glu Arg Ser Ser Arg Val Phe Ser Val Val Leu Leu Met Leu Val
1               5                   10                  15

Leu Val Leu Ser Thr Asp Met Tyr Thr Asp Pro Val Ala Val Leu Ser
            20                  25                  30

Tyr Glu Ile Gly Thr Lys Val Ala Glu Ala Arg Ile Cys Glu Ser Ala
        35                  40                  45

Ser Tyr Arg Phe Lys Gly Ile Cys Val Ser Arg Ser Asn Cys Ala Asn
    50                  55                  60

Val Cys Lys Asn Glu Gly Phe Pro Gly Gly Arg Cys Arg Gly Phe Arg
65                  70                  75                  80

Arg Arg Cys Leu Cys Tyr Lys His Cys Gly
                85                  90
```

<210> SEQ ID NO 38
<211> LENGTH: 74
<212> TYPE: PRT
<213> ORGANISM: Spinacia oleracea
<220> FEATURE:
<221> NAME/KEY: mat_peptide
<222> LOCATION: (1)..(74)
<223> OTHER INFORMATION: Def6 peptide

<400> SEQUENCE: 38

```
Met Lys Pro Phe Val Ala Phe Val Leu Ala Phe Met Leu Val Leu Ala
1               5                   10                  15

Ile Glu Met Gly Pro Arg Val Ala Glu Ala Arg Met Cys Thr Asn Pro
            20                  25                  30
```

```
Ser Arg Thr Phe Arg Gly Pro Cys Val Ser Asp Arg Asn Cys Glu Ser
         35                  40                  45

Ser Cys Met Gly Glu Gly Phe Pro Gly Gly Ser Cys His Gly Phe Arg
 50                  55                  60

Arg Lys Cys Val Cys Ser Lys Pro Cys Ala
 65                  70
```

```
<210> SEQ ID NO 39
<211> LENGTH: 183
<212> TYPE: DNA
<213> ORGANISM: Spinacea oleracea
<220> FEATURE:
<221> NAME/KEY: misc_feature
<222> LOCATION: (1)..(143)
<223> OTHER INFORMATION: Def1 nucleotide

<400> SEQUENCE: 39
atgggtccaa gaaaggcaga agctggaatt tttagctcga ggaaatgcaa aactccaagt      60
aaaacgttca agggaatatg tactagggac tccaattgtg acacttcttg taggtatgag    120
ggatatccag ctggagattg caagggtatt cgtagaagat gcttatgttg tacacatact    180
taa                                                                   183

<210> SEQ ID NO 40
<211> LENGTH: 252
<212> TYPE: DNA
<213> ORGANISM: Spinacea oleracea
<220> FEATURE:
<221> NAME/KEY: misc_feature
<222> LOCATION: (1)..(252)
<223> OTHER INFORMATION: Def2 nucleotide

<400> SEQUENCE: 40
atgaagatgt caatgaggtc gattgctgtg gttttccttg tgtgcctact tgtcttgtca      60
acagaagaaa tgggtccaag aaaggcagac gctggatttt tcagctcgaa gaaatgcaaa    120
acaccaagta aaacattcag gggaccttgt gtaaggaacg ccaactgtga cacttcttgt    180
aggtatgagg gatatccagc tggagattgc aagggtattc gtagaagatg tatttgttgt    240
acacatgctt aa                                                         252

<210> SEQ ID NO 41
<211> LENGTH: 225
<212> TYPE: DNA
<213> ORGANISM: Spinacia oleracea
<220> FEATURE:
<221> NAME/KEY: misc_feature
<222> LOCATION: (1)..(225)
<223> OTHER INFORMATION: Def3 nucleotide

<400> SEQUENCE: 41
atgaagcact tgggggctat atttcttgtg ttgttgcttg ttctggccac agaacatgga      60
gcaagagtag cagaagcaag aacatgtgaa actccaagtc aaaagttcaa aggaatatgt    120
attagtgact ccaattgtga atcaatttgc aataccgaag gatttcctaa tggagaatgt    180
agtggccttc gcagaagatg catttgcaac acaccatgca cttaa                    225

<210> SEQ ID NO 42
<211> LENGTH: 171
<212> TYPE: DNA
<213> ORGANISM: Spinacia oleracea
<220> FEATURE:
<221> NAME/KEY: misc_feature
<222> LOCATION: (1)..(171)
```

<223> OTHER INFORMATION: Def4 nucleotide

<400> SEQUENCE: 42
gtaagtacaa aagtagcaga agcaaggata tgtgctagtc caagtcccac gttcaaagga    60
atatgtttta gcagcaggaa ttgtgaaact aattgcaatt ctgtgaaatt ttctggagga   120
agttgtcaag gttttcgtag aagatgtatg tgcaccaagc cttgcgctta a            171

<210> SEQ ID NO 43
<211> LENGTH: 225
<212> TYPE: DNA
<213> ORGANISM: Spinacea oleracea
<220> FEATURE:
<221> NAME/KEY: misc_feature
<222> LOCATION: (1)..(225)
<223> OTHER INFORMATION: Def5 nucleotide

<400> SEQUENCE: 43
atgaggcctt tgctgctct tttccttgtg ctcttccttg ttttggccac agagataggg    60
ccaagagtag tagaagcaag aatgtgttca tcaccaagtc ataggttcaa gggaatttgt   120
actagcagca ggaattgtga gaacacttgc aacagcgaac gattttcagg tggtgaatgt   180
aaaggctttc gcagaagatg tatgtgcacg ggaccctgcg tttaa                   225

<210> SEQ ID NO 44
<211> LENGTH: 273
<212> TYPE: DNA
<213> ORGANISM: Spinacea oleracea
<220> FEATURE:
<221> NAME/KEY: misc_feature
<222> LOCATION: (1)..(273)
<223> OTHER INFORMATION: Def6 nucleotide

<400> SEQUENCE: 44
atggagcgtt cttcacgtgt gttttcagtt gttcttctca tgcttgttct tgtgttgtcc    60
acagatatgt acacagaccc agtggcggtt cttagttatg agattgggac aaaggtggcg   120
gaagcaagga tatgcgaatc tgcaagttac aggttcaagg gaatatgtgt gagcaggagc   180
aactgtgcta atgtttgcaa aaatgagggt ttccccggtg gccgttgccg cggtttccgt   240
cgtcgttgcc tctgttacaa acattgcggt taa                                273

<210> SEQ ID NO 45
<211> LENGTH: 225
<212> TYPE: DNA
<213> ORGANISM: Spinacea oleracea
<220> FEATURE:
<221> NAME/KEY: misc_feature
<222> LOCATION: (1)..(225)
<223> OTHER INFORMATION: Def7 nucleotide

<400> SEQUENCE: 45
atgaagccct tgtagctttt tgttcttgct ttcatgcttg tcttggccat agagatgggt    60
ccaagagtag cagaagcaag aatgtgcaca aatccgagta gaacattcag gggaccatgc   120
gttagtgacc ggaactgcga atcgtcgtgc atgggagagg gatttcccgg tggaagttgt   180
catggctttc gtagaaaatg cgtctgcagc aagccttgtg cttag                   225

<210> SEQ ID NO 46
<211> LENGTH: 186
<212> TYPE: DNA
<213> ORGANISM: Artificial Sequence
<220> FEATURE:
<223> OTHER INFORMATION: Def1 codon-optimized with Genscript

<400> SEQUENCE: 46

```
atggggccaa gaaaagccga agccgggata ttcagctcaa gaaagtgcaa gacaccctcc      60
aagacattca aaggcatctg taccagggat tctaattgcg acacctcatg tagatatgag     120
ggttaccctg ctggagattg caagggtatt aggagaaggt gtctttgctg tactcataca     180
taatga                                                                186
```

<210> SEQ ID NO 47
<211> LENGTH: 198
<212> TYPE: DNA
<213> ORGANISM: Artificial Sequence
<220> FEATURE:
<223> OTHER INFORMATION: Def2 codon-optimized with Genscript

<400> SEQUENCE: 47

```
atgacagagg agatgggtcc aaggaaagcc gacgctgggt tcttcagttc taaaaagtgc      60
aaaacaccaa gcaaaacatt cagaggcccct tgcgttagaa atgctaactg cgatacttct    120
tgtagatatg agggttaccc agcaggagac tgcaagggta ttaggagaag gtgtatctgc     180
tgtacacatg cttaatga                                                   198
```

<210> SEQ ID NO 48
<211> LENGTH: 228
<212> TYPE: DNA
<213> ORGANISM: Artificial Sequence
<220> FEATURE:
<223> OTHER INFORMATION: Def3 codon-optimized with Genscript

<400> SEQUENCE: 48

```
atgaaacact tcggggctat cttttttggtg ctcctgctcg tgctcgctac tgaacatggt     60
gccagagttg ctgaggctag aacctgtgaa acccctctc aaaagtttaa aggtatctgc      120
atctctgatt caaactgcga gagcatatgt aacacagaag gtttccctaa tggtgaatgc    180
agtggcctta ggagaaggtg catctgtaac actccatgta cataatga                  228
```

<210> SEQ ID NO 49
<211> LENGTH: 228
<212> TYPE: DNA
<213> ORGANISM: Artificial Sequence
<220> FEATURE:
<223> OTHER INFORMATION: Def5 codon-optimized with Genscript

<400> SEQUENCE: 49

```
atgagaccct tcgccgcttt gttttttggtt ttgttcttgg tgctcgctac agagattgga     60
cccagagtgg tggaggccag gatgtgttct tcacctagcc ataggtttaa gggtatttgc    120
actagcagta ggaattgcga gaacacatgt aattccgaaa gatttctgg tggagagtgc     180
aaaggcttca ggagaaggtg catgtgtacc gggccatgtg tttaatga                  228
```

<210> SEQ ID NO 50
<211> LENGTH: 276
<212> TYPE: DNA
<213> ORGANISM: Artificial Sequence
<220> FEATURE:
<223> OTHER INFORMATION: Def6 codon-optimized with Genscript

<400> SEQUENCE: 50

```
atggagagat cgtcaagagt ttttagcgtt gtgctgctta tgctggtgct ggttctgtct      60
actgatatgt ataccgaccc tgtggctgtt cttttcttatg agattggtac taaggtggct   120
```

```
gaggcaagaa tctgcgaatc tgcctcatac aggtttaagg gcatttgtgt tagcagaagt    180
aattgcgcaa acgtgtgcaa gaatgagggc tttcctggtg aagatgcag ggggttcagg     240 agaaggtgct tgtgttataa gcattgtggt taatga                              276
```

<210> SEQ ID NO 51
<211> LENGTH: 228
<212> TYPE: DNA
<213> ORGANISM: Artificial Sequence
<220> FEATURE:
<223> OTHER INFORMATION: Def7 codon-optimized with Genscript

<400> SEQUENCE: 51

```
atgaaacctt tgtggctttt tgtgctggct tttatgctcg ttctggctat tgaaatgggt    60
ccaagagtgg ctgaggcaag gatgtgtact aatccttcta ggacttttag ggtccatgc     120 gttagtgata ggaactgcga gtcttcatgt atgggcgaag ggtttcccgg tggatcttgc    180
catggcttca ggagaaagtg cgtgtgttct aaaccttgtg cttaatga                228
```

<210> SEQ ID NO 52
<211> LENGTH: 186
<212> TYPE: DNA
<213> ORGANISM: Artificial Sequence
<220> FEATURE:
<223> OTHER INFORMATION: Def1 codon-optimized with VGD

<400> SEQUENCE: 52

```
atgggtccta ggaaggcaga ggctggaata tttagctcga ggaagtgcaa accccaagt     60 aaaacgttta aggaatttg tactagagac tccaattgtg cacttcgtg taggtatgag      120 ggatacccag ctggagattg caagggtatc aggagaaggt gcttatgctg tacacataca    180
taatag                                                               186
```

<210> SEQ ID NO 53
<211> LENGTH: 198
<212> TYPE: DNA
<213> ORGANISM: Artificial Sequence
<220> FEATURE:
<223> OTHER INFORMATION: Def2 codon-optimized with VGD

<400> SEQUENCE: 53

```
atgacagaag agatgggccc gagaaaagca gacgctggat ttttctcatc caagaaatgc    60
aagacaccct caaaaacatt caggggaccct tgtgtaagga acgctaactg tgacacttct    120
tgtaggtatg agggctatcc agctggagat tgcaagggta taggagaaag atgtatttgt    180
tgtacccatg cttaatag                                                  198
```

<210> SEQ ID NO 54
<211> LENGTH: 228
<212> TYPE: DNA
<213> ORGANISM: Artificial Sequence
<220> FEATURE:
<223> OTHER INFORMATION: Def3 codon-optimized with VGD

<400> SEQUENCE: 54

```
atgaagcact tggggctat attccttgtg cttttattag tcctcgcaac ggaacatgga     60
gcaagagtag cagaagcaag aacttgtgaa acgccaagtc aaaagttcaa aggcatctgt    120
atttccgact ccaattgtga aagcatttgc aataccgaag gatttccgaa tggagaatgt    180
tctggccttc gcagaagatg catttgcaac accccttgta cttaatag                228
```

<210> SEQ ID NO 55
<211> LENGTH: 177
<212> TYPE: DNA
<213> ORGANISM: Artificial Sequence
<220> FEATURE:
<223> OTHER INFORMATION: Def4 codon-optimized with VGD

<400> SEQUENCE: 55

```
atggtaagta caaaagttgc agaagcaagg atttgtgctt caccatctcc aacgtttaag    60
ggaatatgtt ttagtagccg taattgtgaa acgaattgca attccgtaaa attttctgga   120
ggaagttgtc agggttttag gagaagatgt atgtgcacaa agccctgcgc ttgatag      177
```

<210> SEQ ID NO 56
<211> LENGTH: 228
<212> TYPE: DNA
<213> ORGANISM: Artificial Sequence
<220> FEATURE:
<223> OTHER INFORMATION: Def5 codon-optimized with VGD

<400> SEQUENCE: 56

```
atgagaccat tgctgctct tttccttgtg cttttccttg tgttggctac agaaataggg    60
cccagggtgg tagaagcaag aatgtgctca gtccaagtc ataggttcaa gggcatttgc   120
acttcttcga gaaattgtga aaacacttgc aacagcgaac gattttcagg tggtgagtgt  180
aaaggctttc gcagaagatg tatgtgcacg ggaccctgtg tgtaatag               228
```

<210> SEQ ID NO 57
<211> LENGTH: 276
<212> TYPE: DNA
<213> ORGANISM: Artificial Sequence
<220> FEATURE:
<223> OTHER INFORMATION: Def6 codon-optimized with VGD

<400> SEQUENCE: 57

```
atggagaggt cttcacgtgt gttttcagtg gttctcctta tgttggttct tgtgttgagt    60
acagatatgt acacagaccc tgtagcagtt cttagttatg aaattgggac taaggtggca   120
gaagctcgca tttgtgaatc ggcaagttac aggttcaagg gaatatgtgt gtcaaggtca   180
aactgcgcta acgtttgcaa aaatgagggt ttcccaggtg gtcgttgccg gggatttaga   240
aggcggtgcc tttgctacaa acattgcggg tagtaa                             276
```

<210> SEQ ID NO 58
<211> LENGTH: 228
<212> TYPE: DNA
<213> ORGANISM: Artificial Sequence
<220> FEATURE:
<223> OTHER INFORMATION: Def7 codon-optimized with VGD

<400> SEQUENCE: 58

```
atgaagcctt tgtagctttt tgttctggct ttcatgcttg ttctcgccat agagatgggt    60
ccccgggtcg ctgaggcacg gatgtgcaca aatccgagca gaacattcag ggtccctgc   120 gttagcgaca ggaactgcga atcctcatgc atgggagagg gatttccggg tggtagttgc  180
catggattta aagaaaatg cgtttgcagc aagccttgtg cttagtaa                228
```

<210> SEQ ID NO 59
<211> LENGTH: 271
<212> TYPE: DNA
<213> ORGANISM: Artificial Sequence
<220> FEATURE:
<223> OTHER INFORMATION: Chimeric nucleic acid encoding a signal peptide
        and Def2 codon-optimized with Genscript

```
<220> FEATURE:
<221> NAME/KEY: misc_feature
<222> LOCATION: (1)..(6)
<223> OTHER INFORMATION: Restriction site for XbaI
<220> FEATURE:
<221> NAME/KEY: sig_peptide
<222> LOCATION: (14)..(70)
<223> OTHER INFORMATION: Def2 signal peptide
<220> FEATURE:
<221> NAME/KEY: misc_feature
<222> LOCATION: (71)..(259)
<223> OTHER INFORMATION: CDS of Genscript-optimized Def2 peptide
<220> FEATURE:
<221> NAME/KEY: misc_feature
<222> LOCATION: (266)..(271)
<223> OTHER INFORMATION: Restriction site for KpnI

<400> SEQUENCE: 59
tctagaaaca atgaagatgt caatgaggtc gatcgctgtg gttttcttgg tgtgcctatt      60
ggtgttgtca acagaggaga tgggtccaag gaaagccgac gctgggttct tcagttctaa    120
aaagtgcaaa acaccaagca aaacattcag aggcccttgc gttagaaatg ctaactgcga    180
tacttcttgt agatatgagg gttacccagc aggagactgc aagggtatta ggagaaggtg    240
tatctgctgt acacatgctt aatgaggtac c                                   271

<210> SEQ ID NO 60
<211> LENGTH: 267
<212> TYPE: DNA
<213> ORGANISM: Artificial Sequence
<220> FEATURE:
<223> OTHER INFORMATION: Chimeric nucleic acid encoding a signal peptide
      and Def2 codon-optimized with VGD
<220> FEATURE:
<221> NAME/KEY: misc_feature
<222> LOCATION: (1)..(6)
<223> OTHER INFORMATION: Restriction site for XbaI
<220> FEATURE:
<221> NAME/KEY: sig_peptide
<222> LOCATION: (10)..(66)
<223> OTHER INFORMATION: Def2 signal peptide
<220> FEATURE:
<221> NAME/KEY: misc_feature
<222> LOCATION: (67)..(255)
<223> OTHER INFORMATION: CDS of VGD-optimized Def2 peptide
<220> FEATURE:
<221> NAME/KEY: misc_feature
<222> LOCATION: (262)..(267)
<223> OTHER INFORMATION: Restriction site for KpnI

<400> SEQUENCE: 60
tctagaatga agatgtcaat gaggtcgatc gctgtggttt tcttggtgtg cctattggtg      60
ttgtcaacag aagagatggg cccgagaaaa gcagacgctg gatttttctc atccaagaaa    120
tgcaagacac cctcaaaaac attcagggga ccttgtgtaa ggaacgctaa ctgtgacact    180
tcttgtaggt atgagggcta tccagctgga gattgcaagg gtataaggag aagatgtatt    240
tgttgtaccc atgcttaata gggtacc                                        267

<210> SEQ ID NO 61
<211> LENGTH: 1493
<212> TYPE: DNA
<213> ORGANISM: Artificial Sequence
<220> FEATURE:
<223> OTHER INFORMATION: Chimeric nucleic acid encoding Def1
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
```

<220> FEATURE:
<221> NAME/KEY: misc_feature
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1084)
<223> OTHER INFORMATION: mat_peptide: Def1 peptide
<220> FEATURE:
<221> NAME/KEY: misc_feature
<222> LOCATION: (1085)..(1090)
<223> OTHER INFORMATION: Restriction site for KpnI
<220> FEATURE:
<221> NAME/KEY: 3'UTR
<222> LOCATION: (1091)..(1277)
<223> OTHER INFORMATION: TEV 3' UTR
<220> FEATURE:
<221> NAME/KEY: misc_feature
<222> LOCATION: (1278)..(1283)
<223> OTHER INFORMATION: Restriction site for SmaI
<220> FEATURE:
<221> NAME/KEY: terminator
<222> LOCATION: (1302)..(1493)
<223> OTHER INFORMATION: 35ST

<400> SEQUENCE: 61

```
cctgcaggtc aacatggtgg agcacgacac acttgtctac tccaaaaata tcaaagatac      60
agtctcagaa gaccaaaggg caattgagac ttttcaacaa agggtaatat ccggaaacct     120
cctcggattc cattgcccag ctatctgtca ctttattgtg aagatagtgg aaaaggaagg     180
tggctcctac aaatgccatc attgcgataa aggaaaggcc atcgttgaag atgcctctgc     240
cgacagtggt cccaaagatg acccccacc cacgaggagc atcgtggaaa agaagacgt      300
tccaaccacg tcttcaaagc aagtggattg atgtgataac atggtggagc acgacacact     360
tgtctactcc aaaaatatca agatacagt ctcagaagac caaagggcaa ttgagacttt     420
tcaacaaagg gtaatatccg gaaacctcct cggattccat gcccagcta tctgtcactt     480
tattgtgaag atagtggaaa aggaaggtgg ctcctacaaa tgccatcatt gcgataaagg     540
aaaggccatc gttgaagatg cctctgccga cagtggtccc aaagatggac ccccaccccac     600
gaggagcatc gtggaaaaag aagacgttcc aaccacgtct tcaaagcaag tggattgatg     660
tgatatctcc actgacgtaa gggatgacgc acaatcccac tatccttcgc aagacccttc     720
ctctatataa ggaagttcat ttcatttgga gaggaccctc aacacaacat atacaaaaca     780
aacgaatctc aagcaatcaa gcattctact tctattgcag caatttaaat catttctttt     840
aaagcaaaag caatttttctg aaaatttca ccatttacga acgatagctc tagaaacaat     900
ggggccaaga aaagccgaag ccgggatatt cagctcaaga agtgcaagac acccctccaa     960
gacattcaaa ggcatctgta ccagggattc taattgcgac acctcatgta gatatgaggg    1020
ttaccctgct ggagattgca agggtattag agaaggtgt ctttgctgta ctcatacata    1080
atgaggtacc tagtttctgc gtgtctttgc tttccgcttt tatgcttatt gtaatatata    1140
tgaatagcta tttacagtgg gacttggtct tgtgttgaat agtatcttat atgtttaat    1200
atgtcttatt agtctcatta cttaggcgaa cgacaaagtg aggttacctc ggtctaactc    1260
tcctatgtag tgcgagaccc ggggtccgca aaaatcacca gtctctctct acaaatctat    1320
ctctctctat ttttctccag aataatgtgt gagtagttcc cagataaggg aattagggtt    1380
cttatagggt ttcgctcatg tgttgagcat ataagaaacc cttagtatgt atttgtattt    1440
gtaaaatact tctatcaata aaatttctaa ttcctaaaac caaaatccag tga           1493
```

<210> SEQ ID NO 62
<211> LENGTH: 1505
<212> TYPE: DNA
<213> ORGANISM: Artificial Sequence
<220> FEATURE:
<223> OTHER INFORMATION: Chimeric nucleic acid encoding Def2
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1096)
<223> OTHER INFORMATION: mat_peptide: Def2 peptide
<220> FEATURE:
<221> NAME/KEY: misc_feature
<222> LOCATION: (1097)..(1102)
<223> OTHER INFORMATION: Restriction site for KpnI
<220> FEATURE:
<221> NAME/KEY: 3'UTR
<222> LOCATION: (1103)..(1289)
<223> OTHER INFORMATION: TEV 3' UTR
<220> FEATURE:
<221> NAME/KEY: misc_feature
<222> LOCATION: (1290)..(1295)
<223> OTHER INFORMATION: Restriction site for SmaI
<220> FEATURE:
<221> NAME/KEY: terminator
<222> LOCATION: (1314)..(1505)
<223> OTHER INFORMATION: 35ST

<400> SEQUENCE: 62

```
cctgcaggtc aacatggtgg agcacgacac acttgtctac tccaaaaata tcaaagatac      60
agtctcagaa gaccaaaggg caattgagac ttttcaacaa agggtaatat ccggaaacct     120
cctcggattc cattgcccag ctatctgtca ctttattgtg aagatagtgg aaaaggaagg     180
tggctcctac aaatgccatc attgcgataa aggaaaggcc atcgttgaag atgcctctgc     240
cgacagtggt cccaaagatg acccccacc cacgaggagc atcgtggaaa agaagacgt      300
tccaaccacg tcttcaaagc aagtggattg atgtgataac atggtggagc acgacacact    360
tgtctactcc aaaaatatca agatacagt ctcagaagac caagggcaa ttgagacttt      420
tcaacaaagg gtaatatccg gaaacctcct cggattccat gcccagcta tctgtcactt     480
tattgtgaag atagtggaaa aggaaggtgg ctcctacaaa tgccatcatt gcgataaagg    540
aaaggccatc gttgaagatg cctctgccga cagtggtccc aaagatggac ccccacccac    600
gaggagcatc gtggaaaaag aagacgttcc aaccacgtct tcaaagcaag tggattgatg    660
tgatatctcc actgacgtaa gggatgacgc acaatcccac tatccttcgc aagaccttc     720
ctctatataa ggaagttcat ttcatttgga gaggaccctc aacacaacat atacaaaaca    780
aacgaatctc aagcaatcaa gcattctact tctattgcag caatttaaat catttctttt    840
aaagcaaaag caattttctg aaattttca ccatttacga acgatagctc tagaaacaat     900
gacagaggag atgggtccaa ggaaagccga cgctggggttc ttcagttcta aaaagtgcaa    960
aacaccaagc aaaacattca gaggcccttg cgttagaaat gctaactgcg atacttcttg    1020
tagatatgag ggttacccag caggagactg caagggtatt aggagaaggt gtatctgctg    1080
tacacatgct taatgaggta cctagttct gcgtgtcttt gctttccgct tttatgctta    1140
```

-continued

```
ttgtaatata tatgaatagc tatttacagt gggacttggt cttgtgttga atagtatctt    1200
atatgtttta atatgtctta ttagtctcat tacttaggcg aacgacaaag tgaggttacc    1260
tcggtctaac tctcctatgt agtgcgagac ccggggtccg caaaaatcac cagtctctct    1320
ctacaaatct atctctctct atttttctcc agaataatgt gtgagtagtt cccagataag    1380
ggaattaggg ttcttatagg gtttcgctca tgtgttgagc atataagaaa cccttagtat    1440
gtatttgtat ttgtaaaata cttctatcaa taaaatttct aattcctaaa accaaaatcc    1500
agtga                                                                1505
```

<210> SEQ ID NO 63
<211> LENGTH: 1535
<212> TYPE: DNA
<213> ORGANISM: Artificial Sequence
<220> FEATURE:
<223> OTHER INFORMATION: Chimeric nucleic acid encoding Def3
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5'UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1126)
<223> OTHER INFORMATION: mat_peptide: Def3 peptide
<220> FEATURE:
<221> NAME/KEY: misc_feature
<222> LOCATION: (1127)..(1132)
<223> OTHER INFORMATION: Restriction site for KpnI
<220> FEATURE:
<221> NAME/KEY: 3'UTR
<222> LOCATION: (1133)..(1319)
<223> OTHER INFORMATION: TEV 3' UTR
<220> FEATURE:
<221> NAME/KEY: misc_feature
<222> LOCATION: (1320)..(1325)
<223> OTHER INFORMATION: Restriction site for SmaI
<220> FEATURE:
<221> NAME/KEY: terminator
<222> LOCATION: (1344)..(1535)
<223> OTHER INFORMATION: 35ST

<400> SEQUENCE: 63

```
cctgcaggtc aacatggtgg agcacgacac acttgtctac tccaaaaata tcaaagatac      60
agtctcagaa gaccaaaggg caattgagac ttttcaacaa agggtaatat ccggaaacct     120
cctcggattc cattgcccag ctatctgtca ctttattgtg aagatagtgg aaaaggaagg     180
tggctcctac aaatgccatc attgcgataa aggaaaggcc atcgttgaag atgcctctgc     240
cgacagtggt cccaaagatg acccccacc cacgaggagc atcgtggaaa agaagacgt       300 tccaaccacg tcttcaaagc aagtggattg atgtgataac atggtggagc acgacacact     360
tgtctactcc aaaaatatca agatacagt ctcagaagac caagggcaa ttgagacttt       420 tcaacaaagg gtaatatccg gaaacctcct cggattccat gcccagcta tctgtcactt     480 tattgtgaag atagtggaaa aggaaggtgg ctcctacaaa tgccatcatt gcgataaagg     540
aaaggccatc gttgaagatg cctctgccga cagtggtccc aaagatggac ccccacccac     600
gaggagcatc gtggaaaaag aagacgttcc aaccacgtct tcaaagcaag tggattgatg     660
```

```
tgatatctcc actgacgtaa gggatgacgc acaatcccac tatccttcgc aagacccttc    720
ctctatataa ggaagttcat ttcatttgga gaggaccctc aacacaacat atacaaaaca    780
aacgaatctc aagcaatcaa gcattctact tctattgcag caatttaaat catttctttt    840
aaagcaaaag caattttctg aaaattttca ccatttacga acgatagctc tagaaacaat    900
gaaacacttc ggggctatct ttttggtgct cctgctcgtg ctcgctactg aacatggtgc    960
cagagttgct gaggctagaa cctgtgaaac cccctctcaa aagtttaaag gtatctgcat   1020
ctctgattca aactgcgaga gcatatgtaa cacagaaggt ttccctaatg gtgaatgcag   1080
tggccttagg agaaggtgca tctgtaacac tccatgtaca taatgaggta cctagtttct   1140
gcgtgtcttt gctttccgct tttatgctta ttgtaatata tatgaatagc tatttacagt   1200
gggacttggt cttgtgttga atagtatctt atatgtttta atatgtctta ttagtctcat   1260
tacttaggcg aacgacaaag tgaggttacc tcggtctaac tctcctatgt agtgcgagac   1320
ccggggtccg caaaaatcac cagtctctct ctacaaatct atctctctct attttctcc   1380 agaataatgt gtgagtagtt cccagataag ggaattaggg ttcttatagg gtttcgctca   1440
tgtgttgagc atataagaaa cccttagtat gtatttgtat ttgtaaaata cttctatcaa   1500
taaaatttct aattcctaaa accaaaatcc agtga                              1535

<210> SEQ ID NO 64
<211> LENGTH: 1535
<212> TYPE: DNA
<213> ORGANISM: Artificial Sequence
<220> FEATURE:
<223> OTHER INFORMATION: Chimeric nucleic acid encoding Def5
<220> FEATURE:
<221> NAME/KEY: Promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1126)
<223> OTHER INFORMATION: mat_peptide: Def5 peptide
<220> FEATURE:
<221> NAME/KEY: misc_feature
<222> LOCATION: (1127)..(1132)
<223> OTHER INFORMATION: Restriction site for KpnI
<220> FEATURE:
<221> NAME/KEY: 3'UTR
<222> LOCATION: (1133)..(1319)
<223> OTHER INFORMATION: TEV 3' UTR
<220> FEATURE:
<221> NAME/KEY: misc_feature
<222> LOCATION: (1320)..(1325)
<223> OTHER INFORMATION: Restriction site for SmaI
<220> FEATURE:
<221> NAME/KEY: terminator
<222> LOCATION: (1344)..(1535)
<223> OTHER INFORMATION: 35ST

<400> SEQUENCE: 64
cctgcaggtc aacatggtgg agcacgacac acttgtctac tccaaaaata tcaaagatac     60
agtctcagaa gaccaaaggg caattgagac ttttcaacaa agggtaatat ccggaaacct    120
cctcggattc cattgcccag ctatctgtca ctttattgtg aagatagtgg aaaaggaagg    180
tggctcctac aaatgccatc attgcgataa aggaaaggcc atcgttgaag atgcctctgc    240
```

```
cgacagtggt cccaaagatg gacccccacc cacgaggagc atcgtggaaa aagaagacgt      300
tccaaccacg tcttcaaagc aagtggattg atgtgataac atggtggagc acgacacact      360
tgtctactcc aaaaatatca aagatacagt ctcagaagac caaagggcaa ttgagacttt      420
tcaacaaagg gtaatatccg gaaacctcct cggattccat tgcccagcta tctgtcactt      480
tattgtgaag atagtggaaa aggaaggtgg ctcctacaaa tgccatcatt gcgataaagg      540
aaaggccatc gttgaagatg cctctgccga cagtggtccc aaagatggac ccccacccac      600
gaggagcatc gtggaaaaag aagacgttcc aaccacgtct tcaaagcaag tggattgatg      660
tgatatctcc actgacgtaa gggatgacgc acaatcccac tatccttcgc aagacccttc      720
ctctatataa ggaagttcat tcatttgga gaggaccctc aacacaacat atacaaaaca       780
aacgaatctc aagcaatcaa gcattctact tctattgcag caatttaaat catttctttt      840
aaagcaaaag caattttctg aaaattttca ccatttacga acgatagctc tagaaacaat      900
gagacccttc gccgctttgt ttttggtttt gttcttggtg ctcgctacag agattggacc      960
cagagtggtg gaggccagga tgtgttcttc acctagccat aggtttaagg gtatttgcac     1020
tagcagtagg aattgcgaga acacatgtaa ttccgaaaga ttttctggtg gagagtgcaa     1080
aggcttcagg agaaggtgca tgtgtaccgg gccatgtgtt taatgaggta cctagtttct     1140
gcgtgtcttt gctttccgct tttatgctta ttgtaatata tatgaatagc tatttacagt     1200
gggacttggt cttgtgttga atagtatctt atatgtttta atatgtctta ttagtctcat     1260
tacttaggcg aacgacaaag tgaggttacc tcggtctaac tctcctatgt agtgcgagac     1320
ccggggtccg caaaaatcac cagtctctct ctacaaatct atctctctct attttctcc     1380 agaataatgt gtgagtagtt cccagataag ggaattaggg ttcttatagg gtttcgctca     1440
tgtgttgagc atataagaaa cccttagtat gtatttgtat ttgtaaaata cttctatcaa     1500
taaaatttct aattcctaaa accaaaatcc agtga                                 1535

<210> SEQ ID NO 65
<211> LENGTH: 1583
<212> TYPE: DNA
<213> ORGANISM: Artificial Sequence
<220> FEATURE:
<223> OTHER INFORMATION: Chimeric nucleic acid encoding Def6
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1174)
<223> OTHER INFORMATION: mat_peptide: Def6 peptide
<220> FEATURE:
<221> NAME/KEY: misc_feature
<222> LOCATION: (1175)..(1180)
<223> OTHER INFORMATION: Restriction site for KpnI
<220> FEATURE:
<221> NAME/KEY: 3'UTR
<222> LOCATION: (1181)..(1367)
<223> OTHER INFORMATION: TEV 3' UTR
<220> FEATURE:
<221> NAME/KEY: misc_feature
<222> LOCATION: (1368)..(1373)
```

<223> OTHER INFORMATION: Restriction site for SmaI
<220> FEATURE:
<221> NAME/KEY: terminator
<222> LOCATION: (1392)..(1583)
<223> OTHER INFORMATION: 35ST

<400> SEQUENCE: 65

```
cctgcaggtc aacatggtgg agcacgacac acttgtctac tccaaaaata tcaaagatac    60
agtctcagaa gaccaaaggg caattgagac ttttcaacaa agggtaatat ccggaaacct   120
cctcggattc cattgcccag ctatctgtca ctttattgtg aagatagtgg aaaaggaagg   180
tggctcctac aaatgccatc attgcgataa aggaaaggcc atcgttgaag atgcctctgc   240
cgacagtggt cccaaagatg acccccacc cacgaggagc atcgtggaaa agaagacgt    300
tccaaccacg tcttcaaagc aagtggattg atgtgataac atggtggagc acgacacact   360
tgtctactcc aaaaatatca agatacagt ctcagaagac caaagggcaa ttgagacttt   420
tcaacaaagg gtaatatccg gaaacctcct cggattccat tgcccagcta tctgtcactt   480
tattgtgaag atagtggaaa aggaaggtgg ctcctacaaa tgccatcatt gcgataaagg   540
aaaggccatc gttgaagatg cctctgccga cagtggtccc aaagatggac ccccacccac   600
gaggagcatc gtggaaaaag aagacgttcc aaccacgtct tcaaagcaag tggattgatg   660
tgatatctcc actgacgtaa gggatgacgc acaatcccac tatccttcgc aagacccttc   720
ctctatataa ggaagttcat ttcatttgga gaggaccctc aacacaacat atacaaaaca   780
aacgaatctc aagcaatcaa gcattctact tctattgcag caatttaaat catttctttt   840
aaagcaaaag caattttctg aaaattttca ccatttacga acgatagctc tagaaacaat   900
ggagagatcg tcaagagttt ttagcgttgt gctgcttatg ctggtgctgg ttctgtctac   960
tgatatgtat accgaccctg tggctgttct ttcttatgag attggtacta aggtggctga  1020
ggcaagaatc tgcgaatctg cctcatacag gtttaagggc atttgtgtta gcagaagtaa  1080
ttgcgcaaac gtgtgcaaga atgagggctt tcctggtgga agatgcaggg ggttcaggag  1140
aaggtgcttg tgttataagc attgtggtta atgaggtacc tagtttctgc gtgtctttgc  1200
tttccgcttt tatgcttatt gtaatatata tgaatagcta tttacagtgg gacttggtct  1260
tgtgttgaat agtatcttat atgtttaat atgtcttatt agtctcatta cttaggcgaa  1320
cgacaaagtg aggttacctc ggtctaactc tcctatgtag tgcgagaccc ggggtccgca  1380
aaaatcacca gtctctctct acaaatctat ctctctctat ttttctccag aataatgtgt  1440
gagtagttcc cagataaggg aattagggtt cttatagggt ttcgctcatg tgttgagcat  1500
ataagaaacc cttagtatgt atttgtattt gtaaaatact tctatcaata aaatttctaa  1560
ttcctaaaac caaaatccag tga                                          1583
```

<210> SEQ ID NO 66
<211> LENGTH: 1535
<212> TYPE: DNA
<213> ORGANISM: Artificial Sequence
<220> FEATURE:
<223> OTHER INFORMATION: Chimeric nucleic acid encoding Def7
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1126)
<223> OTHER INFORMATION: mat_peptide: Def7 peptide
<220> FEATURE:
<221> NAME/KEY: misc_feature
<222> LOCATION: (1127)..(1132)
<223> OTHER INFORMATION: Restriction site for KpnI
<220> FEATURE:
<221> NAME/KEY: 3'UTR
<222> LOCATION: (1133)..(1319)
<223> OTHER INFORMATION: TEV 3' UTR
<220> FEATURE:
<221> NAME/KEY: misc_feature
<222> LOCATION: (1320)..(1325)
<223> OTHER INFORMATION: Restriction site for SmaI
<220> FEATURE:
<221> NAME/KEY: terminator
<222> LOCATION: (1344)..(1535)
<223> OTHER INFORMATION: 35ST

<400> SEQUENCE: 66

```
cctgcaggtc aacatggtgg agcacgacac acttgtctac tccaaaaata tcaaagatac      60
agtctcagaa gaccaaaggg caattgagac ttttcaacaa agggtaatat ccggaaacct     120
cctcggattc cattgcccag ctatctgtca ctttattgtg aagatagtgg aaaaggaagg     180
tggctcctac aaatgccatc attgcgataa aggaaaggcc atcgttgaag atgcctctgc     240
cgacagtggt cccaaagatg acccccacc cacgaggagc atcgtggaaa agaagacgt      300
tccaaccacg tcttcaaagc aagtggattg atgtgataac atggtggagc acgacacact    360
tgtctactcc aaaaatatca agatacagt ctcagaagac caaagggcaa ttgagacttt    420
tcaacaaagg gtaatatccg gaaacctcct cggattccat gcccagcta tctgtcactt     480
tattgtgaag atagtggaaa aggaaggtgg ctcctacaaa tgccatcatt gcgataaagg    540
aaaggccatc gttgaagatg cctctgccga cagtggtccc aaagatggac ccccacccac    600
gaggagcatc gtggaaaaag aagacgttcc aaccacgtct tcaaagcaag tggattgatg    660
tgatatctcc actgacgtaa gggatgacgc acaatcccac tatccttcgc aagacccttc    720
ctctatataa ggaagttcat ttcatttgga gaggaccctc aacacaacat atacaaaaca    780
aacgaatctc aagcaatcaa gcattctact tctattgcag caatttaaat catttctttt    840
aaagcaaaag caatttttctg aaaattttca ccatttacga acgatagctc tagaaacaat    900
gaaacctttt gtggcttttg tgctggcttt tatgctcgtt ctggctattg aaatgggtcc    960
aagagtggct gaggcaagga tgtgtactaa tccttctagg actttaggg gtccatgcgt    1020
tagtgatagg aactgcgagt cttcatgtat gggcgaaggg tttccggtg gatcttgcca    1080
tggcttcagg agaaagtgcg tgtgttctaa accttgtgct taatgaggta cctagtttct    1140
gcgtgtcttt gctttccgct tttatgctta ttgtaatata tatgaatagc tatttacagt    1200
gggacttggt cttgtgttga atagtatctt atatgtttta atatgtctta ttagtctcat    1260
tacttaggcg aacgacaaag tgaggttacc tcggtctaac tctcctatgt agtgcgagac    1320
ccggggtccg caaaaatcac cagtctctct ctacaaatct atctctctct attttctcc    1380
agaataatgt gtgagtagtt cccagataag ggaattaggg ttcttatagg gtttcgctca    1440
tgtgttgagc atataagaaa cccttagtat gtatttgtat ttgtaaaata cttctatcaa    1500
taaaatttct aattcctaaa accaaaatcc agtga                               1535
```

<210> SEQ ID NO 67

```
<211> LENGTH: 1489
<212> TYPE: DNA
<213> ORGANISM: Artificial Sequence
<220> FEATURE:
<223> OTHER INFORMATION: Chimeric nucleic acid encoding Def1
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1080)
<223> OTHER INFORMATION: mat_peptide: Def1 peptide
<220> FEATURE:
<221> NAME/KEY: misc_feature
<222> LOCATION: (1081)..(1086)
<223> OTHER INFORMATION: Restriction site for KpnI
<220> FEATURE:
<221> NAME/KEY: 3'UTR
<222> LOCATION: (1087)..(1273)
<223> OTHER INFORMATION: TEV 3' UTR
<220> FEATURE:
<221> NAME/KEY: misc_feature
<222> LOCATION: (1274)..(1279)
<223> OTHER INFORMATION: Restriction site for SmaI
<220> FEATURE:
<221> NAME/KEY: terminator
<222> LOCATION: (1298)..(1489)
<223> OTHER INFORMATION: 35ST

<400> SEQUENCE: 67
cctgcaggtc aacatggtgg agcacgacac acttgtctac tccaaaaata tcaaagatac      60
agtctcagaa gaccaaaggg caattgagac ttttcaacaa agggtaatat ccggaaacct     120
cctcggattc cattgcccag ctatctgtca ctttattgtg aagatagtgg aaaaggaagg     180
tggctcctac aaatgccatc attgcgataa aggaaaggcc atcgttgaag atgcctctgc     240
cgacagtggt cccaaagatg acccccacc cacgaggagc atcgtggaaa agaagacgt      300 tccaaccacg tcttcaaagc aagtggattg atgtgataac atggtggagc acgacacact     360
tgtctactcc aaaaatatca agatacagt ctcagaagac caaagggcaa ttgagacttt      420
tcaacaaagg gtaatatccg gaaacctcct cggattccat gcccagcta tctgtcactt      480 tattgtgaag atagtggaaa aggaaggtgg ctcctacaaa tgccatcatt gcgataaagg     540
aaaggccatc gttgaagatg cctctgccga cagtggtccc aaagatggac ccccacccac     600
gaggagcatc gtggaaaaag aagacgttcc aaccacgtct tcaaagcaag tggattgatg     660
tgatatctcc actgacgtaa gggatgacgc acaatcccac tatccttcgc aagaccctc     720 ctctatataa ggaagttcat ttcatttgga gaggaccctc aacacaacat atacaaaaca     780
aacgaatctc aagcaatcaa gcattctact tctattgcag caatttaaat catttctttt     840
aaagcaaaag caattttctg aaaattttca ccatttacga acgatagctc tagaatgggt     900
cctaggaagg cagaggctgg aatatttagc tcgaggaagt gcaaaacccc aagtaaaacg     960
tttaagggaa tttgtactag agactccaat tgtgacactt cgtgtaggta tgagggatac    1020
ccagctggag attgcaaggg tatcaggaga aggtgcttat gctgtacaca tacataatag    1080 ggtaccctagt ttctgcgtgt ctttgctttc cgcttttatg cttattgtaa tatatatgaa    1140 tagctatttta cagtgggact tggtcttgtg ttgaatagta tcttatatgt tttaatatgt    1200
```

```
cttattagtc tcattactta ggcgaacgac aaagtgaggt tacctcggtc taactctcct    1260
atgtagtgcg agacccgggg tccgcaaaaa tcaccagtct ctctctacaa atctatctct    1320
ctctattttt ctccagaata atgtgtgagt agttcccaga taagggaatt agggttctta    1380
tagggtttcg ctcatgtgtt gagcatataa gaaaccctta gtatgtattt gtatttgtaa    1440
aatacttcta tcaataaaat ttctaattcc taaaaccaaa atccagtga                1489
```

```
<210> SEQ ID NO 68
<211> LENGTH: 1501
<212> TYPE: DNA
<213> ORGANISM: Artificial Sequence
<220> FEATURE:
<223> OTHER INFORMATION: Chimeric nucleic acid encoding Def2
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1092)
<223> OTHER INFORMATION: mat_peptide: Def2 peptide
<220> FEATURE:
<221> NAME/KEY: misc_feature
<222> LOCATION: (1093)..(1098)
<223> OTHER INFORMATION: Restriction site for KpnI
<220> FEATURE:
<221> NAME/KEY: 3'UTR
<222> LOCATION: (1099)..(1285)
<223> OTHER INFORMATION: TEV 3' UTR
<220> FEATURE:
<221> NAME/KEY: misc_feature
<222> LOCATION: (1286)..(1291)
<223> OTHER INFORMATION: Restriction site for SmaI
<220> FEATURE:
<221> NAME/KEY: terminator
<222> LOCATION: (1310)..(1501)
<223> OTHER INFORMATION: 35ST

<400> SEQUENCE: 68
cctgcaggtc aacatggtgg agcacgacac acttgtctac tccaaaaata tcaaagatac      60
agtctcagaa gaccaaaggg caattgagac ttttcaacaa agggtaatat ccggaaacct     120
cctcggattc cattgcccag ctatctgtca ctttattgtg aagatagtgg aaaaggaagg     180
tggctcctac aaatgccatc attgcgataa aggaaaggcc atcgttgaag atgcctctgc     240
cgacagtggt cccaaagatg gacccccacc cacgaggagc atcgtggaaa agaagacgt      300 tccaaccacg tcttcaaagc aagtggattg atgtgataac atggtggagc acgacacact     360
tgtctactcc aaaaatatca agatacagt  ctcagaagac caaagggcaa ttgagacttt     420
tcaacaaagg gtaatatccg gaaacctcct cggattccat gcccagcta tctgtcactt      480 tattgtgaag atagtggaaa aggaaggtgg ctcctacaaa tgccatcatt gcgataaagg     540
aaaggccatc gttgaagatg cctctgccga cagtggtccc aaagatggac ccccacccac     600
gaggagcatc gtggaaaaag aagacgttcc aaccacgtct tcaaagcaag tggattgatg     660
tgatatctcc actgacgtaa gggatgacgc acaatcccac tatccttcgc aagacccttc     720
ctctatataa ggaagttcat ttcatttgga gaggaccctc aacacaacat atacaaaaca     780
```

```
aacgaatctc aagcaatcaa gcattctact tctattgcag caatttaaat catttctttt      840
aaagcaaaag caattttctg aaaattttca ccatttacga acgatagctc tagaatgaca      900
gaagagatgg gcccgagaaa agcagacgct ggattttcct catccaagaa atgcaagaca      960
ccctcaaaaa cattcagggg accttgtgta aggaacgcta actgtgacac ttcttgtagg     1020
tatgagggct atccagctgg agattgcaag ggtataagga gaagatgtat ttgttgtacc     1080
catgcttaat agggtaccta gtttctgcgt gtctttgctt ccgctttta tgcttattgt      1140 aatatatatg aatagctatt tacagtggga cttggtcttg tgttgaatag tatcttatat     1200
gttttaatat gtcttattag tctcattact taggcgaacg acaaagtgag gttacctcgg     1260
tctaactctc ctatgtagtg cgagacccgg ggtccgcaaa atcaccagt ctctctctac      1320 aaatctatct ctctctattt ttctccagaa taatgtgtga gtagttccca gataagggaa     1380
ttagggttct tatagggttt cgctcatgtg ttgagcatat aagaaaccct tagtatgtat     1440
ttgtatttgt aaaatacttc tatcaataaa atttctaatt cctaaaacca aaatccagtg     1500
a                                                                    1501

<210> SEQ ID NO 69
<211> LENGTH: 1531
<212> TYPE: DNA
<213> ORGANISM: Artificial Sequence
<220> FEATURE:
<223> OTHER INFORMATION: Chimeric nucleic acid encoding Def3
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1122)
<223> OTHER INFORMATION: mat_peptide: Def3 peptide
<220> FEATURE:
<221> NAME/KEY: misc_feature
<222> LOCATION: (1123)..(1128)
<223> OTHER INFORMATION: Restriction site for KpnI
<220> FEATURE:
<221> NAME/KEY: 3'UTR
<222> LOCATION: (1129)..(1315)
<223> OTHER INFORMATION: TEV 3' UTR
<220> FEATURE:
<221> NAME/KEY: misc_feature
<222> LOCATION: (1316)..(1321)
<223> OTHER INFORMATION: Restriction site for SmaI
<220> FEATURE:
<221> NAME/KEY: terminator
<222> LOCATION: (1340)..(1531)
<223> OTHER INFORMATION: 35ST

<400> SEQUENCE: 69
cctgcaggtc aacatggtgg agcacgacac acttgtctac tccaaaaata tcaaagatac       60
agtctcagaa gaccaaaggg caattgagac ttttcaacaa agggtaatat ccggaaacct      120
cctcggattc cattgcccag ctatctgtca ctttattgtg aagatagtgg aaaaggaagg      180
tggctcctac aaatgccatc attgcgataa aggaaaggcc atcgttgaag atgcctctgc      240
cgacagtggt cccaaagatg gacccccacc cacgaggagc atcgtggaaa agagaagacgt     300 tccaaccacg tcttcaaagc aagtggattg atgtgataac atggtggagc acgacacact      360
```

```
tgtctactcc aaaaatatca aagatacagt ctcagaagac caaagggcaa ttgagacttt    420
tcaacaaagg gtaatatccg gaaacctcct cggattccat tgcccagcta tctgtcactt    480
tattgtgaag atagtggaaa aggaaggtgg ctcctacaaa tgccatcatt gcgataaagg    540
aaaggccatc gttgaagatg cctctgccga cagtggtccc aaagatggac ccccacccac    600
gaggagcatc gtggaaaaag aagacgttcc aaccacgtct tcaaagcaag tggattgatg    660
tgatatctcc actgacgtaa gggatgacgc acaatcccac tatccttcgc aagacccttc    720
ctctatataa ggaagttcat ttcatttgga gaggaccctc aacacaacat atacaaaaca    780
aacgaatctc aagcaatcaa gcattctact tctattgcag caatttaaat catttctttt    840
aaagcaaaag caattttctg aaaattttca ccatttacga acgatagctc tagaatgaag    900
cactttgggg ctatattcct tgtgctttta ttagtcctcg caacggaaca tggagcaaga    960
gtagcagaag caagaacttg tgaaacgcca agtcaaaagt tcaaaggcat ctgtatttcc    1020
gactccaatt gtgaaagcat ttgcaatacc gaaggatttc cgaatggaga atgttctggc    1080
cttcgcagaa gatgcatttg caacaccccct tgtacttaat agggtaccta gtttctgcgt    1140
gtctttgctt tccgcttttta tgcttattgt aatatatatg aatagctatt tacagtggga    1200
cttggtcttg tgttgaatag tatcttatat gttttaatat gtcttattag tctcattact    1260
taggcgaacg acaaagtgag gttacctcgg tctaactctc ctatgtagtg cgagacccgg    1320
ggtccgcaaa aatcaccagt ctctctctac aaatctatct ctctctattt ttctccagaa    1380
taatgtgtga gtagttccca gataagggaa ttagggttct tatagggttt cgctcatgtg    1440
ttgagcatat aagaaaccct tagtatgtat ttgtatttgt aaaatacttc tatcaataaa    1500
atttctaatt cctaaaacca aaatccagtg a                                   1531
```

<210> SEQ ID NO 70
<211> LENGTH: 1480
<212> TYPE: DNA
<213> ORGANISM: Artificial Sequence
<220> FEATURE:
<223> OTHER INFORMATION: Chimeric nucleic acid encoding Def4
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1071)
<223> OTHER INFORMATION: mat_peptide: Def4 peptide
<220> FEATURE:
<221> NAME/KEY: misc_feature
<222> LOCATION: (1072)..(1077)
<223> OTHER INFORMATION: Restriction site for KpnI
<220> FEATURE:
<221> NAME/KEY: 3'UTR
<222> LOCATION: (1078)..(1264)
<223> OTHER INFORMATION: TEV 3' UTR
<220> FEATURE:
<221> NAME/KEY: misc_feature
<222> LOCATION: (1265)..(1270)
<223> OTHER INFORMATION: Restriction site for SmaI
<220> FEATURE:
<221> NAME/KEY: terminator
<222> LOCATION: (1289)..(1480)

-continued

<223> OTHER INFORMATION: 35ST

<400> SEQUENCE: 70

```
cctgcaggtc aacatggtgg agcacgacac acttgtctac tccaaaaata tcaaagatac      60
agtctcagaa gaccaaaggg caattgagac ttttcaacaa agggtaatat ccggaaacct     120
cctcggattc cattgcccag ctatctgtca ctttattgtg aagatagtgg aaaaggaagg     180
tggctcctac aaatgccatc attgcgataa aggaaaggcc atcgttgaag atgcctctgc     240
cgacagtggt cccaaagatg acccccacc cacgaggagc atcgtggaaa agaagacgt      300
tccaaccacg tcttcaaagc aagtggattg atgtgataac atggtggagc acgacacact     360
tgtctactcc aaaaatatca agatacagt ctcagaagac caaagggcaa ttgagacttt      420
tcaacaaagg gtaatatccg gaaacctcct cggattccat gcccagcta tctgtcactt      480
tattgtgaag atagtggaaa aggaaggtgg ctcctacaaa tgccatcatt gcgataaagg     540
aaaggccatc gttgaagatg cctctgccga cagtggtccc aaagatggac ccccacccac     600
gaggagcatc gtggaaaaag aagacgttcc aaccacgtct tcaaagcaag tggattgatg     660
tgatatctcc actgacgtaa gggatgacgc acaatcccac tatccttcgc aagacccttc     720
ctctatataa ggaagttcat ttcatttgga gaggaccctc aacacaacat atacaaaaca     780
aacgaatctc aagcaatcaa gcattctact tctattgcag caatttaaat catttctttt     840
aaagcaaaag caattttctg aaaatttttca ccatttacga acgatagctc tagaatggta     900
agtacaaaag ttgcagaagc aaggatttgt gcttcaccat ctccaacgtt taagggaata     960
tgttttagta gccgtaattg tgaaacgaat tgcaattccg taaaattttc tggaggaagt    1020
tgtcagggtt ttaggagaag atgtatgtgc acaaagccct gcgcttgata gggtacctag    1080
tttctgcgtg tctttgcttt ccgctttat gcttattgta atatatatga atagctattt     1140
acagtgggac ttggtcttgt gttgaatagt atcttatatg ttttaatatg tcttattagt    1200
ctcattactt aggcgaacga caaagtgagg ttacctcggt ctaactctcc tatgtagtgc    1260
gagacccggg gtccgcaaaa atcaccagtc tctctctaca aatctatctc tctctatttt    1320
tctccagaat aatgtgtgag tagttcccag ataagggaat tagggttctt atagggtttc    1380
gctcatgtgt tgagcatata agaaacccctt agtatgtatt tgtatttgta aaatacttct    1440
atcaataaaa tttctaattc ctaaaaccaa aatccagtga                           1480
```

<210> SEQ ID NO 71
<211> LENGTH: 1531
<212> TYPE: DNA
<213> ORGANISM: Artificial Sequence
<220> FEATURE:
<223> OTHER INFORMATION: Chimeric nucleic acid encoding Def5
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1122)
<223> OTHER INFORMATION: mat_peptide: Def5 peptide
<220> FEATURE:
<221> NAME/KEY: misc_feature
<222> LOCATION: (1123)..(1128)
<223> OTHER INFORMATION: Restriction site for KpnI
<220> FEATURE:
<221> NAME/KEY: 3'UTR
<222> LOCATION: (1129)..(1315)
<223> OTHER INFORMATION: TEV 3' UTR
<220> FEATURE:
<221> NAME/KEY: misc_feature
<222> LOCATION: (1316)..(1321)
<223> OTHER INFORMATION: Restriction site for SmaI
<220> FEATURE:
<221> NAME/KEY: terminator
<222> LOCATION: (1340)..(1531)
<223> OTHER INFORMATION: 35ST

<400> SEQUENCE: 71

```
cctgcaggtc aacatggtgg agcacgacac acttgtctac tccaaaaata tcaaagatac    60
agtctcagaa gaccaaaggg caattgagac ttttcaacaa agggtaatat ccggaaacct   120
cctcggattc cattgcccag ctatctgtca ctttattgtg aagatagtgg aaaaggaagg   180
tggctcctac aaatgccatc attgcgataa aggaaaggcc atcgttgaag atgcctctgc   240
cgacagtggt cccaaagatg acccccacc cacgaggagc atcgtggaaa agaagacgt    300
tccaaccacg tcttcaaagc aagtggattg atgtgataac atggtggagc acgacacact   360
tgtctactcc aaaaatatca agatacagt ctcagaagac caaagggcaa ttgagacttt    420
tcaacaaagg gtaatatccg gaaacctcct cggattccat gcccagcta tctgtcactt    480
tattgtgaag atagtggaaa aggaaggtgg ctcctacaaa tgccatcatt gcgataaagg   540
aaaggccatc gttgaagatg cctctgccga cagtggtccc aaagatggac ccccacccac   600
gaggagcatc gtggaaaaag aagacgttcc aaccacgtct tcaaagcaag tggattgatg   660
tgatatctcc actgacgtaa gggatgacgc acaatcccac tatccttcgc aagacccttc   720
ctctatataa ggaagttcat ttcatttgga gaggaccctc aacacaacat atacaaaaca   780
aacgaatctc aagcaatcaa gcattctact tctattgcag caatttaaat catttctttt   840
aaagcaaaag caattttctg aaaattttca ccatttacga acgatagctc tagaatgaga   900
ccatttgctg ctcttttcct tgtgcttttc cttgtgttgg ctacagaaat agggcccagg   960
gtggtagaag caagaatgtg ctcaagtcca agtcataggt tcaagggcat ttgcacttct  1020
tcgagaaatt gtgaaaacac ttgcaacagc gaacgattt caggtggtga gtgtaaaggc   1080
tttcgcagaa gatgtatgtg cacgggaccc tgtgtgtaat agggtaccta gtttctgcgt  1140
gtctttgctt ccgcttttta tgcttattgt aatatatatg aatagctatt tacagtggga  1200
cttggtcttg tgttgaatag tatcttatat gttttaatat gtcttattag tctcattact  1260
taggcgaacg acaaagtgag gttacctcgg tctaactctc ctatgtagtg cgagacccgg  1320
ggtccgcaaa aatcaccagt ctctctctac aaatctatct ctctctatttt ttctccagaa  1380
taatgtgtga gtagttccca gataagggaa ttagggttct tatagggttt cgctcatgtg  1440
ttgagcatat aagaaaccct tagtatgtat ttgtatttgt aaaatacttc tatcaataaa  1500
atttctaatt cctaaaacca aaatccagtg a                                  1531
```

<210> SEQ ID NO 72
<211> LENGTH: 1579
<212> TYPE: DNA
<213> ORGANISM: Artificial Sequence
<220> FEATURE:
<223> OTHER INFORMATION: Chimeric nucleic acid encoding Def6
<220> FEATURE:
<221> NAME/KEY: promoter
<222> LOCATION: (1)..(754)

```
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1170)
<223> OTHER INFORMATION: mat_peptide: Def6 peptide
<220> FEATURE:
<221> NAME/KEY: misc_feature
<222> LOCATION: (1171)..(1176)
<223> OTHER INFORMATION: Restriction site for KpnI
<220> FEATURE:
<221> NAME/KEY: 3'UTR
<222> LOCATION: (1177)..(1363)
<223> OTHER INFORMATION: TEV 3' UTR
<220> FEATURE:
<221> NAME/KEY: misc_feature
<222> LOCATION: (1364)..(1369)
<223> OTHER INFORMATION: Restriction site for SmaI
<220> FEATURE:
<221> NAME/KEY: terminator
<222> LOCATION: (1388)..(1579)
<223> OTHER INFORMATION: 5ST

<400> SEQUENCE: 72
```

| | | | |
|---|---|---|---|
| cctgcaggtc aacatggtgg agcacgacac acttgtctac tccaaaaata tcaaagatac | 60 |
| agtctcagaa gaccaaaggg caattgagac ttttcaacaa agggtaatat ccggaaacct | 120 |
| cctcggattc cattgcccag ctatctgtca ctttattgtg aagatagtgg aaaaggaagg | 180 |
| tggctcctac aaatgccatc attgcgataa aggaaaggcc atcgttgaag atgcctctgc | 240 |
| cgacagtggt cccaaagatg accccccacc cacgaggagc atcgtggaaa agaagacgt | 300 |
| tccaaccacg tcttcaaagc aagtggattg atgtgataac atggtggagc acgacacact | 360 |
| tgtctactcc aaaaatatca agatacagt ctcagaagac caaagggcaa ttgagacttt | 420 |
| tcaacaaagg gtaatatccg gaaacctcct cggattccat tgcccagcta tctgtcactt | 480 |
| tattgtgaag atagtggaaa aggaaggtgg ctcctacaaa tgccatcatt gcgataaagg | 540 |
| aaaggccatc gttgaagatg cctctgccga cagtggtccc aaagatggac ccccacccac | 600 |
| gaggagcatc gtggaaaaag aagacgttcc aaccacgtct tcaaagcaag tggattgatg | 660 |
| tgatatctcc actgacgtaa gggatgacgc acaatcccac tatccttcgc aagacccttc | 720 |
| ctctatataa ggaagttcat ttcatttgga gggaccctc aacacaacat atacaaaaca | 780 |
| aacgaatctc aagcaatcaa gcattctact tctattgcag caatttaaat catttctttt | 840 |
| aaagcaaaag caattttctg aaaattttca ccatttacga acgatagctc tagaatggag | 900 |
| aggtcttcac gtgtgttttc agtggttctc cttatgttgg ttcttgtgtt gagtacagat | 960 |
| atgtacacag accctgtagc agttcttagt tatgaaattg ggactaaggt ggcagaagct | 1020 |
| cgcatttgtg aatcggcaag ttacaggttc aagggaatat gtgtgtcaag gtcaaactgc | 1080 |
| gctaacgttt gcaaaaatga gggtttccca ggtggtcgtt gccggggatt tagaaggcgg | 1140 |
| tgcctttgct acaaacattg cgggtagtaa ggtacctagt ttctgcgtgt ctttgctttc | 1200 |
| cgcttttatg cttattgtaa tatatatgaa tagctattta cagtgggact tggtcttgtg | 1260 |
| ttgaatagta tcttatatgt tttaatatgt cttattagtc tcattactta ggcgaacgac | 1320 |
| aaagtgaggt tacctcggtc taactctcct atgtagtgcg agacccgggg tccgcaaaaa | 1380 |
| tcaccagtct ctctctacaa atctatctct ctctattttt ctccagaata atgtgtgagt | 1440 |

```
agttcccaga taagggaatt agggttctta tagggtttcg ctcatgtgtt gagcatataa    1500 gaaacccCtta gtatgtattt gtatttgtaa aatacttcta tcaataaaat ttctaattcc    1560
taaaaccaaa atccagtga                                                  1579
```

<210> SEQ ID NO 73
<211> LENGTH: 1531
<212> TYPE: DNA
<213> ORGANISM: Artificial Sequence
<220> FEATURE:
<223> OTHER INFORMATION: Chimeric nucleic acid encoding Def7
<220> FEATURE:
<221> NAME/KEY: promoter
<222> LOCATION: (1)..(754)
<223> OTHER INFORMATION: 35SP
<220> FEATURE:
<221> NAME/KEY: 5'UTR
<222> LOCATION: (758)..(888)
<223> OTHER INFORMATION: TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1122)
<223> OTHER INFORMATION: mat_peptide: Def7 peptide
<220> FEATURE:
<221> NAME/KEY: misc_feature
<222> LOCATION: (1123)..(1128)
<223> OTHER INFORMATION: Restriction site for KpnI
<220> FEATURE:
<221> NAME/KEY: 3'UTR
<222> LOCATION: (1129)..(1315)
<223> OTHER INFORMATION: TEV 3' UTR
<220> FEATURE:
<221> NAME/KEY: misc_feature
<222> LOCATION: (1316)..(1321)
<223> OTHER INFORMATION: Restriction site for SmaI
<220> FEATURE:
<221> NAME/KEY: terminator
<222> LOCATION: (1340)..(1531)
<223> OTHER INFORMATION: 35ST

<400> SEQUENCE: 73

```
cctgcaggtc aacatggtgg agcacgacac acttgtctac tccaaaaata tcaaagatac     60
agtctcagaa gaccaaaggg caattgagac ttttcaacaa agggtaatat ccggaaacct    120
cctcggattc cattgcccag ctatctgtca ctttattgtg aagatagtgg aaaaggaagg    180
tggctcctac aaatgccatc attgcgataa aggaaaggcc atcgttgaag atgcctctgc    240
cgacagtggt cccaaagatg accccacc cacgaggagc atcgtggaaa agaagacgt     300 tccaaccacg tcttcaaagc aagtggattg atgtgataac atggtggagc acgacacact    360
tgtctactcc aaaaatatca agatacagt ctcagaagac caaagggcaa ttgagacttt    420
tcaacaaagg gtaatatccg gaaacctcct cggattccat gcccagcta tctgtcactt    480 tattgtgaag atagtggaaa aggaaggtgg ctcctacaaa tgccatcatt gcgataaagg    540
aaaggccatc gttgaagatg cctctgccga cagtggtccc aaagatggac ccccacccac    600
gaggagcatc gtggaaaaag aagacgttcc aaccacgtct tcaaagcaag tggattgatg    660
tgatatctcc actgacgtaa gggatgacgc acaatcccac tatccttcgc aagaccctc    720 ctctatataa ggaagttcat ttcatttgga gaggaccctc aacacaacat atacaaaaca    780
aacgaatctc aagcaatcaa gcattctact tctattgcag caatttaaat catttctttt    840
aaagcaaaag caattttctg aaaattttca ccatttacga acgatagctc tagaatgaag    900
```

```
ccttttgtag cttttgttct ggctttcatg cttgttctcg ccatagagat gggtccccgg    960
gtcgctgagg cacgatgtg cacaaatccg agcagaacat tcaggggtcc ctgcgttagc   1020
gacaggaact gcgaatcctc atgcatggga gagggatttc cgggtggtag ttgccatgga   1080
tttagaagaa aatgcgtttg cagcaagcct tgtgcttagt aaggtaccta gtttctgcgt   1140
gtctttgctt tccgctttta tgcttattgt aatatatatg aatagctatt tacagtggga   1200
cttggtcttg tgttgaatag tatcttatat gttttaatat gtcttattag tctcattact   1260
taggcgaacg acaaagtgag gttacctcgg tctaactctc ctatgtagtg cgagacccgg   1320
ggtccgcaaa aatcaccagt ctctctctac aaatctatct ctctctattt ttctccagaa   1380
taatgtgtga gtagttccca gataagggaa ttagggttct tatagggttt cgctcatgtg   1440
ttgagcatat aagaaaccct tagtatgtat ttgtatttgt aaaatacttc tatcaataaa   1500
atttctaatt cctaaaacca aaatccagtg a                                  1531

<210> SEQ ID NO 74
<211> LENGTH: 754
<212> TYPE: DNA
<213> ORGANISM: Cauliflower mosaic virus
<220> FEATURE:
<221> NAME/KEY: promoter
<222> LOCATION: (1)..(754)
<223> OTHER INFORMATION: CaMV 35S promoter

<400> SEQUENCE: 74
cctgcaggtc aacatggtgg agcacgacac acttgtctac tccaaaaata tcaaagatac     60
agtctcagaa gaccaaaggg caattgagac ttttcaacaa agggtaatat ccggaaacct    120
cctcggattc cattgcccag ctatctgtca ctttattgtg aagatagtgg aaaaggaagg    180
tggctcctac aaatgccatc attgcgataa aggaaaggcc atcgttgaag atgcctctgc    240
cgacagtggt cccaaagatg gacccccacc cacgaggagc atcgtggaaa aagaagacgt    300
tccaaccacg tcttcaaagc aagtggattg atgtgataac atggtggagc acgacacact    360
tgtctactcc aaaaatatca agatacagt ctcagaagac caaagggcaa ttgagacttt    420
tcaacaaagg gtaatatccg gaaacctcct cggattccat gcccagcta tctgtcactt    480 tattgtgaag atagtggaaa aggaaggtgg ctcctacaaa tgccatcatt gcgataaagg    540
aaaggccatc gttgaagatg cctctgccga cagtggtccc aaagatggac ccccacccac    600
gaggagcatc gtggaaaaag aagacgttcc aaccacgtct tcaaagcaag tggattgatg    660
tgatatctcc actgacgtaa gggatgacgc acaatcccac tatccttcgc aagacccttc    720
ctctatataa ggaagttcat ttcatttgga gagg                                754

<210> SEQ ID NO 75
<211> LENGTH: 131
<212> TYPE: DNA
<213> ORGANISM: Tobacco etch virus
<220> FEATURE:
<221> NAME/KEY: enhancer
<222> LOCATION: (1)..(131)
<223> OTHER INFORMATION: TEV 5'UTR translational enhancer

<400> SEQUENCE: 75
ctcaacacaa catatacaaa acaaacgaat ctcaagcaat caagcattct acttctattg     60
cagcaattta aatcatttct tttaaagcaa aagcaatttt ctgaaaattt tcaccattta    120
cgaacgatag c                                                         131
```

```
<210> SEQ ID NO 76
<211> LENGTH: 187
<212> TYPE: DNA
<213> ORGANISM: Tobacco etch virus
<220> FEATURE:
<221> NAME/KEY: enhancer
<222> LOCATION: (1)..(187)
<223> OTHER INFORMATION: TEV 3'UTR translational enhancer

<400> SEQUENCE: 76
tagtttctgc gtgtctttgc tttccgcttt tatgcttatt gtaatatata tgaatagcta      60
tttacagtgg gacttggtct tgtgttgaat agtatcttat atgttttaat atgtcttatt     120
agtctcatta cttaggcgaa cgacaaagtg aggttacctc ggtctaactc tcctatgtag     180
tgcgaga                                                                187

<210> SEQ ID NO 77
<211> LENGTH: 192
<212> TYPE: DNA
<213> ORGANISM: Cauliflower mosaic virus
<220> FEATURE:
<221> NAME/KEY: terminator
<222> LOCATION: (1)..(192)
<223> OTHER INFORMATION: CaMV 35S terminator

<400> SEQUENCE: 77
tctctctcta caaatctatc tctctctatt tttctccaga ataatgtgtg agtagttccc      60
agataaggga attagggttc ttatagggtt tcgctcatgt gttgagcata taagaaaccc     120
ttagtatgta tttgtatttg taaaatactt ctatcaataa aatttctaat tcctaaaacc     180
aaaatccagt ga                                                         192

<210> SEQ ID NO 78
<211> LENGTH: 1682
<212> TYPE: DNA
<213> ORGANISM: Arabidopsis thaliana
<220> FEATURE:
<221> NAME/KEY: promoter
<222> LOCATION: (1)..(1682)
<223> OTHER INFORMATION: PHT4;6 promoter

<400> SEQUENCE: 78
caaagatgga aattctaaaa accactccct gcaatttctt atgtttcgtt tttagctcta      60 tattttccg ttttgtattt agtatttagg gtttaaggtt tgcttttttaa atgtttgatc     120 tatgagttat caaatggttg tttgatctta tgaatataag ttataagtag taaaaaaaaa     180
atttagctgt tttatctatg aatttaattc aattatgtt tagtacgtaa tctataaatt     240
tgactcaatt tatgtgcctt acactagtct aaaaataaaa gaattaccca caaatcaaaa     300
aaaattaagc taattagatc aaaattatga ttaagtaagt gattagaaaa gataacatta     360
taatctcaac atcaaggtgc tgtggtgtag tggttatcac gtttgcctta cacgcaaaag     420
gtctccagtt cgatcctggg cagcaccata ttttttata cctattcccc tcttttttc      480 acccgttaat taataaaata agaaatggcc gttacgtgat ttatctcacg gacataaaaa     540
tatcagcatc gtcgtcgttg accctaaaaa gcgatctcca tcatcttctt ttgtttcttc     600
taaattcttt cacaaaccct aaaattctcc tccgtcactg tcgacgacca ctgcgtttca     660
cactactctc tctctcgctc tctccaccgt taaacttcaa tacccatttg tcatttcccc     720
caaatctctc cgattcctta aatctaatt ggatttactt tgcctgtaaa accattcgca     780
ttgttacgca tccgattttg cagttcgaaa ctcgagttca acttcaattt gaggtagatt     840
```

```
tcgagaaaaa gctgaagaat tcggaacaa ctaaggtaaa gctttgtgat tttgacttcg      900
gttttcgatt tacattgtga agactgaaga agagatatag gcaacacatt ccactgtgta      960
attcggctgc ttgatgctta attttaagat ttcttcttgg gttctcgttt ctttggtact     1020
taagtttaat tgaaagaaag cttggatttt ttgcgtctgt aaaacgaaat tgagtctctg     1080
tgataacatt ggaatcgtaa ttcattagga attaggattg ttgatccttc aatttagaac     1140
caatatgatt acgttatggc ttttgggaca aattcatttg cttgatacga acttttactt     1200
cagatttatt cttatttttt aagatctgtt tatctttatc ttttgatgtc atatttagga     1260
tatgttctta tcttctgtgt tgaaggattt gacttaattt tactttctag atgccttctt     1320
gtatgattgg agaagcgtaa gattgtgtat ttttaggatg cctaattgaa aatggataaa     1380
gttgtgttac ttatacctct ctcatatata tctcaacaga ggaacgtatt gggtttgagt     1440
ctattttgtt aatgatcaga ggagaattca tcagtcatat agaatcgtcc ctgcaagttt     1500
tgtgttaaca tgtatcacaa taagcaaatt aaactgcttt gaatatgtca ttgcagattt     1560
taacggtgga attggggagt cttgaagctt attttcctc ctggtctctt ttttcttatg     1620
tggtggtgct tgagagggtt tttgtatgat ataaatgctc tagatcagag aaaaggtcta     1680
ac                                                                   1682
```

<210> SEQ ID NO 79
<211> LENGTH: 1000
<212> TYPE: DNA
<213> ORGANISM: Arabidopsis thaliana
<220> FEATURE:
<221> NAME/KEY: promoter
<222> LOCATION: (1)..(1000)
<223> OTHER INFORMATION: PHT4;2 promoter

<400> SEQUENCE: 79

```
atatcttgag aaacacgagc aatttctcat aaatgcctaa tagtttagcc gtttaggcat       60
ctcatgatct cactgtaaac tattaggata gttacacata cacttaaata atagttacac      120
atacatctaa tattttgaaa atcctttata ttctatgaat tatccacacc aaatgacatc      180
atgtgtgact gtataaatac gactacaaat ctatgtaacc tataccaatt acaaatatgt      240
ttttctatgt ttaatagcta taccgtttgt gtgtgatata tatgattagt tacattaaga      300
tactttaaca caattctaga tttctagtgc aatgcagtta tcaaatactt ctgattttga      360
attgacaaag cgacttaaaa acgattgatt gtaaacaac ttaccacatg gcaagcacac      420
tcctaaacgc atcgaacaaa tccataaact gcatcataca taacaaat ccaatggctt      480
tgtcattagg atcactaccg tagcaccagt tggggcatag tgaaatacaa atgcctttt      540
cttatgtcat tgtcttaaac agacatgacc atctctctaa tttacgacta ctttttcctt      600
tttgggcttt gaatgaatca cgctttcaaa taattgggct gcttctttct ttcccatttt      660
agaccaattt caaagacaaa aaataaaact agcaattgct aaccgaaact ccggtatccc      720
ggttaacccg ttgtaggtgg ggctgacgtg ggtgcaatca ctttgtcata tcaacacatc      780
acgtgtctcc acgtaggatg cagcagaaac tatttactac attgactaaa ataccttca      840
ccaccaaaca ccaccagcac acgaaacttt catcgttttc tttcatggcg gattcgctct      900
ctcgctgaaa ctctctctct ctctcgttac tccaaccact cctaattatt cacatcatta      960
ttggcatgaa aagttaatct ttcctatata acaattatta                          1000
```

<210> SEQ ID NO 80
<211> LENGTH: 2418

```
<212> TYPE: DNA
<213> ORGANISM: Arabidopsis thaliana
<220> FEATURE:
<221> NAME/KEY: promoter
<222> LOCATION: (1)..(2418)
<223> OTHER INFORMATION: TPS-Cin promoter

<400> SEQUENCE: 80
tcatggcaca tcgaggagaa actgtttcct tgtggtaatc ctttataatc tctgttgcta      60
ggaggagatt tttcattaat agtctatctt cacaaaggc agattgattt gaagagatga     120
acttgggaag aatgattttg agtctgtttg caagaatctt cgatatcacc ttatagagaa     180
cattacagca tgatatcggt ctatagtcct tcatcatcac agcttctttt ctcttgggta     240
tcaaggccaa aatagtggag tttactcctt tgggtaggaa gcctgtctta aaaaaagatt     300
ggatggctac cacaaaatcg tttcctacta tcgaccatgt ctcgttaaag aactcacaag     360
tatatccgtc agggcctggg gatttatttg aaggcattga aagagaact  ttccgcacct     420 cctctgcagt gacttctagt gtgagcttgt cttgtcattc tcatcacatc tataatccag     480 tagagttttcc agttcctccc gcgaccaatc cacgtagtct ggcggtttga gcgttaaaaa     540
gtctctgaag tatcgaactg cctctgcttt tatttgctgc tgatttgatg caatatgtcc     600
atcatcacac ttaatctctc taacattgtt acgaacctcc cgaatctttg cagcattgta     660 gaaagttta ttattttggt ctcctatctt catccaatgc agttttgctt tttgcctaag     720
gtagctttcc tcaatacccg acagccttaa ccacttctca tatgcgtccg cttcagctac     780
cactgcctgt gaagatggcc ttgtcatagt ttctgcttgc ttttcacata aagttttata     840
ggcttctttt gctttttttg agatatcacc aagtaactgc ttccccatct ttctgaaatg     900
tggcttcaga cctttaaatt ttttgataa gcggtgcatg gctgaggtag aatgaaagag     960
aggctgagtt gtcttccaaa gctcttctgt ctcacttctg aaatccgaat acgaaattaa    1020
agcatttata aatttaaaag gcctcttgac tcgttgttcc tgctccataa tatagaatcg    1080
acatcttagg tgatctgaac aaccgcctga ttcaaagacg ctgtaggact gttcatacta    1140
ttgcatccat tgcttgctaa tcagtaccct atccagcttc ttacatatta ctccttcctt    1200
tctcttgtta caccatgtgt atctctggcc ttggtagctc atatctgtta attcacaatg    1260
tctgattaag tcttgaaaat ctctcatccc ttggagaacg aatggagatg attcatagag    1320
tgaatggtcc tctccttcta atatctcatt aaagtctcca catattaacc aagctttgtt    1380
atagaacaaa ggggaatcat gatgatattt aatatcactc cacaaatcct ttctttctgc    1440
tgcaaaattt gatgcataaa caaacgacac aaagaactct tcttgtcttc cttctaataa    1500
gacagagcaa gtgatgagtt gtgacgtctt atatattgga gatacacgca cgttatcttc    1560 tattatctttt caatagtaat ttgatataaa ttaagataat gtgcagtgaa cgagtggcga    1620
ttgttaagcc aagtgaacat tatatacttt attttatact ttctccaagc ttcgaatgga    1680
gaatttattt ccatacgact aactctacct aaaagggcca tgtttgtttg ccaacataac    1740
acgacgatca cgagatacac ataacattta gaatttggag aagatacatt ttgtttgact    1800 tcacttttg tgcgaatggc tgttctacct gaagggggcca ttagtataat ttttttgtac    1860
ataataacgt caccaaatat aacacgagaa tcacgaggta cacaaatcat ttaggcttgg    1920
acattatcta atcaaataag ctatgatatc aaatttacat acatatagtg gcctcgtggg    1980
tataattaca caaggagctt ttggagaaaa agaagtgtgt gatttaaatg acaattatac    2040
aaatgtgtac aattatcaga tccaaagttc atgtttaaa tcatcaaaaa aataataatt    2100
```

```
gatgagttaa atgatatttt tttcatttag atttagttag attagttgta cggttgtacc   2160
attatttaat aatttaaaag ttgaaatgat tataatgtat aaaagttgaa atatattgtaa  2220 cagatataga ttaagcattt ttgcggtcaa tatattataa aagcttttt  agctattaat   2280 tgaaaaatat tttacaccct tagatctttt gatctcctaa ttatataaaa tattttcttc   2340
taccgtttgt ctatataacc atatgtgttg tctagtgcat gtattcagcc acgaataaga   2400
gaatagtcta ctaaatca                                                 2418
```

<210> SEQ ID NO 81
<211> LENGTH: 2486
<212> TYPE: DNA
<213> ORGANISM: Spinacea oleracea
<220> FEATURE:
<221> NAME/KEY: misc_feature
<222> LOCATION: (1303)..(1483)
<223> OTHER INFORMATION: CDS of Def1 nucleotide
<220> FEATURE:
<221> NAME/KEY: 3'UTR
<222> LOCATION: (1487)..(1768)

<400> SEQUENCE: 81

```
actagtacta cctgttacta gagctgtcaa aacggttatt cgagttgggt ccgggtctga    60
tcatctcgag tctcgggtca tgaactggtc gggtcgggtc gggtcatttt atcaccgggt   120
gcaggtcggg ttcaggtcgg gttcagtcag gttgaaaatt tgtcgggtta tttttacatt   180
tcggtttagg tcgggttcgg ttcgggttcg ggtcgggtct ttttctagcc gggtacaatt   240
atgggttcgg ggcttaacga gtcgggtcaa gttcggatcg gataattacc gggtcggtta   300
taattcaggt cgggttaaga ccgggtacga tagctatcgg gattagtcaa gttttaacct   360
tataattaac ttttataaat ttggttaaat ttggtttagc gtttttcact tgttctagat   420
taggtaatta taaaaaaata tattaacttg atttaagtta ttatttagtt aggtcaatga   480
caaatcggat tgtcaacaag tcgcgaaaat tcaggtaacg gattgtcacg aattgagtca   540
ataacaggtt tcatggaatt ataattggtt tcgggtttac atcgggtcgg gtgttgaatc   600
aggttcgggt cattttttcgg tcgggtaagc tgactcagtt ttgttatcgg ttatatttcg   660
gtcgggtatc aggttcgggt tcgggtcttg cattaacggg tcgaaatcgg tcgtcggttt   720 taacggggttg gctacggtcg gattacgggt ttcctatttt aacaaaattt cggatctcgg   780
gttgggtccg ggtccttaaa aatacaggtc ggttcaggtc ggtttctcgg gtcgggtcag   840 ttttttgacag ctctacgtgt tacggagtat gttttaattt ttttaaaaat ggctacaaat   900 aattaaaatat caataattaa catgcatttt caatttgatg atttgggtat cataatagaa   960
acacagtatt atggttgaga cttgagatcg attaatcatg ggttgatagt ttgaattagt  1020
taaattttcg taattatttc attaatgtta agatctgatc cacgaaacat catattgtag  1080
ctaatgtccc aaattgataa aaagcagaat agcctaactc ctctgatctt gtaaagtgga  1140
ctatctaact aaatggccga ctaattcacc atcacaaatt aatgttctct aatattttt   1200 ccgaccgtaa ttaagtacgt agatttgaca caaattttgg tgaaacatat agtcttgttt  1260
aattttaaca aatttgttgt gaattgtgtc atttacagaa gaaatgggtc caagaaaggc  1320
agaagctgga attttttagct cgaggaaatg caaaactcca gtaaaacgt  tcaagggaat  1380 atgtactagg gactccaatt gtgacacttc ttgtaggtat gagggatatc cagctggaga  1440
ttgcaagggt attcgtagaa gatgcttatg ttgtacacat acttaaactc caaatatcaa  1500
tatcaacaaa ctcaatgtcg tgtacacctt tcgtcccaga ttagtagtca cgttagtttg  1560
```

-continued

| | |
|---|---|
| aactattaag ttagggagct agtacgtaca cacatatatc aatctatgtt gcttcgtgtt | 1620 |
| gtagccatga acgtatcttg ttatcgtgtt gttgttgttg tcgtcgtcgt cagacgtccg | 1680 |
| tcgttgatga attggtgaat tctagctagc ttctatgtaa aagtatcggc aattatacgt | 1740 |
| tgtccaagtt atggtgttgt aaaataaaag tgtttggatt atgaatgaag cctagctaac | 1800 |
| tttcaggttg accttgagcc tagtcttttg agtatcctac taattactcc ctccatcccc | 1860 |
| ggaatactcg caacgttttt cttataaagt cgtcccgaat ttctcacact gtttctgtaa | 1920 |
| atgttcattt tctttttgat attatactta ctcatggacc catgggcacg acacccacct | 1980 |
| atatccctac tccttaaaaa aaacattaaa aggtgtaaag atttgtttta tactctatca | 2040 |
| cgccccctca cataaaagcc cttggactt gaagtgtgga tgcaacatag gcctcctcat | 2100 |
| actcagcgcg aaatattcta ctttgaaatg aggggtggat gagatttgaa cccgtgacct | 2160 |
| ttgcgtcacg ctggctctga taccatgtca aatgaccaac tcaaccaaaa gcttaagctg | 2220 |
| gtggttgaag ccccaagagt agttttatac tatcactaca agaatttgtg tctttaacga | 2280 |
| caacctaatt acgacgggtc aaaaatcccg tcgcaaaagc cttttgcgac ggggctaaca | 2340 |
| accaaacaat gacgggaata accgtcgcaa atgtctttta cgacgggttt acgacaaatt | 2400 |
| tacgacggga tttctattaa cgacgacccc cttttatgac gggttcgcga caggaaaacc | 2460 |
| cgtcgttaat caacgattat tggcct | 2486 |

<210> SEQ ID NO 82
<211> LENGTH: 3767
<212> TYPE: DNA
<213> ORGANISM: Spinacea oleracea
<220> FEATURE:
<221> NAME/KEY: 5'UTR
<222> LOCATION: (1946)..(1999)
<220> FEATURE:
<221> NAME/KEY: misc_feature
<222> LOCATION: (2000)..(2060)
<223> OTHER INFORMATION: CDS of Def2 nucleotide
<220> FEATURE:
<221> NAME/KEY: Intron
<222> LOCATION: (2061)..(2579)
<220> FEATURE:
<221> NAME/KEY: misc_feature
<222> LOCATION: (2579)..(2764)
<223> OTHER INFORMATION: CDS of Def2 nucleotide
<220> FEATURE:
<221> NAME/KEY: 3'UTR
<222> LOCATION: (2767)..(3126)

<400> SEQUENCE: 82

| | |
|---|---|
| aaaatttacc tagctttcta gttttgaatt taactttcac gaaatttcat ttttttttaac | 60 |
| tcaaataatg ttaaccgaat ttgattagag tcgagtttgg ttctcaagca atagcggaga | 120 |
| caggggggcgg gtgaggcgtc caccccccca aaggaaaaaa aaagattaat atatatggta | 180 |
| ttaaatgtca ataaacattg tcaaacttgt cttgccccaa tgattgaatg atcaatattt | 240 |
| gacacaataa ccctatgatc aaatacctac attgacacat tatatacatt tcttttcttg | 300 |
| gcttttttt agttgatata aatttctcgc ccccaatctg aaatttctgg ctccaccacc | 360 |
| gttctcaagc caaatcaatt acgattattg atgggtcatg gattctacat ttatgaagca | 420 |
| aatatagcta gacttggaaa aacgaacccg gctatgaaaa tctgatccaa tttatccgac | 480 |
| ctgttaccta attttgataa gaaagacaa ctcaaaatca acccaaagtc taaattgacc | 540 |
| tgactcgtaa cctaaatcga catggaattg atttggtctg aaatgacccg atacatgaat | 600 |
| cgttcaaaat tgaattcatt atatcgatt tcactcgaaa taaaagtaaa ccgtactgaa | 660 |

```
ataactgtaa aatttgaatc aacctaactc taatccgaaa cgaagaacaa ctcaaattta    720
cccatagctt aaacaaaata acacaaagtt tcataactaa aacaatatta ttatacttgg    780
tatatttgcc catgtcttat gtacgtctca tcttctcgat catatatagt ctcaaagagt    840
gatagagtag tatagaagac tagaatcccc taaattaact tgtaaatatg tgaaaaatgt    900
aacccttgtc aataactacc ctaacatctt tatcataatc caataaactc gatcatatcg    960
tatatgctta accctatatt aattattttg taagaaatat tgtaacaatc aacaaattaa    1020
cctaattaat cccaaaattc gaataaatcc gatttatacc caacccgat ccaaagtaag     1080 aatgacataa aattatctga atcatgtcca taaaaaccca cttagtaggt ctaaacacat    1140
acagtgatac accatatgtt tttcttggtg tactagtcgg ttcaccttta gggcacgctt    1200
ggattgggtg taatggagta tagggtaat aaaagtcaaa ccaccataat aaaaggacaa     1260
tgaaggtgaa ttgaggtggt tgcaaggagg gtggtgtggt ggtattgtga tgagaagttg    1320
tggtagtggt ggtgttgtga ggagaaggga ggaaggggga agtacttacc ccccaaatga    1380
gggtaataat caccctagtg ggatggtggg taactattcc ctccatgatg agggtatttg    1440 ttcccctcc cctttttttt tttcttgcca cactagctt gtttcctttg ccaccacttc       1500
atcccctcat catcaccatc aattaccttca gtttgacttt tattacccct ttaataaatt    1560
accctcaatc caagcatgcc cttagggtta atccggattc ggagcgagtt ctgagtggat    1620 agatttttc cccctcccaa ttgtaggtga gggtgatcga acacagggtt ctccctacta     1680
aattcagccc caatcaccac tgaaccaaca gacaattagt gatacatcat atgttaatat    1740
gttatggcgc ggtatttcca gctagtgatc taaagaccac acaaggtatg tcggtaagaa    1800
atcatttcaa acacaagccc cgtcagaaag aagcccttta gcgtcaagac aaatgcaata    1860
gtgtcccata ttatttgggc atatacccctt gtcaatagtg aacattttct cctataaata   1920
atctatagtt tgtgttagtt ttgcataaca tatttacaat cttatacatt tatattcatc    1980
aataaattta aaagaaatt atgaagatgt caatgaggtc gattgctgtg gttttccttg      2040
tgtgcctact tgtcttgtca acaggttact aatgctatcc ttacttcctt accgtctttc    2100
aaatttttat tttggaaact ttcttatata accccatatt ttattttatt ttgatgtatg    2160
attaagagca ataaatagat aaagtttgct aatgctctgt ccatgaccat actatactaa    2220
tgttgttctt tttaaacgag accatacgta cttctagaca ttaatttcct taaattggaa    2280
tcgtttatgc tttgattta gacatatatc cctttaattt tacaacctaa ctttgatcta     2340
ataagtacgt aatatcgtac atgcatgtta ctattaagta ttgattactt ttgagtaggt    2400
cttctatgag accgccatat gcataagact gtttatgtca gctttaaagt gcacattgtt    2460
agttataagt agattacacc gtataatgtt ggcttaatca tgttttgtta gttttaatta    2520
gctaaaactc cggcaattaa attaacaaag ttgttcctaa atatgtgatt tgtttgcaga    2580
agaaatgggt ccaagaaagg cagacgctgg atttttcagc tcgaagaaat gcaaacacc     2640 aagtaaaaca ttcagggac cttgtgtaag gaacgccaac tgtgacactt cttgtaggta     2700
tgagggatat ccagctggag attgcaaggg tattcgtaga agatgtattt gttgtacaca    2760
tgcttaaacg aataaccctc aatgtcgtgt actctgcttg tccagaatta atagtcacgt    2820
tagtttgaac tattacgtta ctaaacctgg acgaagatag ggagtacgtg cgtgtgagtg    2880
tgtgactatc tatccagaat taatagtcac gttagtttga actattacgt tactaaacct    2940
ggacgaagat agggagtacg tgagtgtgag tgtgtgacta tctatctagc ttgctcggtc    3000
ttgtaaccgt ttcttgttat cgttttgttg ttgttgttgt tgttgttgtt ggacttgttg    3060
```

-continued

```
tgaatttcga cctctatgta atgtattggc aattgtacgt tgtccaagtt atggttgtaa      3120
aataaaagag tttgcatgaa cggagccttt caggacttga gcctaccgta cccctttaatg    3180 aatatcctac acatcatatg ttaaattaat attcttacta gtcaatttgt tatatttata    3240
cggagtacgt atatatacat tgacgattgt aaacttgtga taatgtgaat aatgtgatgt    3300
tatattgtaa actatataat gtgagtatat agttacgttg tcggagaatt aagtgcatca    3360
tatcacaatt cacaagttta cataaaaggt ttaatcaaac acatgatatg aatttagaac    3420
attctaaact catactacat atatcaaacc tagaatttgt gaaacaatca ccccttcaaa    3480
gagttctcac tgtaatttgg gtgaggcacg tactcacaaa aaaatagagg gagaaacgta    3540
catgatacac tacaagaaat tgtactatta acgacgggaa atcccgtcgc gaaaggccaa    3600
taatcgttga ttaacgacgg gatttgttgt cgtgagcccg tcataaaagg gggccgtcgt    3660
taatagaaat cccgtcgtaa atccgtcaaa aacccgtcgt aaaagacatt tgcgacggtt    3720
attcccgtca ttgtttggtt gttagccccg tcgcaaaagg cttttac                  3767
```

<210> SEQ ID NO 83
<211> LENGTH: 2854
<212> TYPE: DNA
<213> ORGANISM: Spinacea oleracea
<220> FEATURE:
<221> NAME/KEY: misc_feature
<222> LOCATION: (972)..(1024)
<223> OTHER INFORMATION: CDS of Def3 nucleotide
<220> FEATURE:
<221> NAME/KEY: Intron
<222> LOCATION: (1025)..(1681)
<220> FEATURE:
<221> NAME/KEY: misc_feature
<222> LOCATION: (1682)..(1851)
<223> OTHER INFORMATION: CDS of Def3 nucleotide
<220> FEATURE:
<221> NAME/KEY: 3'UTR
<222> LOCATION: (1854)..(2848)

<400> SEQUENCE: 83

```
aggaatagtt aaatcatgag gaaagtcaaa taaataatat caatattata aatttgtgta     60
aacatttatt ttacacgtaa gtcgtttaat attaataaat gtagattttt gtttaaactt    120
aattatgaag aatcatatca gatcagacca gaccagatca gaccagaaca gatcagatca    180
gaaaaaataa gttcagatca gatcagacca gatcagatca ggagaaataa ggtgaactaa    240
acagggcctt actccatttt tcacacacac atgaagaaa ataccaaaaa gaaaccacac    300
aagaaagaga gtttgataca cacttcatat atgagcaagt gcaaaaggta tgccaaaaaa    360
atccatatta ttttacact atttacataa tttatttgt ttatttttta tgattgatac    420
ttcaggaaaa acatattcat ttgggatctg gttagatctg tcttaatgaa tattttgcaa    480 atttttaaatt tttattattt ttaattatca ataattaaag ataataattg ttcaagttat    540
acgttaataa tcgtgaaaaa caagtgttg caattaaaaa gaaatgaagg aagtatgatg    600
caagggtgat agttaggtag atcacagtat ttaccacgtt cttgataaaa aaaatatttg    660
gtgaaaattt attagagttt ttcaattttt tatttttttgt gccgaacaat gaagtaggca    720
caactatttc ttagaagtaa attatttaga gttagaacaa ttataaggaa tagctacaat    780
tttaaattga tcatcacaaa tctttcatga caaatattcc ttcaaaaaag tcattaaaga    840
cggagatgat aatagtcgtc atcgtttagg tgacaaatta aaactacctt aaagtttttt    900
attactcgta gttcttcttc attctattga tcttctctct atattttaaa gtgcttaaac    960
```

```
atgaaacaaa caatgaagca ctttggggct atatttcttg tgttgttgct tgttctggcc    1020
acaggtataa caaaaatttc ttcccttttga attatacccca gtaaatagat ctcatttgta    1080
gcaaatttta ctttgtctcc ttacactaca aaaattgtac cattaacgac gggaaatccc    1140
gtcactaaag gccaataatc attgattaat gacgagattt tctgtcgcaa acccgtcata    1200
aaaggggggcg tcgttaatag aaaatcccgt cgtaaaccca tcgtaaaaga catttgcgac    1260
ggttgttccc gtctttgttt ggttgttagc cccgtcgcaa aagccttttta cgacaagatt    1320
tttgaaccgt cgtaattaga ttgtcgttaa aaatacaaat tcttatagta ttagaaaata    1380
cagagtaaat gaaaaaaata cccttattac taattcgcta tatatcgcta tcctctttac    1440
atctttatga attctaataa tactacttat tgagtatatc aaaataatat ggagtactat    1500
gtacgaagta tattattact actacttatt acggagtacg tacataaagt agtaataaaa    1560
tgacagttac ttgtaaaatg atgattgttt tgttaaaact ttttaataat ttttggatat    1620
ttattattga cctttgcttt taattttgtt gggatttaat tataccatga aaaatacaaa    1680
gaacatggag caagagtagc agaagcaaga acatgtgaaa ctccaagtca aaagttcaaa    1740
ggaatatgta ttagtgactc caattgtgaa tcaatttgca ataccgaagg atttcctaat    1800
ggagaatgta gtggccttcg cagaagatgc atttgcaaca caccatgcac ttaatgttta    1860
attatgctca taattaatta tgtttaatta ctaattgatg tgctttggaa tagaaatttc    1920
atattttatg tacgttatga attgaaatct atttgtttca gaatagctag taaaatctga    1980
aacattttc aatacacttt gtgtgttatg ttttaaaaaa aactatcgga taagacgcgt    2040
ttcagtctaa tcgggataat aatctctat acatatatag catgtaaaat tttggcgaca    2100
ttaatttatc tcagatttta ccaactcaaa atctgagtta tggagctctt tccaagtatt    2160
ctctccgttt tgaaataatg gttacccttg acttttaaca ctattcacaa atttcaattt    2220
gactatcatt tgttacttat gaataaggaa aaatatagcc gtgtgagatg ttgtttgatt    2280
tatttcgatg tgtactttg taatattaac ttttttataa ttttaacgat tacaaaatta    2340
gatgtattaa tcttcaacca tttacattga caagcataaa aagatgaagt gtaatcattc    2400
aatcgaaatg gaggagaaat tccgagttaa tatcagtgat tgtaaaaaat ttccaatcaa    2460
atggcatttt cgtaaacatt atgcccgaaa aatgtatatg gtataatgtt aagtgttgac    2520
tgtacatttg taggtattga ctgtatattt gtagttattg actgcatatt actcggtgtt    2580
gattgtatac cacttgtcgt tgatgtatat tttatgattg ctgatgaatt actaaaatac    2640
aatattgttt attggtaagt gattgactgt atatttgtag ttgtagattg tttattagta    2700
gaagcttatt gtatattgtg agctgttgac tgtatattat atagttgttg atgtgttatg    2760
aaaatacaat aatgaccgta catgtggtcc acatttgatg acatgtcact atactttaac    2820
ccacatttaa tggcattttc gtaataaaat catc                                 2854
```

<210> SEQ ID NO 84
<211> LENGTH: 3903
<212> TYPE: DNA
<213> ORGANISM: Spinacea oleracea
<220> FEATURE:
<221> NAME/KEY: misc_feature
<222> LOCATION: (56)..(224)
<223> OTHER INFORMATION: CDS of Def4 nucleotide
<220> FEATURE:
<221> NAME/KEY: 3'UTR
<222> LOCATION: (228)..(308)
<220> FEATURE:
<221> NAME/KEY: 5'UTR
<222> LOCATION: (2069)..(2145)

```
<220> FEATURE:
<221> NAME/KEY: misc_feature
<222> LOCATION: (2146)..(2197)
<223> OTHER INFORMATION: CDS of Def5 nucleotide
<220> FEATURE:
<221> NAME/KEY: Intron
<222> LOCATION: (2198)..(2730)
<220> FEATURE:
<221> NAME/KEY: misc_feature
<222> LOCATION: (2731)..(2900)
<223> OTHER INFORMATION: CDS of Def5 nucleotide
<220> FEATURE:
<221> NAME/KEY: 3'UTR
<222> LOCATION: (2904)..(3013)

<400> SEQUENCE: 84
tatttgtttc caattttcat gaatctaaca catttttttg tatatgggga gcagaggtaa      60
gtacaaaagt agcagaagca aggatatgtg ctagtccaag tcccacgttc aaaggaatat     120
gttttagcag caggaattgt gaaactaatt gcaattctgt gaaattttct ggaggaagtt     180
gtcaaggttt tcgtagaaga tgtatgtgca ccaagcctcg cgcttaatta accgatggtg     240
tgccacgtgc gcgttcctcg tcatcaataa tcagcttgac attggttaaa atttgcatta     300
aaaataaaag caatttgacg cacgtgttct ctttacatca tcttcattca tccacaatcg     360
agtggatgca gtatactatg tatatctata tataatctta tatacaaagt gtgtactaat     420
acttgtatta tagttgtggt aactttgcaa tatgcaaatt aagtagtagt actatgctac     480
actaataaat taatgaaagc tacaattcat taacaaagtt gaaagtatta tttacgttta     540
tctttaattt cgttttatta acaactactt cgtgcaaatt ttagatattt gaaaagtaca     600
agttaatacg aaatatgaga attgaatagt cttcattttt agggtataa aactcaatgc      660 gtggattatg gatatatgtg cacgatactc atgtactgcg taggaaatga acacaagtgt     720
acaacctaga ctatggacat atacacacaa atgcacacaa atgtacagcg tggaccatgg     780
acatcacgat gctcactgtg tagcaaatga atacaggtgt atagattgga atatggacat     840
atgtgtatga tactcattgt gttgcaaatt aaatgaacac aggtgtataa tccggactat     900
agacatagaa aatgaacaaa ggtgcataac aatactcatt gtttagcaaa agagcacaag     960
tgatgtcctc agttatggac atatgtgcac tatactcact atgatattat gacaaaagtg    1020
catcatatga attactttgt atattttttt aaaaaaaatc atataaaaaa aaatctcgtt    1080
tctatctact ataatcgcat gttctttttag ttacatatgc tacgtacatt tgtataccct    1140
cattgcgtaa taattattgt gcacaatatg tccataatct aatttgcggt aaaaaattat    1200
ccaccttcta acctttttaa gggaaaatta ccttcttatt ttgatcacat gtacattcaa    1260
attctttacc aaaggtaaat gggcccggta gcaccaatta gggatgaccc gggtgagaaa    1320
aaatgtcagg gtaccctgaa tcgaaattgg aacctgttag gaacctgagg tttcggaatc    1380
ggaacctgtt gtgcaggttc tggttccgga taacgaaatc gggaacctgt gcaacaggt     1440 tccggtttcg gttctcaatt tccggaatgg gtaccttgtt gggtacctgt acatatcaa     1500 ttctaatatg aattgaagta cccaaaataa gggaccggga caaataaaaa tgttttctat    1560
gtccaaaata taaacaatc caagctaatc tttggaacat ataaatatag aattacaatt     1620
taagcctaat ctataaaaca attaaagccc aaagcataaa gtacatattt tgtccaataa    1680
attatcaata ttttatttga agttttaaat gacagggtac cctgaattag aaccttagaa    1740
caggttccgg ttccggttct cattttcagg aacctgttac aacagtgttt cggtttcgat    1800
tccggttccc atttttagaa acctgttgca acaagttccg atatgattct gatttctgaa    1860
```

-continued

```
attttaacag ggtaccgtgt tgtgctcaac cctaccgcca attaattgac aatttatgag   1920
aaagtatttt ttcttcttta tcttttttaa ttggaaaaga aatagttttg atatgagcca   1980
cataaaaggg atgggtgatc acaattataa tattggaacc acaaatatct aatcctatat   2040
aagtaacctc tagtgttgtt atcttgctca ctcaccaaat acaacttcta caagttaatt   2100
tcactaaaca tcttcttaat taagagctta attatgaagc aatcaatgag gccttttgct   2160
gctcttttcc ttgtgctctt ccttgttttg gccacaggta catttttattc ctcttccttt   2220
ctaaaactta taacttataa tgtcattatt tttcgatcct tgtacgtcgt atgaagtatc   2280
aaattaaagt tcgaataata agaaaactaa tcacgtcttc tctataaatt ctaaattagt   2340
ttatatagtg tatgtcacat aattaaccac ttactttcat aaattttaa tgcttcttcg   2400
tttcttaata tctgcatcat tttgactttt cacactattc atttagaaat atgttttaag   2460
atgatgatcg aggattttca ctggccgtac tactactaga gacattggat ctatcaaacc   2520
ccgtctctta taaacaaac atgttgattt ccttgaccat ttacgatttt ttgttttttgt   2580
tttatgatgt gttaagatat gaaatttaaa catatactga gtatcttata gtatatcgag   2640
catatctttt gacatcttac cgtaacttag cagtatgtga cgtagttatc taactcgtta   2700
atattttctc cttgttatga ataaaaaaag agatagggcc aagagtagta gaagcaagaa   2760
tgtgttcatc accaagtcat aggttcaagg gaatttgtac tagcagcagg aattgtgaga   2820
acacttgcaa cagcgaacga ttttcaggtg gtgaatgtaa aggctttcgc agaagatgta   2880
tgtgcacggg accctgcgtt taattaatta acataattaa tgttaattaa gtgtgtgcaa   2940
tttccatcct taaccttgta gttgagaggt ggatatatca tatatgtatg gttattagtt   3000
gaacgataat aaaattgtag catctatatg tttgaatcac tcggttgtac cattgtacgg   3060
agtatgttac tttgttaatc accactaccc caatcgatta ctattaatga aatgatgcat   3120
gtacgtgttt tttgtttgaa gttcgattgg agttatataa agatttgtga tagaagtaat   3180
ttcgtaagaa cttgatttaa ctatcttatg tatttatgta gttatgttac gtctatgttt   3240
gaacgtaatg ttcttttttta acttattacg ttatttcgta tttcatatac tttaattta   3300
gcttgttcga tctagtcact gtaacattca cattttcaat gccagcactg atcaatgaaa   3360
ctttctcgca ttaactaatt aaacttgaac ccaacatcaa attcggacta cttgaaccca   3420
ccacttgccg cctccaccgt acccaatatg tattccacaa tcattccgac tacaaaaaaa   3480
accaacttgc tttgctactt ctgtttgaga gaaaagttaa gcatgcattt tatatcaaat   3540
caagttgtga tataaaccgg ttgcttaact tttcccttga aaataaaaag taacaaggaa   3600
aaatcaatct attactatat attaaaagag acaccaggaa tgacacgtgt caatttctgg   3660
tgcgattttt tccggtcaaa aattactttc ctaaaaaaag tgtatctgtt tgatttttagt   3720
tttattctct accttttttta tataaactat ttatgtatgg aaacaaaata tatttagttt   3780
ataaattatg gcaataatag atacgacgta ataataatta ttctaaattg gcaatatttt   3840
agtcaatcgc tatattagta atggaaaata tatcactcaa tattttggtc aaattaccat   3900
att                                                                3903
```

<210> SEQ ID NO 85
<211> LENGTH: 4294
<212> TYPE: DNA
<213> ORGANISM: Spinacea oleracea
<220> FEATURE:
<221> NAME/KEY: 5'UTR
<222> LOCATION: (1944)..(2000)
<220> FEATURE:

```
<221> NAME/KEY: misc_feature
<222> LOCATION: (2001)..(2064)
<223> OTHER INFORMATION: CDS of Def6 nucleotide
<220> FEATURE:
<221> NAME/KEY: Intron
<222> LOCATION: (2064)..(2653)
<220> FEATURE:
<221> NAME/KEY: misc_feature
<222> LOCATION: (2654)..(2689)
<223> OTHER INFORMATION: CDS of Def6 nucleotide
<220> FEATURE:
<221> NAME/KEY: Intron
<222> LOCATION: (2690)..(3121)
<220> FEATURE:
<221> NAME/KEY: misc_feature
<222> LOCATION: (3122)..(3291)
<223> OTHER INFORMATION: CDS of Def6 nucleotide
<220> FEATURE:
<221> NAME/KEY: 3'UTR
<222> LOCATION: (3294)..(4176)

<400> SEQUENCE: 85
```

| | | | | | |
|---|---|---|---|---|---|
| tgtgtgggc | tgataagatg | aacgcgttac | aattcttata | attttttgcat | atggtgtttt | 60 |
| caataccttc | catcatatgc | aagaagagtt | tctctttaaa | tacgacccca | ttttttgcttc | 120 |
| aactaggagc | tttcctatta | tatattcagg | acacctcttt | tatagaacca | caaagtattt | 180 |
| gacagttta | ttttgttccc | tctgttcttt | cactctatta | tcctttgttt | tagccaaaaa | 240 |
| gttattcttc | aacaagtttg | gactagagca | ggaatacaca | ttgcttcaac | caaatattag | 300 |
| ttggcccttg | ggatggcctg | ttagagtcta | tcctggtccc | caggtatgtt | acacacccgc | 360 |
| atttcattaa | cttctcttta | aacatgacca | gtatttgtgt | tagagtggaa | gaatgcatcc | 420 |
| attgcttaga | aaattattta | atctgcaatt | ctgcataaga | gatgtacgta | ctgtataaaa | 480 |
| gtactacgta | aatggtattg | atatgcttac | atattattga | ttagtgagtg | acttgaacat | 540 |
| gttgtacatg | gtgtgagtac | ttttgaattt | gtgagtacca | tctgaaatca | aaacaaatta | 600 |
| ctataaattg | tatcacgatt | atcattttgc | tagaaaggag | acatgttatg | aaagactggc | 660 |
| ctctcggacc | tttccatatt | tatcttgcag | agctgtagaa | tatgctaatt | gaaataatat | 720 |
| aggattccct | agtacattaa | atctactaag | atcgaaatgt | tctagtgttt | ttatctaagt | 780 |
| gaaggtctaa | tgtcatgcat | ttatttgtg | tttgtccgag | gatgggtatg | gatgacttca | 840 |
| agtctttcca | ccaagcaatg | ttgctgctga | tcagcgtggt | ggacgtgttg | gaacttgcaa | 900 |
| ccggctgtat | gaggtggtcc | taagattcaa | aggacgagta | ttggcaatgt | catgttgtta | 960 |
| agttataaga | cagtgaaact | cttatttgat | atgatagaaa | tgaaattgaa | tcatattatt | 1020 |
| tcagttgtta | aattagcatc | agcttttaaa | tggttgcttt | tattttttat | tacatgtact | 1080 |
| ttattaacta | aaaagagcta | tagaataaaa | aaagcccgac | gaaaaatata | gaatccgctt | 1140 |
| acaaatacca | tcgttttta | gtttaatgct | actaatttta | attcatactt | cgtattaaat | 1200 |
| tggttggtga | gtgcactaaa | gttttttgtca | ttacaagaga | tttgacaaca | cttatatatt | 1260 |
| aaatgctgct | aaatgtggca | acatcaacaa | cgcttattaa | aagcactatt | atttttttaa | 1320 |
| cagcgctagt | aattcacagc | ccttataaag | cgctatgttt | aaatgaaaaa | aacgttgtta | 1380 |
| aaagcttatt | gtggtgtagt | gtaaaaaagc | aaatcagtca | ctatctctct | ctagttcttt | 1440 |
| tcacttatct | aatttacgta | ttatatcgta | caaagatctc | tcagcacac | tctgtgatgg | 1500 |
| tctaccgatc | atataggtga | tcgactaaaa | ggagacaacg | gtcaaacacg | tcaacggtta | 1560 |
| aactaatccc | caaatatta | tctttgtagt | ttttcatgca | gaaacatatt | acaccgtaaa | 1620 |
| aaacattatg | aaacaaactt | aaaaaaaaaa | aaaaaaaag | taaacgtcca | ttataattcg | 1680 |

```
gaggtactaa tattctaata ttagaaagtg tatgtgaaca taagaacgtg taatatggca    1740
gccaacgcaa aagaaaacta cataatttga tctgagtcac tttagtgtgt tcatctatgc    1800
tttttctaga tcgatcttaa tttcttttc gtcagcagct ttttctagat ctatctttaa     1860
taaacataaa attaaaagaa attaaaaata aaaaggaaaa ataccaaagt ttcggctata    1920
taaagaagtg tgttgttggt agtgataatc gtgtgccaca aaatataatc ctcgtacttt    1980
gaaattaagg agtgaataaa atggagcgtt cttcacgtgt gttttcagtt gttcttctca    2040
tgcttgttct tgtgttgtcc acaggtttat gttctttctc gtaatttcat tttatttatt    2100
tccaattaaa tcattctgct caaatattta atttgtttgt tgcttttaat taattaatct    2160
cacgccctac taatcacaaa taatgaatac tttgcatata tcacttgctc ttatttgatt    2220
tatgcaaagt gataaaagtc aaaatttgcg acaaattatt tgttttgtaa ctatattttc    2280
caaatagatt aaaaatatat aatattatta gattgtaatt tttatttttt aatttacaag    2340
ataaaatgag taatatatat ggtttccttc tttttttatgg actacctat ttaaatatat    2400 attgtcgtag taaaagtata tcgatgactg taaaaataat ttgatgagtc ttgaactacc    2460
ttgtttaaat aaatattgta atagtcgtca tttacgaact ttatcatcac ccgtgcttta    2520
tttttaaaga acttgacttc atgattggcc atgaccaatt aagctaaaaa aactcataat    2580
taacttattt aaggggggc aacaaggtta gatgaatttg atgtttttt ttttcattc      2640 taaccattga tagatatgta cacagaccca gtggcggttc ttagtatgg tataaatggg     2700 ctggtgaaaa gttccataat ttatttctaa ttccaacccct aatattttaa atataattgt   2760
ataaattgca taatgtttct atagtccctc ctaaaactgt tcaaaatccg caacttcata    2820
gacagtaata agtttcttcg ttaatatgca taaagtactc cgatccacca tattaatatt    2880
gtttaatcat cctaaaatat tgaggttaca aatgacgtac tataacaagt tttcttagct    2940
aaaatacgtt gttattaaat gttatgctag aatatgtatt taatcggtta agtccccta    3000 ctgcaacctc ccaataccc caatacgaga tatctgcatg tgaacgtaac taacatattg     3060
tttatgaatc atgttaaatc tctgtattct ttattcatgt tcttaattgt ctttcttaca    3120
gagattggga caaggtggc ggaagcaagg atatgcgaat ctgcaagtta caggttcaag     3180
ggaatatgtg tgagcaggag caactgtgct aatgtttgca aaaatgaggg tttccccggt    3240
ggccgttgcc gcggtttccg tcgtcgttgc ctctgttaca aacattgcgg ttaattgtta    3300
tgccacggcc acttttcctat gtgctagtgc ttatgacatt gatctgaagt accttcttaa   3360
ttgacgtgtt cttattgttg ttttaagttc aaataatgtg taatcctgtt tcttttgcgt    3420
cgtaagttaa attgatctat gatctttaaa ttgtattccg tatgttggta ccttcttaat    3480
ggtttgtagt ttaattaaat tttactttca cgcgtaacta atttgaagat ttttgcacat    3540
ttacttgctt ttttgggtct atataatata gttcatctgt tccataacaa tgttctggta    3600 tattttttt ttacgtttgt caatgcacat tttatatcat tttcatatct aatataaatat    3660 taaaaattat aaaatttaat attattaaag taatcattaa gacaaatcga atcaaacatt     3720
gcgtgaatat gttttttctt atatattgga ttagaaagaa tttagaagtt ttgcatcaac    3780
tgtgaatagt gtcaaaaacc taaattgtaa catcattatg aaacgaagga gtatcaaatt    3840
atgctactcc gtctcaattt acttttcctt tttttatatc ctatgtactt tgcgccattt    3900
ccttttcgaa aattttctcc tctccacttt tttcttgagt taattctcac catccaccta    3960 ctcatttct tttctttagt ttttcattct cctaaaactc taccccgtga ttttagatca     4020
tttaaagttc aaaaataact ctacaaggta gagtttgagc aatatcaacc attgaatgaa    4080
```

```
aaatcaacag ctcatatatt atcttttcaa aatttcccta ttttttctca ttaatatcca    4140
cccttttatt ttcccctcct actcatttaa aataaaggtg attttatacc ttagattcaa    4200
ctccaaaccg gcaaactcca gactcttcaa taaaaatact agagtagttt tctactgact    4260
tttatcaaac tttaaaataa aattgaaatt gaat                                4294
```

```
<210> SEQ ID NO 86
<211> LENGTH: 4527
<212> TYPE: DNA
<213> ORGANISM: Spinacea oleracea
<220> FEATURE:
<221> NAME/KEY: 5'UTR
<222> LOCATION: (1914)..(2000)
<220> FEATURE:
<221> NAME/KEY: misc_feature
<222> LOCATION: (2001)..(2052)
<223> OTHER INFORMATION: CDS of Def7 nucleotide
<220> FEATURE:
<221> NAME/KEY: Intron
<222> LOCATION: (2053)..(3353)
<220> FEATURE:
<221> NAME/KEY: misc_feature
<222> LOCATION: (3354)..(3524)
<223> OTHER INFORMATION: CDS of Def7 nucleotide
<220> FEATURE:
<221> NAME/KEY: 3'UTR
<222> LOCATION: (3527)..(3661)

<400> SEQUENCE: 86
```

```
attttcattt tatattttgg taaatacttt gaagtagggt gataacgact atgtttcacg      60
gttaattttc ctttatactt cgtttgggct ttgacaacct cttttttttt tttttttttt     120
tggtgcgaat gagccacaaa ggcggggatg agaatcgatc ccatgatcac ctggaaccgg     180
aatgaaagct ctaaccaact gagctaccca ttactctttt tgacaaccta tattaattat     240
caagtgtggg gatgtaaacg agtcgaatca aggagtatat ttaaagtttg cctactgtct     300
caaacaaaaa aagtttgtct actgttgggc tagctgatgc aagtttaagc ccaacttgat     360
tcaccatttt ttcatacttc gtatgagcct ttcttaaatc ctaatagcaa taccctatat     420
tactacggag tactacgcat tatgatctag agttaatcgc attttagata attgatcatg     480
gtgtacaagg agctataatg caccctaaaa atataagtat aacttaaaga acatacctaa     540
cgtaaaataa acatgagttt taataaaaag tgaattaaca tattgcatgt tcttttgttg     600
taattttctt ttacatgtgt atatacttcc tccgtttcga aaatatcgca ctatgattga     660
cttttacttc tctaaccttt actttgactc ttaatatcac aaaccgtgtg caagtaaaaa     720
ttataaaaag aataatatta agaaaatata tatatcgata caaatctaat ataacccac     780 atgactaaaa ttttcttact tacgaattac aaaaaattgc caaaatcata gtgtaaatag    840
tgtaaaaaac aaatggtgcg acattttgg aacggatgaa gtatgttatt ttaggtgctc     900
accatactca ttatgtacca ttgttcatac ttagcccaca aattagagta aattttattt     960
taaaccaaat ttgaatagaa gttccgtata aggtacataa tatacgctaa ctatgtttgt    1020
cgatgaaagg cacggggtta cctaatatgt atgaccatgt gatcagtgat ggatcttgaa    1080
caattttaag aaaaaggaca gtagaaaaat taaacaatgt agcatgtatg caattttatac    1140 aataaaacac aaaattttgg gggagctgca actaaacctg gcaaatctga cccaaacccg    1200
aaaaactgac ccgattgatc tgatctgtaa cccgaaattg atctgaagcg acgacccaaa    1260
attaacctga aaactaaaca gaaccgaccc gaaaccgaaa ctgacccaga aatgatttga    1320
cctgaaatga ccagatatcc gaatgacccg aaccaaagta cccaaaaaga tcttcacccg    1380
```

-continued

```
aaaccgaata ttatttaaat ttttttatta taattttcat tttattaatt tatactgttt    1440
tgaattatag gaaaaagatt ttgttaatat tatgatagtg accaccaaat ctaaaaagaa    1500
acaacctaat caaaactaaa aatccaaaaa atttgatcca attaacccaa aaactcgatc    1560
taaccaaaaa aatctgatat aatccgaaaa ctcgatccga tatgaacgat ctgatacgaa    1620
ttgatcctat atgacccgat ccaatattga tccgaaatca tgacgagaac cagacccggc    1680
ccgattaaaa aaaccgaac tcacccaaaa gccgagaatt atgtttaaaa aggttgtacg     1740
aagtttaaat attaggaaaa agaacgtgtc acatttatag tcatggtgat tcatgagatc    1800
tgtaacatgt acgtgtagct tcatttaggc attggtattt gcaccaaagc accatttggc    1860
aattgccatg cacaccatct tcccttataa agtagctttt gtgtctgttt tcatcaccaa    1920
atcaaaacaa aacaaaaaaa acacaccata tattttccta attattattg aattttttt    1980 atcaaatagt tcaagttgca atgaagccct ttgtagcttt tgttcttgct ttcatgcttg    2040
tcttggccat aggtacaact tccttgacct tcctttgaat taagggtgtc tgtttcataa    2100
tatatgcctc attttaattg tcttcgtttt aattgtcttc gttagacgaa atgcttaaca    2160
taagtgctat tagtctagct agtactctgt actataagca taactataag cataatgtac    2220
ttcctccgag ttgattttta cactatttac atattaatta tactttaatt atactttgat   2280
aattgttggt gatttatacc taaggtaaaa catagtcgtg tgggatcttg ttaatttaat    2340
atgtctcgtt aaaatattaa cttttttata attttgtta atgagaaata aatatattaa     2400
tgatcaaagt tgttcattat gcatgaaagt gacaaacatt acagagtaaa aatgaacagt    2460
ggaagtatat cttagtcact tctagcaaaa ggtgatcaaa atttgggtct ggttgggttt    2520
taacacataa cacataaatc ataaatcatg cccaaaatca taaattttgt gctggttttg    2580
cgggccgaaa tggggttttt aaagcaggat tcgggttttg gtctaaaaat gcatatttta    2640
ggctatttaa atccacactt ttttgggccg gattgggtta gtggccgggc tatagttgac    2700
caagtctaat cttcaactta ttttaacgtg ggataaaataa tctttaattc acatgtgggt   2760
taatctttta acagatacgt agtactccct ccgtttctta ttgttgtatc cgttttcatt    2820
ttaagcgttt catattgttg tatccatta gaatctattc tattttgga catatatttt      2880 atcctaaaat acccttacat ttctatctaa ttaccaaaat acctaaagat tctacccata    2940
ttcccaccta attttcccca cccataatat ttaatttttt tccctactcc atatacccac    3000
tctctcacct cctttatcac ccatcattat cactcctctc tcttacctta tttctttatt    3060
attttcctac tcctttattt attataatct cttacaccta atcatttctc ttacactcaa    3120
tcattacact tatacccata caaatcaata tttcaatttt cttaaaaacc acagcagatt    3180
ccaaatggat acatcaaaaa gaaatggagg gagtacttcg tacatgatat tgaacgaggc    3240
cttagtgtct atgagatgtt ttagtttttcc atatatgttt ttgctaaatt tgataatttt    3300
aattttgcat gtctaatttg ttgatgatat ttgttgttgt gtttaaaatt aaagagatgg    3360
gtccaagagt agcagaagca agaatgtgca caaatccgag tagaacattc aggggaccat    3420
gcgttagtga ccggaactgc gaatcgtcgt gcatgggaga gggatttccc ggtggaagtt    3480
gtcatggctt tcgtagaaaa tgcgtctgca gcaagccttg tgcttagacg gccttccaat    3540
ttcatcttct tttatgtatt agtcttgtac cctcgtaatg gaggaggaaa caagccaggg    3600
ttataaacaa atgaaatgtg cacgctttat gtactttgtt tatttatgaa aaattaataa    3660
aatgtattat ctctgttctt tgaaagtttt ttttgacgtt ttcgaatttc ttagtaagaa    3720
```

-continued

```
aatcttgatc ataaattatc tctattatac tacctccatt tcacaatact tgtatcattt    3780
atttatttat tttcaagtat cccaacatgc ttctttgaac attaatatct ctcactgcgt    3840
ataagtaaaa attataaaaa attacggagt aatatttata atcctcacat taatacgaat    3900
ttaacaagat tttactagac tatgtttact tttacataat gtgaaagaac aattgtcaaa    3960
gttagttaat gaatagtgtc caagatgcat ctattgcgga acggaggaag tatatactag    4020
tcagaagcat gtgctatgca cgtattggct taacgtacat ttataaattt tttaaacttg    4080
catattgtaa tgcactaaac actaaggtct ttatagacca ttacaaatat taaactaaaa    4140
gtcgaattaa tatataatgc aagggtcctg tgctcgatct tcttgtaagt tttactattc    4200
gtacggagca ttaattaagt tgttttctac tatttataac ataaaagaca tttaatcaaa    4260
taaaagttta tcattcttat tcgcaagtta agaaatgtat acaccttgct ctattaaaaa    4320
tcgcatggag ttattcacat tttcaaaaaa aaatattata catgtacact ctctgttttt    4380
ttttaaatgc atcacttaaa atttcacatt gtttatattg acttagatat tttactaata    4440
tatacagagt aataatcaaa tgttattatg taaaatgttg tttcacaatg catattttct    4500
taatatcaac ttttataat atttacc                                         4527
```

<210> SEQ ID NO 87
<211> LENGTH: 53
<212> TYPE: PRT
<213> ORGANISM: Artificial Sequence
<220> FEATURE:
<223> OTHER INFORMATION: Consensus sequence of Def3, Def4, Def5, Def6,
      and Def7 peptide
<220> FEATURE:
<221> NAME/KEY: misc_feature
<222> LOCATION: (1)..(1)
<223> OTHER INFORMATION: Xaa is Arg or Lys
<220> FEATURE:
<221> NAME/KEY: misc_feature
<222> LOCATION: (3)..(3)
<223> OTHER INFORMATION: Xaa is Ala or Val
<220> FEATURE:
<221> NAME/KEY: misc_feature
<222> LOCATION: (7)..(7)
<223> OTHER INFORMATION: Xaa is Thr or Ile or Met
<220> FEATURE:
<221> NAME/KEY: misc_feature
<222> LOCATION: (9)..(9)
<223> OTHER INFORMATION: Xaa is Glu or Ser or Ala or Thr
<220> FEATURE:
<221> NAME/KEY: misc_feature
<222> LOCATION: (10)..(10)
<223> OTHER INFORMATION: Xaa is Thr or Ser or Asn
<220> FEATURE:
<221> NAME/KEY: misc_feature
<222> LOCATION: (11)..(11)
<223> OTHER INFORMATION: Xaa is Pro or Ala
<220> FEATURE:
<221> NAME/KEY: misc_feature
<222> LOCATION: (13)..(13)
<223> OTHER INFORMATION: Xaa is Gln or Pro or His or Tyr or Arg
<220> FEATURE:
<221> NAME/KEY: misc_feature
<222> LOCATION: (14)..(14)
<223> OTHER INFORMATION: Xaa is Lys or Thr or Arg
<220> FEATURE:
<221> NAME/KEY: misc_feature
<222> LOCATION: (16)..(16)
<223> OTHER INFORMATION: Xaa is Lys or Arg
<220> FEATURE:
<221> NAME/KEY: misc_feature
<222> LOCATION: (18)..(18)
<223> OTHER INFORMATION: Xaa is Ile or Pro
<220> FEATURE:
<221> NAME/KEY: misc_feature
<222> LOCATION: (20)..(20)

```
<223> OTHER INFORMATION: Xaa is Ile or Phe or Thr or Val
<220> FEATURE:
<221> NAME/KEY: misc_feature
<222> LOCATION: (22)..(22)
<223> OTHER INFORMATION: Xaa is Asp or Ser or Arg
<220> FEATURE:
<221> NAME/KEY: misc_feature
<222> LOCATION: (23)..(23)
<223> OTHER INFORMATION: Xaa is Ser or Arg
<220> FEATURE:
<221> NAME/KEY: misc_feature
<222> LOCATION: (26)..(26)
<223> OTHER INFORMATION: Xaa is Glu or Ala
<220> FEATURE:
<221> NAME/KEY: misc_feature
<222> LOCATION: (27)..(27)
<223> OTHER INFORMATION: Xaa is Ser or Thr or Asn
<220> FEATURE:
<221> NAME/KEY: misc_feature
<222> LOCATION: (28)..(28)
<223> OTHER INFORMATION: Xaa is Ile or Asn or Thr or Val or Ser
<220> FEATURE:
<221> NAME/KEY: misc_feature
<222> LOCATION: (30)..(30)
<223> OTHER INFORMATION: Xaa is Asn or Lys or Met
<220> FEATURE:
<221> NAME/KEY: misc_feature
<222> LOCATION: (31)..(31)
<223> OTHER INFORMATION: Xaa is Thr or Ser or Asn or Gly
<220> FEATURE:
<221> NAME/KEY: misc_feature
<222> LOCATION: (32)..(32)
<223> OTHER INFORMATION: Xaa is Glu or Val
<220> FEATURE:
<221> NAME/KEY: misc_feature
<222> LOCATION: (33)..(33)
<223> OTHER INFORMATION: Xaa is Gly or Lys or Arg
<220> FEATURE:
<221> NAME/KEY: misc_feature
<222> LOCATION: (35)..(35)
<223> OTHER INFORMATION: Xaa is Pro or Ser
<220> FEATURE:
<221> NAME/KEY: misc_feature
<222> LOCATION: (36)..(36)
<223> OTHER INFORMATION: Xaa is Asn or Gly
<220> FEATURE:
<221> NAME/KEY: misc_feature
<222> LOCATION: (38)..(38)
<223> OTHER INFORMATION: Xaa is Glu or Ser or Arg
<220> FEATURE:
<221> NAME/KEY: misc_feature
<222> LOCATION: (40)..(40)
<223> OTHER INFORMATION: Xaa is Ser or Gln or Lys or Arg or His
<220> FEATURE:
<221> NAME/KEY: misc_feature
<222> LOCATION: (42)..(42)
<223> OTHER INFORMATION: Xaa is Leu or Phe
<220> FEATURE:
<221> NAME/KEY: misc_feature
<222> LOCATION: (45)..(45)
<223> OTHER INFORMATION: Xaa is Arg or Lys
<220> FEATURE:
<221> NAME/KEY: misc_feature
<222> LOCATION: (47)..(47)
<223> OTHER INFORMATION: Xaa is Ile or Met or Leu or Val
<220> FEATURE:
<221> NAME/KEY: misc_feature
<222> LOCATION: (49)..(49)
<223> OTHER INFORMATION: Xaa is Asn or Thr or Tyr or Ser
<220> FEATURE:
<221> NAME/KEY: misc_feature
<222> LOCATION: (50)..(50)
<223> OTHER INFORMATION: Xaa is Thr or Lys or Gly
<220> FEATURE:
<221> NAME/KEY: misc_feature
<222> LOCATION: (51)..(51)
<223> OTHER INFORMATION: Xaa is Pro or His
<220> FEATURE:
<221> NAME/KEY: misc_feature
```

```
<222> LOCATION: (53)..(53)
<223> OTHER INFORMATION: Xaa is Thr or Ala or Val or Gly

<400> SEQUENCE: 87

Xaa Val Xaa Glu Ala Arg Xaa Cys Xaa Xaa Xaa Ser Xaa Xaa Phe Xaa
1               5                   10                  15

Gly Xaa Cys Xaa Ser Xaa Xaa Asn Cys Xaa Xaa Xaa Cys Xaa Xaa Xaa
            20                  25                  30

Xaa Phe Xaa Xaa Gly Xaa Cys Xaa Gly Xaa Arg Arg Xaa Cys Xaa Cys
        35                  40                  45

Xaa Xaa Xaa Cys Xaa
    50

<210> SEQ ID NO 88
<211> LENGTH: 53
<212> TYPE: PRT
<213> ORGANISM: Artificial Sequence
<220> FEATURE:
<223> OTHER INFORMATION: Consensus sequence of Def3, Def4, Def5, Def6,
      and Def7 peptide
<220> FEATURE:
<221> NAME/KEY: misc_feature
<222> LOCATION: (1)..(1)
<223> OTHER INFORMATION: Xaa is Arg or Lys
<220> FEATURE:
<221> NAME/KEY: misc_feature
<222> LOCATION: (7)..(7)
<223> OTHER INFORMATION: Xaa is Thr or Ile or Met
<220> FEATURE:
<221> NAME/KEY: misc_feature
<222> LOCATION: (9)..(9)
<223> OTHER INFORMATION: Xaa is Glu or Ser or Ala or Thr
<220> FEATURE:
<221> NAME/KEY: misc_feature
<222> LOCATION: (10)..(10)
<223> OTHER INFORMATION: Xaa is Thr or Ser or Asn
<220> FEATURE:
<221> NAME/KEY: misc_feature
<222> LOCATION: (13)..(13)
<223> OTHER INFORMATION: Xaa is Gln or Pro or His or Tyr or Arg
<220> FEATURE:
<221> NAME/KEY: misc_feature
<222> LOCATION: (14)..(14)
<223> OTHER INFORMATION: Xaa is Lys or Thr or Arg
<220> FEATURE:
<221> NAME/KEY: misc_feature
<222> LOCATION: (20)..(20)
<223> OTHER INFORMATION: Xaa is Ile or Phe or Thr or Val
<220> FEATURE:
<221> NAME/KEY: misc_feature
<222> LOCATION: (22)..(22)
<223> OTHER INFORMATION: Xaa is Asp or Ser or Arg
<220> FEATURE:
<221> NAME/KEY: misc_feature
<222> LOCATION: (23)..(23)
<223> OTHER INFORMATION: Xaa is Ser or Arg
<220> FEATURE:
<221> NAME/KEY: misc_feature
<222> LOCATION: (27)..(27)
<223> OTHER INFORMATION: Xaa is Ser or Thr or Asn
<220> FEATURE:
<221> NAME/KEY: misc_feature
<222> LOCATION: (28)..(28)
<223> OTHER INFORMATION: Xaa is Ile or Asn or Thr or Val or Ser
<220> FEATURE:
<221> NAME/KEY: misc_feature
<222> LOCATION: (30)..(30)
<223> OTHER INFORMATION: Xaa is Asn or Lys or Met
<220> FEATURE:
<221> NAME/KEY: misc_feature
<222> LOCATION: (31)..(31)
<223> OTHER INFORMATION: Xaa is Thr or Ser or Asn or Gly
<220> FEATURE:
<221> NAME/KEY: misc_feature
```

```
<222> LOCATION: (33)..(33)
<223> OTHER INFORMATION: Xaa is Gly or Lys or Arg
<220> FEATURE:
<221> NAME/KEY: misc_feature
<222> LOCATION: (35)..(35)
<223> OTHER INFORMATION: Xaa is Pro or Ser
<220> FEATURE:
<221> NAME/KEY: misc_feature
<222> LOCATION: (38)..(38)
<223> OTHER INFORMATION: Xaa is Glu or Ser or Arg
<220> FEATURE:
<221> NAME/KEY: misc_feature
<222> LOCATION: (40)..(40)
<223> OTHER INFORMATION: Xaa is Ser or Gln or Lys or Arg or His
<220> FEATURE:
<221> NAME/KEY: misc_feature
<222> LOCATION: (45)..(45)
<223> OTHER INFORMATION: Xaa is Arg or Lys
<220> FEATURE:
<221> NAME/KEY: misc_feature
<222> LOCATION: (47)..(47)
<223> OTHER INFORMATION: Xaa is Ile or Met or Leu or Val
<220> FEATURE:
<221> NAME/KEY: misc_feature
<222> LOCATION: (49)..(49)
<223> OTHER INFORMATION: Xaa is Asn or Thr or Tyr or Ser
<220> FEATURE:
<221> NAME/KEY: misc_feature
<222> LOCATION: (50)..(50)
<223> OTHER INFORMATION: Xaa is Thr or Lys or Gly
<220> FEATURE:
<221> NAME/KEY: misc_feature
<222> LOCATION: (53)..(53)
<223> OTHER INFORMATION: Xaa is Thr or Ala or Val or Gly

<400> SEQUENCE: 88

Xaa Val Ala Glu Ala Arg Xaa Cys Xaa Xaa Pro Ser Xaa Xaa Phe Lys
1               5                   10                  15

Gly Ile Cys Xaa Ser Xaa Xaa Asn Cys Glu Xaa Xaa Cys Xaa Xaa Glu
            20                  25                  30

Xaa Phe Xaa Gly Gly Xaa Cys Xaa Gly Phe Arg Arg Arg Cys Xaa Cys
        35                  40                  45

Xaa Xaa Pro Cys Xaa
    50

<210> SEQ ID NO 89
<211> LENGTH: 22
<212> TYPE: PRT
<213> ORGANISM: Spinacia oleracea
<220> FEATURE:
<221> NAME/KEY: mat_peptide
<222> LOCATION: (1)..(22)
<223> OTHER INFORMATION: Segura SoD1 peptide
<220> FEATURE:
<221> NAME/KEY: misc_feature
<222> LOCATION: (1)..(1)
<223> OTHER INFORMATION: Xaa is Arg, Lys, or Met
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 89

Xaa Thr Cys Glu Ser Pro Ser His Lys Phe Lys Gly Pro Cys Ala Thr
1               5                   10                  15

Asn Arg Asn Cys Glu Ser
            20
```

<210> SEQ ID NO 90
<211> LENGTH: 58
<212> TYPE: PRT
<213> ORGANISM: Spinacia oleracea
<220> FEATURE:
<221> NAME/KEY: mat_peptide
<222> LOCATION: (1)..(58)
<223> OTHER INFORMATION: Segura SoD2 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 90

Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Thr Ser Cys Arg Tyr Glu Gly Tyr Pro Ala Gly Asp Cys Lys Gly Ile
        35                  40                  45

Arg Arg Arg Cys Met Cys Ser Lys Pro Cys
    50                  55

<210> SEQ ID NO 91
<211> LENGTH: 25
<212> TYPE: PRT
<213> ORGANISM: Spinacia oleracea
<220> FEATURE:
<221> NAME/KEY: mat_peptide
<222> LOCATION: (1)..(25)
<223> OTHER INFORMATION: Segura SoD3 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 91

Gly Ile Phe Ser Ser Arg Lys Cys Lys Thr Val Ser Lys Thr Phe Arg
1               5                   10                  15

Gly Ile Cys Thr Arg Asn Ala Asn Cys
            20                  25

<210> SEQ ID NO 92
<211> LENGTH: 23
<212> TYPE: PRT
<213> ORGANISM: Spinacia oleracea
<220> FEATURE:
<221> NAME/KEY: mat_peptide
<222> LOCATION: (1)..(23)
<223> OTHER INFORMATION: Segura SoD4 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 92

Met Phe Phe Ser Ser Lys Lys Cys Lys Thr Val Ser Lys Thr Phe Arg
1               5                   10                  15

Gly Pro Cys Val Arg Asn Ala
            20

<210> SEQ ID NO 93
<211> LENGTH: 24
<212> TYPE: PRT
<213> ORGANISM: Spinacia oleracea
<220> FEATURE:
<221> NAME/KEY: mat_peptide
<222> LOCATION: (1)..(24)
<223> OTHER INFORMATION: Segura SoD5 peptide
<220> FEATURE:
<221> NAME/KEY: misc_feature
<222> LOCATION: (12)..(12)
<223> OTHER INFORMATION: Xaa is Ser or Ala
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 93

Met Phe Phe Ser Ser Lys Lys Cys Lys Thr Val Xaa Lys Thr Phe Arg
1               5                   10                  15

Gly Pro Cys Val Arg Asn Ala Asn
            20

<210> SEQ ID NO 94
<211> LENGTH: 24
<212> TYPE: PRT
<213> ORGANISM: Spinacia oleracea
<220> FEATURE:
<221> NAME/KEY: mat_peptide
<222> LOCATION: (1)..(24)
<223> OTHER INFORMATION: Segura SoD6 peptide
<220> FEATURE:
<221> NAME/KEY: misc_feature
<222> LOCATION: (8)..(8)
<223> OTHER INFORMATION: Xaa is any amino acid
<220> FEATURE:
<221> NAME/KEY: misc_feature
<222> LOCATION: (22)..(22)
<223> OTHER INFORMATION: Xaa is any amino acid
<220> FEATURE:
<221> NAME/KEY: misc_feature
<222> LOCATION: (23)..(23)
<223> OTHER INFORMATION: Xaa is any amino acid
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 94

Gly Ile Phe Ser Asn Met Tyr Xaa Arg Thr Pro Ala Gly Tyr Phe Arg
1               5                   10                  15

Gly Pro Xaa Gly Tyr Xaa Xaa Asn
            20

<210> SEQ ID NO 95
<211> LENGTH: 38
<212> TYPE: PRT
<213> ORGANISM: Spinacia oleracea
<220> FEATURE:
<221> NAME/KEY: mat_peptide
<222> LOCATION: (1)..(38)
<223> OTHER INFORMATION: Segura SoD7 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)

```
<303> JOURNAL: FEBS Letters
<304> VOLUME: 435
<306> PAGES: 159-162
<307> DATE: 1998-07-09

<400> SEQUENCE: 95

Gly Ile Phe Ser Ser Arg Lys Cys Lys Thr Pro Ser Lys Thr Phe Lys
1               5                   10                  15

Gly Tyr Cys Thr Arg Asp Ser Asn Cys Asp Thr Ser Cys Arg Tyr Glu
            20                  25                  30

Gly Tyr Pro Ala Gly Asp
        35

<210> SEQ ID NO 96
<211> LENGTH: 53
<212> TYPE: PRT
<213> ORGANISM: Raphanis sativus
<220> FEATURE:
<221> NAME/KEY: mat_peptide
<222> LOCATION: (1)..(53)
<223> OTHER INFORMATION: Rs-AFP2
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 96

Gly Lys Leu Cys Gln Arg Pro Ser Gly Thr Trp Ser Gly Val Cys Gly
1               5                   10                  15

Asn Asn Asn Ala Cys Lys Asn Gln Cys Ile Arg Lys Glu Lys Glu Lys
            20                  25                  30

Ala Arg His Gly Ser Cys Asn Tyr Val Phe Pro Ala His Lys Cys Ile
        35                  40                  45

Cys Tyr Phe Pro Cys
    50

<210> SEQ ID NO 97
<211> LENGTH: 51
<212> TYPE: PRT
<213> ORGANISM: Arabadopsis thaliana
<220> FEATURE:
<221> NAME/KEY: mat_peptide
<222> LOCATION: (1)..(51)
<223> OTHER INFORMATION: At-AFP1
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 97

Gln Lys Leu Cys Glu Arg Pro Ser Gly Thr Trp Ser Gly Val Cys Gly
1               5                   10                  15

Asn Ser Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50
```

```
<210> SEQ ID NO 98
<211> LENGTH: 54
<212> TYPE: PRT
<213> ORGANISM: potato
<220> FEATURE:
<221> NAME/KEY: mat_peptide
<222> LOCATION: (1)..(54)
<223> OTHER INFORMATION: Hs-AFP1
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 98

Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
                20                  25                  30

Phe Ala Tyr Gly Gly Ala Cys His Tyr Gln Phe Pro Ser Val Lys Cys
            35                  40                  45

Phe Cys Lys Arg Gln Cys
        50

<210> SEQ ID NO 99
<211> LENGTH: 50
<212> TYPE: PRT
<213> ORGANISM: Aesculus hippocasastanum
<220> FEATURE:
<221> NAME/KEY: mat_peptide
<222> LOCATION: (1)..(50)
<223> OTHER INFORMATION: Ah-Amp1
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 99

Leu Cys Asn Glu Arg Pro Ser Gln Thr Trp Ser Gly Asn Cys Gly Asn
1               5                   10                  15

Thr Ala His Cys Asp Lys Gln Cys Gln Asp Trp Glu Lys Ala Ser His
                20                  25                  30

Gly Ala Cys His Lys Arg Glu Asn His Trp Lys Cys Phe Cys Tyr Phe
            35                  40                  45

Asn Cys
    50

<210> SEQ ID NO 100
<211> LENGTH: 50
<212> TYPE: PRT
<213> ORGANISM: Dahlia merckii
<220> FEATURE:
<221> NAME/KEY: mat_peptide
<222> LOCATION: (1)..(50)
<223> OTHER INFORMATION: Ah-Amp1
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 100
```

```
Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
            20                  25                  30

Gly Ala Cys His Val Arg Asn Gly Lys His Met Cys Phe Cys Tyr Phe
        35                  40                  45

Asn Cys
    50

<210> SEQ ID NO 101
<211> LENGTH: 47
<212> TYPE: PRT
<213> ORGANISM: Solanum tuberosum
<220> FEATURE:
<221> NAME/KEY: mat_peptide
<222> LOCATION: (1)..(47)
<223> OTHER INFORMATION: St-PTH1
<300> PUBLICATION INFORMATION:
<301> AUTHORS: Segura, A., Moreno, M., Molina, A., &  Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 101

Arg His Cys Glu Ser Leu Ser His Arg Phe Lys Gly Pro Cys Thr Arg
1               5                   10                  15

Asp Ser Asn Cys Ala Ser Val Cys Glu Thr Glu Arg Phe Ser Gly Gly
            20                  25                  30

Asn Cys His Gly Phe Arg Arg Cys Phe Cys Thr Lys Pro Cys
        35                  40                  45

<210> SEQ ID NO 102
<211> LENGTH: 47
<212> TYPE: PRT
<213> ORGANISM: Sorghum bicolor
<220> FEATURE:
<221> NAME/KEY: mat_peptide
<222> LOCATION: (1)..(47)
<223> OTHER INFORMATION: Sialpha2
<300> PUBLICATION INFORMATION:
<301> AUTHORS: Segura, A., Moreno, M., Molina, A., &  Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 102

Arg Val Cys Met Lys Gly Ser Ala Gly Phe Lys Gly Leu Cys Met Arg
1               5                   10                  15

Asp Gln Asn Cys Ala Gln Val Cys Lys Gln Glu Gly Trp Gly Gly Gly
            20                  25                  30

Asn Cys Asp Gly Val Met Arg Gln Cys Lys Cys Ile Arg Gln Cys
        35                  40                  45
```